(12) United States Patent
Narayan et al.

(10) Patent No.: US 12,171,488 B2
(45) Date of Patent: Dec. 24, 2024

(54) TREATMENT SYSTEM WITH SENSING AND ABLATION CATHETER FOR TREATMENT OF HEART RHYTHM DISORDERS

(71) Applicant: PhysCade, Inc., Palo Alto, CA (US)

(72) Inventors: Sanjiv M. Narayan, Palo Alto, CA (US); Dylan R. Montgomery, Murrieta, CA (US); Steven D. Thompson, Murrieta, CA (US); Jonathan S. Ciulla, Temecula, CA (US); Peter J. D'Aquanni, Murrieta, CA (US); Andy E. Denison, Temecula, CA (US); Melissa Donovan-Green, Temecula, CA (US); Jose Alvarado, Temecula, CA (US); Mahmood I. Alhusseini, Menlo Park, CA (US); Bret A. Herscher, Cupertino, CA (US)

(73) Assignee: PhysCade, Inc., Palo Alto, CA (US)

( * ) Notice: Subject to any disclaimer, the term of this patent is extended or adjusted under 35 U.S.C. 154(b) by 0 days.

(21) Appl. No.: 17/884,220

(22) Filed: Aug. 9, 2022

(65) Prior Publication Data
US 2023/0049942 A1    Feb. 16, 2023

Related U.S. Application Data

(60) Provisional application No. 63/231,669, filed on Aug. 10, 2021.

(51) Int. Cl.
  *A61B 18/14*    (2006.01)
  *A61B 18/00*    (2006.01)

(52) U.S. Cl.
  CPC .. *A61B 18/1492* (2013.01); *A61B 2018/0016* (2013.01); *A61B 2018/00267* (2013.01);
  (Continued)

(58) Field of Classification Search
  CPC ........... A61B 2018/00029; A61B 2018/00035; A61B 2018/00214; A61B 2018/00226;
  (Continued)

(56) References Cited

U.S. PATENT DOCUMENTS 5,476,495 A * 12/1995 Kordis ................... A61B 5/287
                                                    600/374
6,231,570 B1    5/2001 Tu et al.
  (Continued)

FOREIGN PATENT DOCUMENTS

EP    3777743 A1    2/2021
EP    3791816 A2    3/2021
  (Continued)

OTHER PUBLICATIONS

Annotated Kordis (Year: 2023).*
  (Continued)

*Primary Examiner* — Michael F Peffley
*Assistant Examiner* — Nicholas S Borsch
(74) *Attorney, Agent, or Firm* — Fenwick & West LLP

(57) ABSTRACT

A novel catheter is disclosed comprising an electrode array that is capable of switching between a sensing configuration for sensing electrical signals of biological tissue and an ablation configuration for delivery of ablation energy at a region of interest. Irrigation ports are interlaced within the electrode array to vent irrigant during an ablation procedure to; prevent excessive heating, charring of tissue, coagulation of blood, and allow for efficient delivery of ablation therapy for maximum therapy efficacy. The novel catheter includes a plurality of splines with linear portions wherein the electrodes of the electrode array are disposed. The splines are connected by connectors which include one or more bends capable of storing potential energy when the bends are elastically deformed, enabling collapse and expansion of the
  (Continued)

catheter in a sheath. Software logic associated with this catheter analyzes sensing signals to diagnose critical regions of the biological rhythm disorder, and enables directional guidance to move the catheter to critical regions for therapy.

18 Claims, 46 Drawing Sheets

(52) U.S. Cl.
CPC ............... *A61B 2018/00357* (2013.01); *A61B 2018/00642* (2013.01); *A61B 2018/00702* (2013.01); *A61B 2018/00791* (2013.01); *A61B 2018/00839* (2013.01); *A61B 2018/00875* (2013.01); *A61B 2218/002* (2013.01)

(58) Field of Classification Search
CPC ........... A61B 2018/00232; A61B 2018/00238; A61B 2018/0025; A61B 2018/00261; A61B 2018/0022; A61B 2018/00255; A61B 2018/00267; A61B 2018/0016
See application file for complete search history.

(56) References Cited

U.S. PATENT DOCUMENTS

| | | |
|---|---|---|
| 7,300,438 B2 | 11/2007 | Falwell et al. |
| 7,850,685 B2 | 12/2010 | Kunis et al. |
| 8,715,199 B1 | 5/2014 | Macneil et al. |
| 8,880,158 B2 | 11/2014 | Spector |
| 9,033,892 B2 | 5/2015 | Su et al. |
| 9,050,006 B2 | 6/2015 | Narayan et al. |
| 9,078,583 B2 | 7/2015 | Nguyen et al. |
| 9,101,333 B2 | 8/2015 | Schwartz |
| 9,186,081 B2 | 11/2015 | Afonso et al. |
| 9,271,680 B2 | 3/2016 | Dubois et al. |
| 9,282,910 B2 | 3/2016 | Narayan et al. |
| 9,332,915 B2 | 5/2016 | Narayan et al. |
| 9,370,329 B2 | 6/2016 | Tun et al. |
| 9,427,169 B2 | 8/2016 | Zeng et al. |
| 9,474,491 B2 | 10/2016 | Li et al. |
| 9,554,847 B2 | 1/2017 | Govari et al. |
| 9,687,166 B2 | 6/2017 | Subramaniam et al. |
| 10,016,233 B2 | 7/2018 | Pike |
| 10,070,795 B2 | 9/2018 | Macneil et al. |
| 10,105,179 B2 | 10/2018 | Harlev et al. |
| 10,136,829 B2 | 11/2018 | Deno et al. |
| 10,143,374 B2 | 12/2018 | Ruppersberg |
| 10,194,994 B2 | 2/2019 | Deno et al. |
| 10,524,684 B2 | 1/2020 | Fay et al. |
| 10,568,686 B2 | 2/2020 | Lee |
| 10,617,467 B2 | 4/2020 | Viswanathan et al. |
| 10,864,031 B2 | 12/2020 | Mazor et al. |
| 10,912,472 B2 | 2/2021 | Finlay et al. |
| 10,980,602 B2 | 4/2021 | Deno et al. |
| 11,051,867 B2 | 7/2021 | Babkin et al. |
| 2002/0095151 A1* | 7/2002 | Dahla ................. A61B 18/148 606/41 |
| 2002/0107511 A1* | 8/2002 | Collins .............. A61B 18/1492 606/41 |
| 2003/0204185 A1* | 10/2003 | Sherman ............ A61B 18/1492 606/41 |
| 2008/0281310 A1* | 11/2008 | Dunning ................ A61B 18/16 607/152 |
| 2009/0318749 A1 | 12/2009 | Stolen et al. |
| 2010/0291521 A1 | 11/2010 | Simon |
| 2011/0257563 A1 | 10/2011 | Thapliyal et al. |
| 2013/0282084 A1* | 10/2013 | Mathur .............. A61B 18/1492 607/101 |
| 2013/0296679 A1* | 11/2013 | Condie ................ A61B 5/6856 600/374 |
| 2014/0114204 A1 | 4/2014 | Narayan et al. |
| 2014/0128859 A1* | 5/2014 | Lee .......................... A61L 29/14 156/60 |
| 2014/0276712 A1* | 9/2014 | Mallin ............... A61B 18/1492 606/33 |
| 2015/0254419 A1 | 9/2015 | Laughner et al. |
| 2015/0282729 A1 | 10/2015 | Harlev et al. |
| 2017/0156791 A1* | 6/2017 | Govari ................... A61B 5/287 |
| 2017/0202515 A1 | 7/2017 | Zrihem et al. |
| 2017/0202521 A1 | 7/2017 | Urman et al. |
| 2017/0232263 A1* | 8/2017 | Narayan ................ A61N 1/378 600/509 |
| 2017/0332971 A1 | 11/2017 | Macneil |
| 2019/0076179 A1 | 3/2019 | Babkin et al. |
| 2020/0085311 A1 | 3/2020 | Tzvieli et al. |
| 2020/0138319 A1 | 5/2020 | Spector |
| 2020/0229866 A1 | 7/2020 | Harlev et al. |
| 2020/0345261 A1 | 11/2020 | Haeusser et al. |
| 2020/0352652 A1 | 11/2020 | Amit et al. |
| 2021/0085204 A1 | 3/2021 | Auerbach et al. |
| 2021/0106249 A1 | 4/2021 | Schmidt et al. |
| 2021/0259765 A1 | 8/2021 | Narayan |
| 2021/0315627 A1 | 10/2021 | Babkin et al. |
| 2022/0015682 A1 | 1/2022 | Spector et al. |
| 2022/0338923 A1 | 10/2022 | Bort et al. |
| 2023/0277112 A1 | 9/2023 | Weiss et al. |
| 2023/0363643 A1 | 11/2023 | Tran |

FOREIGN PATENT DOCUMENTS

| | | |
|---|---|---|
| WO | WO 2013/013098 A1 | 1/2013 |
| WO | WO 2013/106557 A1 | 7/2013 |
| WO | WO 2017/165830 A1 | 9/2017 |
| WO | WO 2017/165846 A1 | 9/2017 |
| WO | WO 2017/192617 A1 | 11/2017 |
| WO | WO 2024/003509 A1 | 1/2024 |

OTHER PUBLICATIONS

Alhusseini, M., et al., "Two Independent Mapping Techniques Identify Rotational Activity Patterns at Sites of Local Termination During Persistent Atrial Fibrillation," Journal of Cardiovascular Electrophysiology, vol. 28, Issue 6, Jun. 2017, pp. 615-622.

Anfinsen, O. G., et al., "Bipolar radiofrequency catheter ablation creates confluent lesions at larger interelectrode spacing than does unipolar ablation from two electrodes in the porcine heart," European Heart Journal, vol. 19, Issue 7, Jul. 1, 1998, pp. 1075-1084.

Atteberry, J., "How 2-D Bar Codes Work," HowStuffWorks.com, Mar. 3, 2011, [Online][Retrieved Feb. 21, 2023], Retrieved from the internet <URL:https://science.howstuffworks.com/innovation/repurposed-inventions/2d-barcodes.htm>.

Baykaner, T., et al., "Clinical Implications of Ablation of Drivers for Atrial Fibrillation," Circulation: Arrhythmia and Electrophysiology, vol. 11, Issue 5, May 2018, e006119. 10 pages.

Binkowski, B. J., et al., "How to avoid unnecessary RF applications in cavo-tricuspid isthmus: common atrial flutter ablation using 8-mm-tip mini-electrode-equipped catheter," Journal of Interventional Cardiac Electrophysiology, vol. 60, Issue 1, pp. 109-114.

Buist, T. J., et al., "Efficacy of multi-electrode linear irreversible electroporation," EP Europace, vol. 23, Issue 3, Mar. 2021, pp. 464-468.

Clarnette et al., "Outcomes of persistent and long-standing persistent atrial fibrillation ablation: a systematic review and meta-analysis," EP Europace, vol. 20, Issue FI_3, Nov. 2018, pp. f366-f376.

Dekker, L. R., "Last call on nMARQ safety," EP Europace, vol. 18, Issue 8, Aug. 2016, pp. 1119-1120.

Glashan, C. A., et al., "Multisize Electrodes for Substrate Identification in Ischemic Cardiomyopathy: Validation by Integration of Whole Heart Histology," JACC: Clinical Electrophysiology, vol. 5, Issue 10, Oct. 2019, pp. 1130-1140.

Haines, De, et al., "Microembolism and Catheter Ablation I: A Comparison of Irrigated Radiofrequency and Multielectrode-phased Radiofrequency Catheter Ablation of Pulmonary Vein Ostia," Circulation: Arrhythmia and Electrophysiology, Feb. 2013, vol. 6, Issue 1, pp. 16-22.

(56) References Cited

OTHER PUBLICATIONS

Hummel, J., et al., "Evaluation of stroke incidence with duty-cycled multielectrode-phased radiofrequency ablation of persistent atrial fibrillation results of the Victory AF Study," Journal of Cardiovascular Electrophysiology, vol. 31, Issue 6, Jun. 2020, pp. 1289-1297.
International Search Report and Written Opinion, Patent Cooperation Treaty Application No. PCT/US2022/029630, Oct. 26, 2022, 31 pages.
International Search Report and Written Opinion, Patent Cooperation Treaty Application No. PCT/US2022/039873, Jan. 30, 2023, 21 pages.
Invitation to Pay Additional Fees, Patent Cooperation Treaty Application No. PCT/US2022/022609, Jun. 3, 2022, 3 pages.
Iwasawa, J., et al., "Temperature-Controlled Radiofrequency Ablation for Pulmonary Vein Isolation in Patients With Atrial Fibrillation," Journal of the American College of Cardiology, vol. 70, Issue 5, Aug. 2017, pp. 542-553.
Kardos, A., et al., "Cavotricuspid isthmus ablation with large-tip gold alloy versus platinum-iridium-tip electrode catheters," Pacing and Clinical Electrophysiology, vol. 32, Suppl 1, Mar. 2009, pp. S138-140.
Koruth, J. S., et al., "Feasibility, safety, and durability of porcine atrial ablation using a lattice-tip temperature-controlled radiofrequency ablation catheter," Journal of Cardiovascular Electrophysiology, vol. 31, Issue 6, Jun. 2020, pp. 1323-1331.
Kowalewski, "Interaction of Localized Drivers and Disorganized Activation in Persistent Atrial Fibrillation," Circulation: Arrhythmia and Electrophysiology, vol. 11, Issue 6, Jun. 2018, e005846, pp. 1-12.
Lee, J.M., et al., "The Electrical Isolation of the Left Atrial Posterior Wall in Catheter Ablation of Persistent Atrial Fibrillation," JACC: Clinical Electrophysiology, vol. 5, Issue 11, Nov. 2019, pp. 1253-1261.
Lewalter, T., et al., "Gold vs. platinum-iridium tip catheter for cavotricuspid isthmus ablation: the AURUM 8 study," EP Europace, vol. 13, Issue 1, Jan. 2011, pp. 102-108.
Lewalter, T., et al., "Gold-Tip Electrodes—A New "Deep Lesion" Technology for Catheter Ablation? In Vitro Comparison of a Gold Alloy Versus Platinum-Iridium Tip Electrode Ablation Catheter," Journal of Cardiovascular Electrophysiology, vol. 16, Issue 7, Jul. 2005, pp. 770-772.
Lin et al., "Comparison of phase mapping and electrogram-based driver mapping for catheter ablation in atrial fibrillation," Pacing and Clinical Electrophysiology, Author manuscript; available in PMC May 30, 2019, published in final edited form as: Pacing and Clinical Electrophysiology, vol. 42, Issue 2, Feb. 2019, pp. 216-223.
Linhart, M., et al., "Superiority of Gold versus Platinum Irrigated Tip Catheter Ablation of the Pulmonary Veins and the Cavotricuspid Isthmus: A Randomized Study Comparing Tip Temperatures and Cooling Flow Requirements," Journal of Cardiovascular Electrophysiology, vol. 23, Issue 7, Jul. 2012, pp. 717-721.
Mahida, S., et al., "nMARQ Ablation for Atrial Fibrillation: Results from a Multicenter Study," Journal of Cardiovascular Electrophysiology, vol. 26, Issue 7, Jul. 2015, pp. 724-729.
Michaud, G. F., "Asymptomatic Cerebral Emboli with the PVAC Gold: Worth Another Look?" JACC: Clinical Electrophysiology, vol. 5, Issue 3, Mar. 2019, pp. 327-329.
Michaud, G. F., et al., "Rapid Point-by-Point Pulmonary Vein Isolation," JACC: Clinical Electrophysiology, vol. 5, Issue 7, Jul. 2019, pp. 787-788.
Nazer, B., "Feasibility of Rapid Linear-Endocardial and Epicardial Ventricular Ablation Using an Irrigated Multipolar Radiofrequency Ablation Catheter," Circulation: Arrhythmia and Electrophysiology, Mar. 2017, vol. 10, Issue 3, e004760, pp. 1-9.
Parameswaran et al., "Clinical impact of rotor ablation in atrial fibrillation: a systematic review," EP Europace, vol. 20, Issue 7, Jul. 2018, pp. 1099-1106.
Petersen, H. H., et al., "Tissue temperatures and lesion size during irrigated tip catheter radiofrequency ablation: an in vitro comparison of temperature-controlled irrigated tip ablation, power-controlled irrigated tip ablation, and standard temperature-controlled ablation." Pacing and Clinical Electrophysiology, vol. 23, Issue 1, Jan. 2000, pp. 8-17.
Ramirez et al., "Efficacy and safety of driver-guided catheter ablation for atrial fibrillation: A systematic review and meta-analysis," Journal of Cardiovascular Electrophysiology, vol. 28, Issue 12, Dec. 2017, pp. 1371-1378.
Reddy, V. Y., et al., "Pulmonary Vein Isolation with Very High Power, Short Duration, Temperature-Controlled Lesions: The QDOT-FAST Trial," Journal of Cardiovascular Electrophysiology, vol. 5, Issue 7, Jul. 2019, pp. 778-786.
Scharf, C., et al., "Ablation of Persistent Atrial Fibrillation Using Multielectrode Catheters and Duty-Cycled Radiofrequency Energy," Journal of the American College of Cardiology, vol. 54, Issue 15, Oct. 2009, pp. 1450-1456.
Swerdlow, M., et al., "Comparing phase and electrographic flow mapping for persistent atrial fibrillation," Pacing and Clinical Electrophysiology, Author manuscript; available in PMC May 1, 2020, published in final edited form as: Pacing and Clinical Electrophysiology, vol. 42, Issue 5, May 2019, pp. 499-507.
Wijffels, M., et al., "Characterization of In Vitro and In Vivo Lesions Made by a Novel Multichannel Ablation Generator and a Circumlinear Decapolar Ablation Catheter," Journal of Cardiovascular Electrophysiology, vol. 20, Issue 10, Oct. 2009, pp. 1142-1148.
Woodford, C., "Barcodes and barcode scanners," ExplainthatStuff.com, 12 pages, last updated: Jun. 14, 2022, [Online] [Retrieved Feb. 21, 2023], Retrieved from the internet <URL:https://www.explainthatstuff.com/barcodescanners.html>.
Zaman, Jab, et al., "Identification and characterization of sites where persistent atrial fibrillation is terminated by localized ablation," Circulation: Arrhythmia and Electrophysiology, Jan. 2018, vol. 11, Issue 1, e005258, pp. 1-12.
United States Non-Final Office Action, U.S. Appl. No. 18/418,043, filed Apr. 16, 2024, 31 pages.

* cited by examiner

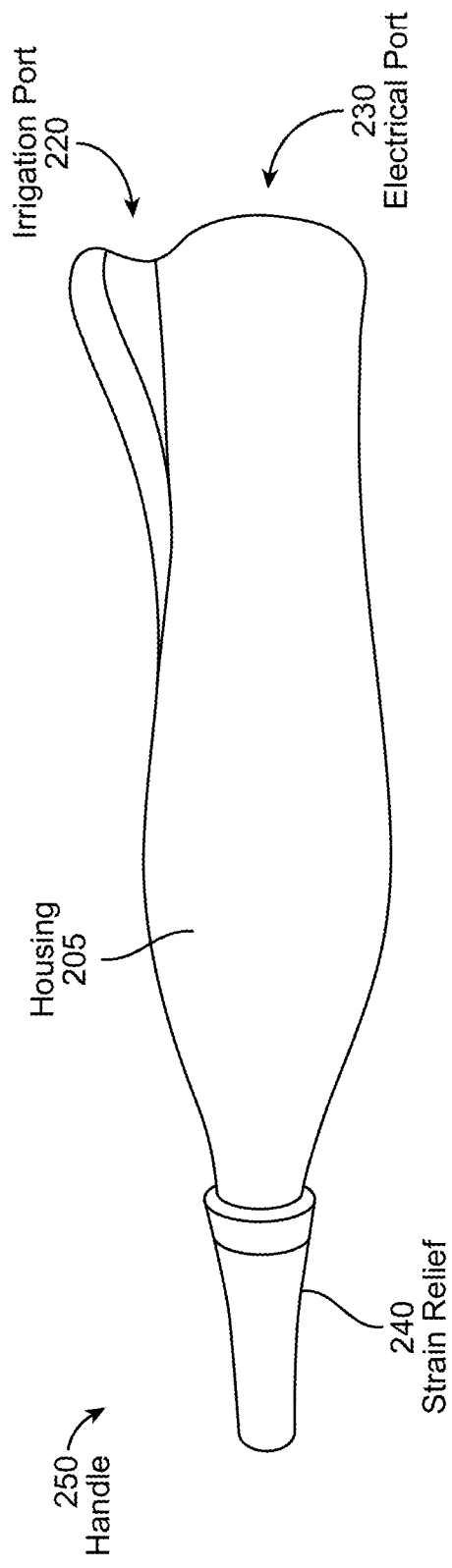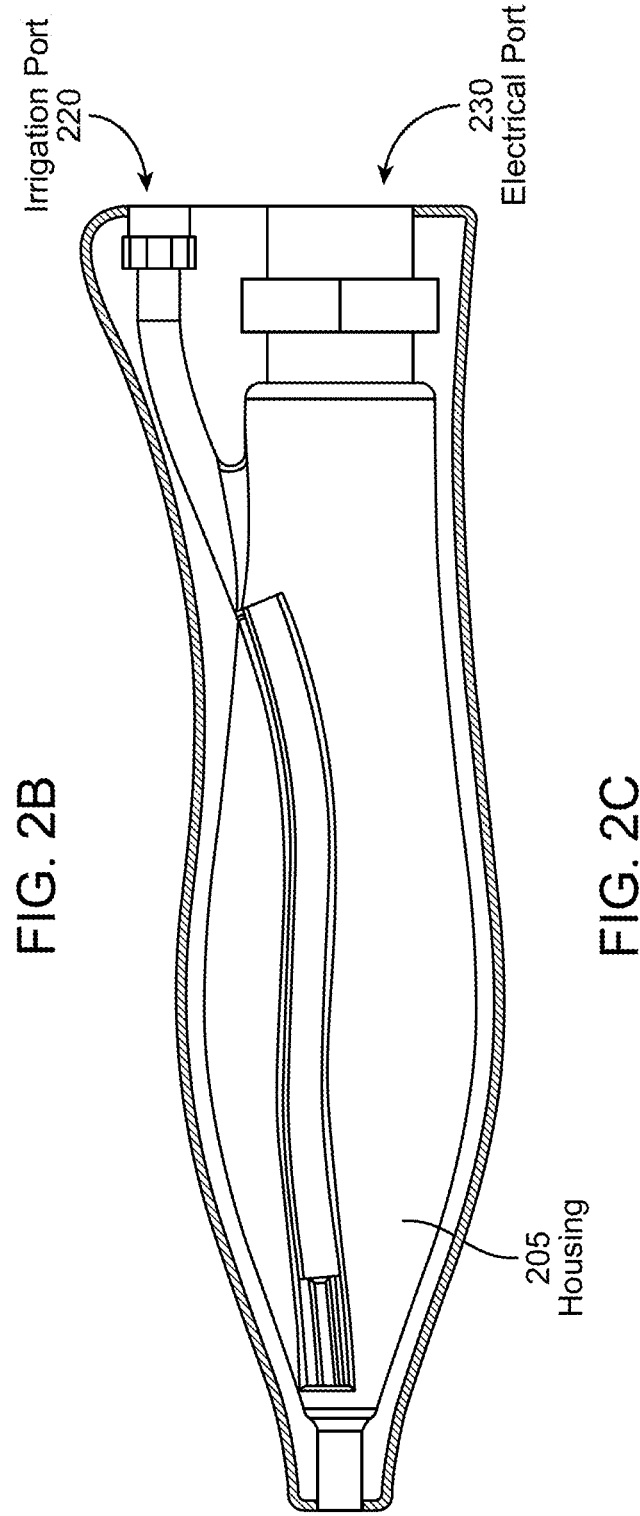
FIG. 2B
FIG. 2C

462

464

466

468

470

Figure 4D. Ablation from 0.8 x 1.0 mm
Ablation of area > 1 x 1 cm from 4X4 sub-array of electrodes (each 0.8 x 1 mm, 3 mm center-to-center spacing)
Ablation of full heart wall thickness (pig atrium), thickness >3 mm, area > 1 cm x 1 cm from 4X4 electrode array
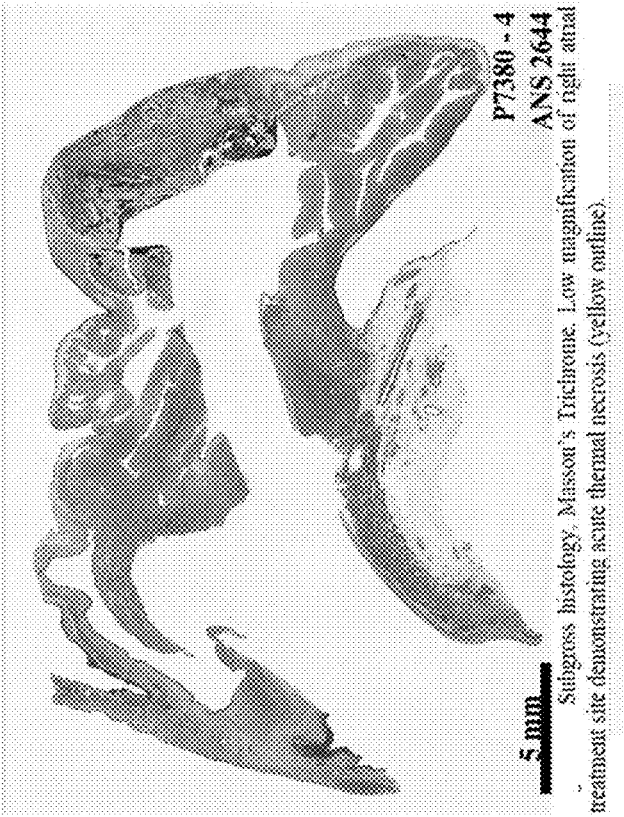

762

764

766

768

770

862

864

866

868

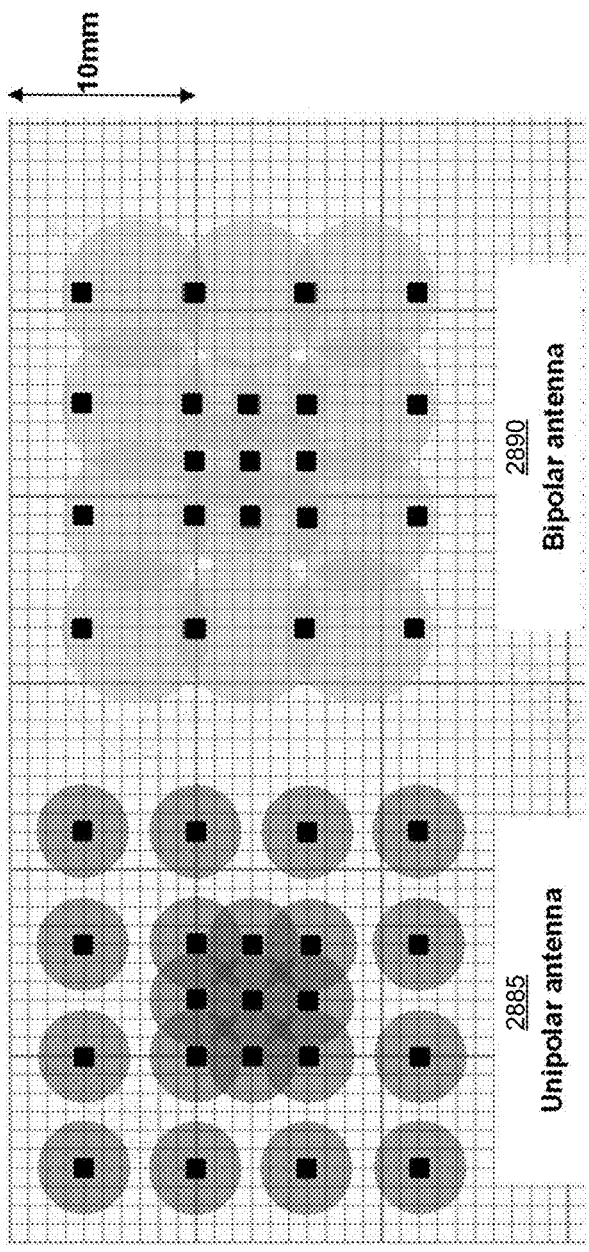

TREATMENT SYSTEM WITH SENSING AND ABLATION CATHETER FOR TREATMENT OF HEART RHYTHM DISORDERS

CROSS-REFERENCE TO RELATED APPLICATIONS

The present application claims the benefit of and priority to U.S. Provisional Application No. 63/231,669 filed on Aug. 10, 2021, which is incorporated by reference in its entirety.

BACKGROUND

Field of the Art

This present disclosure generally relates to systems for the treatment of biological rhythm disorders, including invasive catheters with targeting software.

Conventional invasive treatment of biological rhythm disorders uses separate catheters for sensing and mapping electrical tissue signals and distinct catheters for the ablation of critical regions (also termed sources) for the biological rhythm disorders. The use of separate catheters introduces limitations and can result in unsynchronized positioning and movement of mapping and therapy catheters, requires logic or software systems to reconcile differences between catheter signals or positions, extends the length of the procedure to enable catheter exchanges which reduces efficiency and may introduce side-effects including air or clot into the bloodstream. There remains a need for a system comprising a catheter capable of providing high-spatial and high-temporal resolution sensing, for integration with appropriate logic or software to analyze sensed signals into mapping critical regions to apply treatment, and being able to switch into an ablation configuration for ablation tailored to the results of mapping of the biological rhythm disorder under consideration.

SUMMARY

The present invention relates to a novel system comprising a catheter as part of a diagnostic and treatment device for biological rhythm disorders. The novel catheter is capable of both sensing electrical signals in tissue and ablating regions showing selected electrical patterns, in a spatial configuration that is optimal both for software systems to map and detect critical regions of the biological rhythm disorder, to enable navigational guidance to critical regions of interest, then to deliver appropriate patterns of ablation to eliminate said biological rhythm disorder. The novel catheter comprises a housing that supports two or more electrodes for sensing electrical signals and/or for delivering ablation energy to tissue. In one embodiment, the housing is designed as a plurality of splines on which an electrode array is disposed. The electrode array comprises a plurality of electrodes, wherein each electrode can be configured to sense signals or to deliver ablation energy or both. Alternatively, there may be some electrodes for sensing signals and some to deliver ablation energy. Sensing electrical signals enables mapping of changes in the biological rhythm disorder, and also assessment of the efficacy of ablation via electrical changes such as signal amplitude or impedance. In some embodiments, electrodes can sense temperature via components such as thermocouples which, coupled to appropriate electronic circuitry, enables energy delivery to be controlled in real-time to maintain a target temperature. Thus, the device can be designed with individual electrodes that have a single function or ones that have multiple functions, or a combination of both types of electrodes. In either case, the overall electrode array itself may provide dual functionality. The dual functionality of the electrode array for sensing and therapy delivery simplifies the treatment process, as it enables the catheter to be guided towards a critical region for the rhythm disorder including a source identified by software system or logic, based on optimal sensing and interpretation of electrical signals, and enables the same catheter to deliver ablation energy in a pattern or patterns optimized for the biological rhythm disorder in this specific patient.

In one or more embodiments, the catheter comprises splines that hold one or more electrodes. Each spline may take the shape of a straight line, the arc of a circle or a zig-zag, as optimal for the specific biological rhythm disorder under consideration. In one or more embodiments, the novel catheter includes a plurality of connector struts (also referred throughout this disclosure as "connectors") attached to the splines. The connector struts are composed of a substantially rigid but deformable material including one or more pre-shaped bends designed to store compressive energy. When the splines are retracted into a sheath or introducer tool, they collapse in proximity to one another enabling the catheter to be accommodated within a guide catheter of smaller dimensions to be advanced into the organ or withdrawn from it. Collapsing the splines deforms the connector struts so that the splines oppose geometrically in the sheath without the need for undue force, thereby storing compressive energy in the bends. When the splines are extended from the sheath, the compressive energy stored in the connectors is released, returning the connector struts to a relaxed state where the splines are spaced apart from one another in their sensing and ablating configuration. In one or more embodiments, the splines and the connector struts that each adjoin one or more splines may be monolithically formed, e.g., laser cut from a sheet of material. The implementation of the connector struts provides for a creative solution for easy expansion and collapse of the catheter from the sheath.

In one or more embodiments, the novel catheter includes a plurality of irrigation pores that may be associated with the plurality of electrodes in the array, for example interlaced between electrodes. The irrigation pores provide controlled irrigation of saline, half-normal saline, low temperature fluids or other solutions during ablation by the novel catheter. Irrigation while ablating tissue reduces and prevents charring of tissue from the ablation, enables delivery of power deeper within tissue due to cooling, and may enhance ablation by the chemical or biophysical properties of the irrigating solution.

In one or more embodiments, a method is disclosed for optimizing the configuration of the electrode array for a particular patient. The method includes sensing electrical signals of the patient (e.g., via an invasive or a non-invasive diagnostic device) and selecting an optimized portion of electrodes from those on the array based on the sensed electrical signals, and which may include other factors related to the biological state for that patient. Alternatively, a physician may select one catheter from a plurality of catheters with an electrode array configuration and sizing optimized for the patient. The physician then delivers ablation from the selected subset of electrodes within the array, or from the selected catheter size/configuration for treatment of the patient's biological rhythm disorder.

In some embodiments, the system can identify and locate critical regions (source or dominant regions) for biological rhythm disorders. The catheter records electrical signals from within the organ, and software logic relates these signals to known and computer-derived patterns of critical regions. Computer-derived patterns represent stereotypical or expected patterns obtained from rules, databases, algorithmic functions, machine learning or other logical functions. The software logic of the system is then able to provide navigational guidance towards critical regions based on analysis of sensing electrical signals. This same catheter within the system can be used to directly deliver treatment to these regions. In some embodiments, these steps can also be estimated based on knowledge of how patients with similar data patterns respond to therapy, rather than on the actual sensing electrical signals or patterns in that patient alone. This estimate can be obtained from machine learning or other pattern association techniques. The steps of machine learning based on data from patients with similar data patterns can also be used to select an optimal subset of electrodes from the array to be used to detect signals and then to deliver ablation treatment.

The system and method described herein thus provide a process for personalized therapy for biological rhythm disorders, that is simplified because it combines high-resolution mapping of the rhythm disorder, navigational guidance to critical regions of interest, then tailored therapy for the rhythm disorder from the same apparatus. This can increase efficiency and also efficacy of the procedure. The system can be used in conjunction with other treatment which may include a combination of lifestyle changes, medications, electrical or mechanical treatment, surgical or minimally invasive ablation from other catheter systems, genetic or stem cell therapy. In some embodiments, the system and process has the ability to deliver personalized therapy using data from the current individual but also estimated using machine learning of data from other individuals with similar profiles. The process of identifying individuals with similar profiles is based on digital classification that can be updated using strategies such as crowd-sourcing. This enables learning on an ongoing basis.

BRIEF DESCRIPTION OF THE DRAWINGS

FIG. 2B illustrates a side view of a handle of the heart treatment device, according to one or more embodiments.

FIG. 2C illustrates an internal view of a handle of the heart treatment device, according to one or more embodiments.

FIG. 4D illustrates ablation of heart tissue by the first catheter in one or more embodiments.

FIG. 11A is a side view of the tenth catheter.

FIG. 11B is a head-on view down the center axis of the tenth catheter.

FIG. 11C is a perspective view of the tenth catheter.

FIG. 12A is a side view of the eleventh catheter.

FIG. 12B is a head-on view down the center axis the eleventh catheter.

FIG. 12C is a perspective view of the eleventh catheter.

FIG. 28C illustrates the analogous parameters for irregularly spaced electrode configurations with a dense central cluster and a more sparse peripheral region, according to one or more embodiments.

Figure 1:
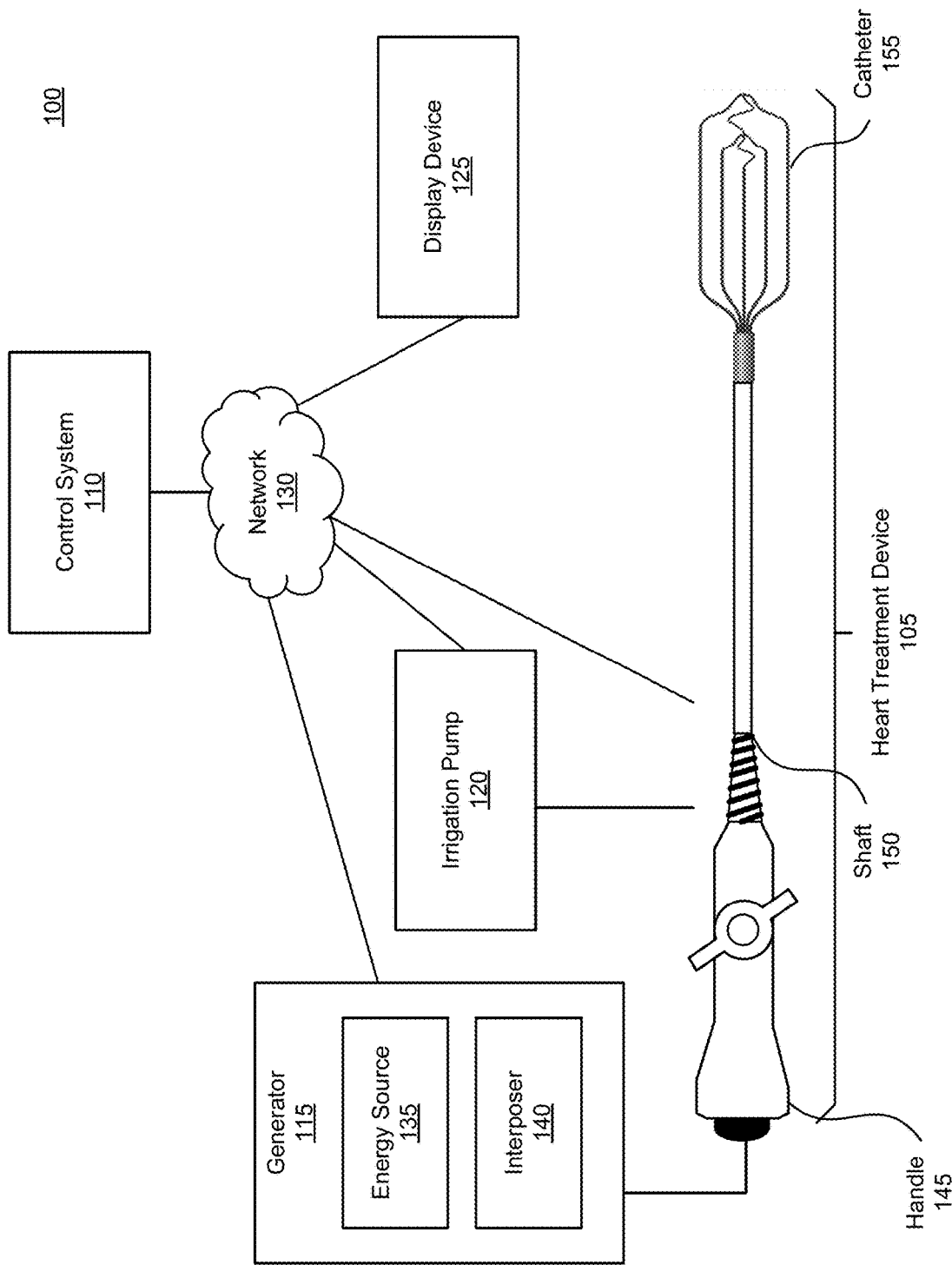
FIG. 1 illustrates an environment for the operation of a heart treatment device, according to one or more embodiments.

In each figure, there can be more or fewer components and/or steps than shown, or certain components and/or steps can be replaced with others or can be organized or ordered in a different manner than is shown.

DETAILED DESCRIPTION

Overview

The present invention relates to a novel system for use in a diagnostic and/or treatment device for the management of biological rhythm disorders, comprising a catheter and software for mapping and identification of critical regions (sources) of the biological rhythm disorder for therapy. The novel catheter is capable of both sensing electrical signals in tissue and ablating source regions. While the description is focused throughout primarily on this embodiment of the catheter that is designed to perform both functions, other embodiments of the catheter are designed to perform only one or the other of these functions. The novel catheter comprises a distal end or a housing that includes one or more electrodes, such as at least one electrode that can both sense electrical or temperature signals and ablate tissue, or at least two electrodes, where one can sense signals (also referred to as a "sensing electrode") and one can ablate tissue (also referred to as an "ablation electrode"). There can also be a combination of electrodes that can sense signals, electrodes that can ablate tissue, or electrodes that can do both. In an embodiment, the distal end or housing includes an electrode array. As an example, the distal end or housing may be configured as a plurality of splines on which an electrode array is disposed. The electrode array comprises a plurality of electrodes, wherein each electrode can be configured to sense electrical signals and to deliver ablation energy to tissue. The dual functionality of the electrode array coupled with appropriate logic or software simplifies the treatment process and makes it more efficient, as the same catheter can be used for both guiding the catheter towards a critical or source region based on sensed electrical signals and then delivering optimal patterns of ablation energy using all electrodes or subsets of electrodes from the same catheter array. In some cases, one or more (or all) of the electrodes in the array on the splines are single functionality electrodes.

In one or more embodiments, the novel catheter includes a plurality of connector struts attached to the splines. The connectors are composed of a substantially rigid yet deformable material with one or more engineered bends that can store compressive energy. When the splines are retracted into a sheath, the splines collapse in proximity to one another. Collapsing the splines deforms the connector struts so that the splines oppose geometrically in the sheath without the need for undue force, thereby storing compressive energy in the bends. When the linear splines are subsequently extended from the sheath, the compressive energy stored in the connector struts are released, returning them to their relaxed state where the splines are spaced apart from one another for optimal sensing and ablation energy delivery. The implementation of connector struts provides a creative solution for easy expansion and collapse of the catheter from the sheath.

In one or more embodiments, the novel catheter includes a plurality of irrigation pores that may be interlaced within the electrode array. The irrigation pores provide controlled irrigation during ablation by the novel catheter. Irrigation while ablating tissue prevents charring of tissue from the ablation, and enables ablation energy to penetrate deeper into tissue.

In one or more embodiments, a method is disclosed for optimizing the electrode array for a particular patient. This involves selecting the electrode configuration that provides optimal recording and potentially unrecorded tissue areas for that patient's biological rhythm disorder. The method first requires sensing electrical signals of the patient, that can be achived via additional invasive or non-invasive diagnostic devices or in other embodiments using subsets of electrodes in the array. In this way, an optimized electrode array for the patient is determined, and may reflect subsets of the existing array selected in software, or a separate physical catheter from a plurality of catheters with an electrode array sizing and configuration, that matches the optimal array determined for the patient. The physician then utilizes this selected configuration during treatment of the patient's biological rhythm disorder. In another embodiment, the physician could specify a design for a custom electrode configuration on a catheter that is specific for a particular patient (or a collection of patients with common characteristics or treatment needs), and this custom catheter could be manufactured to treat a specific patient (or collection of patients).

In some embodiments, the system can identify and locate critical regions (source or dominant regions) for biological rhythm disorders. The catheter records electrical signals from within the organ, and software logic relates these signals to known and machine-learned patterns of critical regions. The software logic of the system then provides navigational guidance towards critical regions based on analysis of the recorded electrical signals. This same catheter within the system can be used to directly deliver treatment to these regions. In some embodiments, these steps can also be estimated based on knowledge of how patients with similar data patterns respond to therapy, rather than on the actual electrical patterns recorded in that patient alone. These estimates can be based on machine learning of patterns, or other methods including algorithmic solutions. The steps of machine learning based on data from patients with similar data patterns can also be used to select an optimal subset of electrodes from the array to be used to detect signals and then to deliver therapy.

The system and method described herein thus provide a process for personalized therapy for heart rhythm disorders, that is simplified because it combines high-resolution mapping of the biological rhythm disorder, navigational guidance to critical regions of interest, then tailored therapy for the rhythm disorder from the same apparatus. This can also increase efficiency of the procedure. The system can be used in conjunction with other therapy which may include a combination of lifestyle changes, medications, electrical or mechanical therapy, surgical or minimally invasive ablation from other catheter systems, genetic or stem cell therapy. In some embodiments, the system and process have the ability to deliver personalized therapy using data from the current individual but also to estimate therapy using machine learning of data from other individuals with similar profiles. The process of identifying individuals with similar profiles is based on digital classification that can be updated using strategies such as crowd-sourcing from multiple individuals. This enables learning on an ongoing basis.

For simplicity purposes of the foregoing discussion, the treatment device discussed is in relation to treatment of heart rhythm disorders, such as Atrial Fibrillation. However, the discussion may be generalized to cover other types of biological rhythm disorders arising from misaligned electrical signals in biological tissue. The claimed invention generally provides navigational guidance towards critical or source regions based on the detected electrical signals by the novel catheter. Treatment may also be tailored to each patient based on the detected electrical signals. Treatment may also include, in addition to ablation therapy: immunosuppression therapy, stem cell therapy, gene therapy, drug therapy, other types of medical therapies, or any combination thereof.

The process may apply to biological rhythm disorders of the heart including those of heart rhythm, of mechanical contraction, of heart failure, of abnormalities of the coronary blood vessels that supply the heart with blood, or of nerve-related function ("the autonomic nervous system"). Other exemplary applications include electrical disorders of the brain including seizure disorders, diseases of gastro-intestinal rhythm such as irritable bowel syndrome, and bladder disease including detrusor instability. The process may apply to chaotic disorders in these organs, such as atrial fibrillation in the heart or generalized seizures in the brain, as well as simple rhythm disorders. These examples are in no way designed to limit the scope of the disclosure for other conditions.

The process may identify patients in whom critical regions for a biological rhythm disorder arise near standard therapy targets or not. An example of this embodiment is to identify patients with atrial fibrillation (AF) who are likely or unlikely to benefit from standard pulmonary vein isolation (PVI) ablation. In patients who are unlikely to benefit from PVI, the device may identify critical regions (or sources) in regions of the heart other than the pulmonary veins (PV). Such critical regions may be amenable to therapy such as ablation. In patients in whom critical regions or localized sources are not identified, the device can identify patients in whom standardized therapy such as a Maze surgery may work, using signal processing including machine learning of signal patterns in patients in whom Maze surgery did or did not work. This approach can be used to identify patients in whom other ablation types (so-called lesion sets) may or may not work based on recognizing patterns of patients in whom each lesion set was or was not successful. In other embodiments, the device can identify patients with heart rhythm disorders such as ventricular tachycardia or atypical atrial flutter in whom ablation will or will not be successful.

Sites of origin of a heart rhythm disorder are defined as the first beat or beats (within the first 30 seconds, typically the first 5-10 beats) which initiate the heart rhythm from normal rhythm. For instance, AF often initiates by a few premature atrial beats, often near one of the pulmonary veins of the heart. The device is capable of identifying these originating or triggering beats. If these beats arise from the pulmonary veins, ablation to isolate the pulmonary veins and eliminate these triggers may be effective. In another patient in whom many or most trigger beats do not arise from the pulmonary veins, PVI may not be effective.

Source regions of interest are different from sites of origin, and drive the heart rhythm disorder once it has initiated. Source regions can be identified as patches of organized activity (a) within chaotic disorders such as atrial fibrillation, or (b) from which activation emanates in organized rhythms such as atrial tachycardia or ventricular tachycardia. In some embodiments, the process uses analytical tools including signal processing (mathematical algorithms), artificial intelligence or machine learning to detect source regions as organized patches of the heart.

Sources for the biological rhythm disorder may represent rotational activity, focal activity, repetitive activity of other patterns, regions of irregular activity, activity associated with structural abnormality such as scar or fibrosis, or other patterns. Well defined patterns are focal or reentrant (rotational) site. For atrial fibrillation (AF), sources may be any of these patterns. Source information is conveyed to the operator.

In some embodiments, the process can identify a series of sources for the biological rhythm, pointing out the most important for therapy in a hierarchy. For AF, this differs from the prior art that often recommends treating all sources, which requires mapping, detection and therapy of less-critical regions that is time consuming, adds complexity to the procedure and may have adverse effects. Less-critical regions may be false-positives that do not require therapy.

In some embodiments, a device can identify important source regions for the rhythm disorder by quantifying their size or area, or by using other features such as rate or stability over time. This can be applied to organized drivers for a heart rhythm disorder such as atrial fibrillation or ventricular fibrillation. This also applies to the source driving tonic/clonic seizures in the brain. This also applies to a focus that drives irritable bowel syndrome. These features of critical regions for the heart rhythm disorder are used to design the size and configuration of electrodes for optimal detection, and the configuration and pattern of ablation therapy delivery for optimal treatment planning.

In some embodiments, the process can identify critical regions for the biological rhythm disorder without the need for wide-area 'global' mapping catheters. In the heart, examples of such global catheters include baskets which are cumbersome, cannot provide the high spatial resolution mapping available through this device, may not cover the entire organ despite being termed 'global' and, even if ablation can be delivered, may not do this with the precision and uniformity required to eliminate the critical region with confidence.

In some embodiments, the process can use additional information such as from non-invasive body surface potential mapping or even versions of the ECG to provide a 'global view' to complement to even replace intracardiac catheters inside the heart. The relative sizes of these fields of view can be complementary, such as a global map from the body surface and a catheter inside the heart to provide a focused field of view at high spatial resolution.

An application in an electronic device such as a smartphone, smart tablet, or smart device can help guide the user and record the necessary positions of the patches using its optical camera, Lidar sensor (infrared, ultraviolet, or other), or both (only location of electrodes will be recorded relative to anatomy, photos will not be saved or transmitted to the Cloud). Appropriate attached and location recording will ensure proper processing of data. Alternatively, the device might have a built-in indicator to ensure proper positioning and attachment of the device.

Definitions

In some embodiments, "associative learning" may refer to a process of linking input data with measurable physiology or clinical outcome. Associative learning may be iterative, enabling associations to be modified ("learned") based upon patterns of change between input and measured output (physiological or clinical endpoints).

In some embodiments, "biological signal" may refer to a signal produced by the body of a subject, and may reflect the state of one or more bodily systems. For instance, the heart rate reflects cardiac function, autonomic tone and other factors.

In some embodiments, "biometric signals" may refer to signals that provide metrics of human characteristics. Biometric identifiers can be physiological or behavioral. Physiological biometrics include, but are not limited to, DNA, fingerprints or palm prints, mouth swabs, tissue or urine samples, retinal images, facial recognition, the geometry of hands or feet, recognition of the iris or odor/scent of an individual. Physiological biometrics may also include signals such as vital signs, the ECG, the EEG, EMG, and so on. Behavioral biometrics include patterns such as gait during walking or typing rhythm. Embodiments described in this disclosure may use dynamic patterns of combined physiological and behavioral biometrics over time, which adapt to changes in the individual and are thus robust to forgery from prior "versions" of a person's signature.

In some embodiments, "body" may refer to the physical structure of a human or an animal for veterinary work.

In some embodiments, "data streams" or "stream(s) of data" or "data" may refer to biological data sensed by one or more sensors that can provide real-time or near-real-time information on the biological process being sensed. Sensors in the heart may provide data comprising the electrocardiogram (ECG), Electrogram (EGM), pulse rate, pulse waveform and cardiac hemodynamics. Other data may include cardiac acoustics, including analysis of heart sounds, murmurs and sophisticated analyses of hemodynamics related to the heart. Lung function may be sensed as chest movement, auscultatory sounds and nerve firing associated with breathing. Gastrointestinal disease may be sensed as sounds (borborygmi), movement on the abdominal wall, and electrical signals related to smooth muscle activity of the gut. Central and peripheral nervous system activity may be sensed as nerve activity on the scalp (electroencephalogram, EEG), remote from the scalp but still reflecting the EEG, and from peripheral nerve firing.

In some embodiments, "demographics" may refer to personal information which may include, but is not limited to, age, gender, family history of disease, ethnicity, and presence of comorbidities and which may be clinically relevant.

In some embodiments, "digital classification" may refer to a partition of different states of disease or health based on mathematical indexes. Traditional disease classifications are qualitative, such as "atrial fibrillation is more common in the older individuals, those with heart comorbidities such as valvular lesions or heart failure, those with metabolic syndrome". A digital classification translates this broad dataset into quantifiable primary and secondary data elements (data vectors). The likelihood that a disease entity $D_n$ is present in a specific individual is approximated by the probability $p(D_n)$:

$$p(D_n) = \sum_{i=1}^{m} \frac{(k_n p(V_{n,i}))}{k_n}$$

Where m is the number of available data input types, n is the disease being considered, and $p(V_{n,i})$ is the probability that data vector $V_{n,i}$ contributes to disease n for input i, and $k_n$ is a weighting constant for disease n. These elements are integrated into the classification, which computes probabilities that a specific data input contributes to disease. Probabilities can be obtained from population data, in which the profile of a specific person is matched to the most-similar individuals or profiles in that population. The probability can also be obtained from data in this individual alone, compared to times of health (self-reported or adjudicated) and times of disease (self-reported or adjudicated). These calculations can be performed by traditional estimating equations but may also by statistical techniques and machine learning. A digital classification (i.e. a classification) represents a disease entity stochastically by the aggregate of abnormalities in multiple related data inputs. This process is dynamic since the equation reflecting disease will change when data is added, when data changes, and when the state of health or disease is updated. This is an approach to integrate massive amounts of data from traditional data sources as well as wearable devices in an individual, or massive amounts of data from several individuals as a crowd-sourced paradigm.

In some embodiments, "electrocardiographic imaging (ECGI)" is a data source that refers to a process that records body surface potentials on the chest then uses mathematics to calculate electrical activity at precise regions of the heart. The inverse solution develops mathematical transforms that may need detailed knowledge of anatomy inside the chest, typically provided by computed tomography (CT) or magnetic resonance imaging (MRI), or from standardized anatomical databases, and make assumptions about their conductivity, resistance and other electrical properties. In this way, body surface potentials can be mapped to the heart.

In some embodiments, an "electrocardiographic (ECG) patch" may refer to a device that includes electrodes to sense cardiac rhythm. The ECG patch may be a data source. The ECG patch may be placed in regions of the body, such as on the back. Depending on the body placement and approaches used to analyze data generated by the ECG patch, the ECG patch can discriminate heart rhythm activation patterns of interest. In some embodiments, an ECG patch on the back can record atrial activation to guide AF therapy, which can be tailored to best record activity in women versus men, and for different rhythm applications. The ECG patch does not necessarily require CT or MM imaging for analysis, and is a form of body surface potential mapping without mapping the entire body torso.

In some embodiments, "historical data" may refer to stored data, which may include reports from medical imaging, e.g., magnetic resonance imaging (MRI), computed tomography (CT), radiological, or other scans of an organ, data from genetic testing analyses (e.g., presence of one or more genomic variants), previously-obtained ECG reports, pathology, cytology, information on genomic variants (genetic abnormalities and non-disease causing variations), and other laboratory reports. This also includes clinical demographics such as age, gender, other conditions present in the individual, and a family history of diseases. Historical data may further include additional personal historical details that could be relevant to generating the personal digital record, for example, socioeconomic status including income strata, mental illness, employment in a high-stress profession, number of pregnancies (in women), engaging in high-risk behaviors such as smoking, drug or alcohol abuse, etc.

In some embodiments, "machine learning" may refer to a series of analytic methods and algorithms that can learn from and make predictions on data by building a model. Machine learning is classified as a branch of artificial intelligence that focuses on the development of computer programs that can automatically update and learn to produce predictions when exposed to data. In some embodiments, machine learning is one tool used to create the digital network and personal digital records linking sensed or recorded data with a specific output such as response to therapy, or ability to maintain normal rhythm. For applications in the brain, outputs could include absence of seizure activity. Machine learning techniques include supervised learning, transfer learning, semi-supervised learning, unsupervised learning, or reinforcement learning. Several other classifications may exist.

In some embodiments, "unsupervised machine learning" may include methods of training of models with training data without the need for training labels. Techniques in unsupervised machine learning may include cluster analysis that may be used to identify internal links between data (regardless of whether data is labeled or unlabeled). In some embodiments, patterns (clusters) could be identified between clinical data (such as diagnosis of atrial fibrillation, or presence of heart failure, or other disease), family history, data from physical examinations (such as regularity of the pulse, low blood pressure), data from sensors (such as altered temperature, altered skin impedance), electrical data (atrial waveforms on the ECG), imaging data (enlarged left atrium or reduced), biomarkers, genetic and tissue data as available. Another technique is to use autoencoders, to featurize and compress input data. Autoencoders are sometimes described as 'self-supervised' since the model input and output are the same.

In some embodiments, "supervised machine learning" may include methods of training of models with training data that are associated with labels. Techniques in supervised machine learning may include methods that can classify a series of related or seemingly unrelated inputs into one or more output classes. Output labels are typically used to train the learning models to the desired output, such as favorable patient outcomes, accurate therapy delivery sites and so on. Supervised learning may also include a technique known as 'transfer learning', where a pretrained machine learned model trained on one set of input or task, is retrained or fine-tuned to predict outcomes on another input or task.

In some embodiments, "semi-supervised machine learning" may refer to a process that combines techniques from supervised and unsupervised machine learning to address cases where a large amount of data is available but only a portion of the data is labeled. One approach is to impute or infer labels from similar data, based on a comparison of the data under consideration to other data within the database. Another approach is to generate labels for an unlabeled dataset based on the portion of data that is labeled. Yet another approach is to use training from a different problem or a different dataset to generate labels for these data. Such techniques are used to improve the learning accuracy of models by creating "pseudo labels" for the unknown labels (an approach known as transductive learning) and to improve model learning by adding in more input to output examples (inductive learning).

In some embodiments, "reinforcement learning" may refer to a form of machine learning which focuses on how software agents take actions in a specific environment to maximize cumulative reward. Reinforcement learning is often used in game theory, operations research, swarm intelligence and genetic algorithms and has other names such as approximate dynamic programming. One implementation in machine learning is via formulation as a Markov Decision Process (MDP). Reinforcement learning may differ from supervised machine learning in that it may not use matched inputs and labeled outputs, and actions that result in sub-optimal rewards are not explicitly corrected (unlike supervised learning which may correct suboptimal rewards via e.g., back propagation algorithms in a perceptron).

In some embodiments, a "medical device" may refer to an instrument, apparatus, implement, machine, contrivance, implant, in vitro reagent, or another similar or related article, including a component part, or accessory, which is intended for use in the diagnosis of disease or other conditions, or in the cure, mitigation, treatment, or prevention of disease, in man or other animals.

In some embodiments, "neural networks" may refer to a class of machine learning models that include interconnected nodes that can be used to recognize patterns. Neural networks can be deep or shallow neural networks, convolutional neural networks, recurrent neural networks (gated recurrent units, GRUs, or long short term memory, LSTM, networks), generative adversarial networks, and auto-encoders neural networks. Artificial neural networks can be combined with heuristics, deterministic rules and detailed databases.

In some embodiments, "personal digital records" may include data related to health or disease of an individual. The personal digital records may integrate several clinical data streams which may or may not include cellular, genomic, proteomic, metabolomic or other data. The personal digital record may be stratified, partitioned or separated by desired groups, such as response to specific therapy, presence of a heart rhythm disorder, presence or seizure activity of the brain, good health or other attribute in that person. The personal digital record for an individual can be compared to a digital classification of data from a large group to identify individuals with 'similar' profiles. This comparison to similar profiles may be done mathematically and, once done, may enable predictions or selection of optimal therapy based on the successful response of those similar individuals. In some embodiments, the comparison may take the form of a mathematical 'best estimation' since all required data may not be available in the personal digital record of a given patient or in the digital classification.

Personal digital records enable personalized medicine in an individual. This is an alternative to the 'one size fits all' approach that commonly applies one therapy or approach to all patients of a subjective 'type'. Data elements used to create the personal digital record may represent the individual's health state, weighted by their likely contribution to the specific disease or index of health being considered. Personal digital records may be matched to a digital classification by algorithms that take into account the calculated or documented probability of the impact of each data type on health or disease. This may use deterministic algorithms or iterative processes including machine learning. For example, a personal digital record for heart rhythm may primarily consider heart rate and electrographic signals (surface ECG and intracardiac), and then consider heart function, prior history of heart rhythm issues, prior therapies, and so on. Greater mathematical weighting may be given to these data elements. Data from other organ systems can also then be included, and can enable a more comprehensive assessment and a closer match to other individuals in a digital classification. Such other data streams may include changes in breathing rate (e.g., lung sensors), changes in nerve firing rate (e.g., nerve function). Other data elements may include abnormal cardiac ejection fraction, location and presence of structural abnormalities of the heart. Historical data including age, gender, medication use, family history, laboratory values and genetic data can also be included in the personal digital record.

In some embodiments, "population data" may refer to a determinant of the accuracy of a process. This is to create a digital classification of patients in the population. The classification may include some or all data elements in the personal digital record of the individual under consideration. Mathematical analyses are used to compare the personal digital record of the individual to the digital classification and calculate the best match. If the index individual is very different from the reference population then the digital classification may not adequately represent this individual. In this case, data may be derived primarily from that individual, using prior data at times of adjudicated health or adjudicated illness. If the reference population is broad but has other limitations, such as not having sufficient data points for an accurate digital classification, or not having well-labeled data, the classification may be less useful. In some embodiments, the ideal data set may include data that are well labeled and from a large number of individuals that represent the entire population, which can be grouped by desired outcome to create a digital classification.

In some embodiments, "sensors" include devices that can detect biological signals from the body of an individual. A sensor may be in direct contact with the body or may be remote. When applied to a group of individuals, sensors may represent all or part of a defined population. Electromagnetic sensors can sense electromagnetic signals relating to the electromyogram (EMG), electroencephalogram (EEG), electrocardiogram (ECG), nerve firing, electromagnetic light (visible or invisible such as near infrared or infrared) or other emitters. In some cases, the term "sensor", especially when describing certain cardiac applications in which electrical information is detected, may be used interchangeably with "electrode", "electrode catheter", "probe" or "catheter." Electrical sensors can also detect bioimpedance, such as conductance across the skin that decreases in the presence of electrolyte solutions such as sweat when a person perspires, and that may occur during times of sympathetic nervous system predominance. Sensors can also detect other chemical changes via current flows. Sensors also include devices that detect temperatures, such as a thermistor or other thermal detector. Sensors can detect light such as changes in the color of reflected or emitted light from heart activity (photoplethysmography), changes in peripheral oxygenation (e.g., cyanosis, anemia, vasodilation on the skin). Sensors can detect sound via a microphone. This can be used to sense sounds from the heart, lungs or other organs. Sensors can detect contact force, pressure, or other vibrations or movement via piezoelectric elements. Sensors can detect chemicals directly, using specialized sensors for hormones, drugs, bacteria and other elements that are typically transduced on the device to an electrical signal. Examples include motion sensing of chest wall movement from a breath or heartbeat, chest wall vibrations from certain types of breath (e.g., a loud obstructive breathing sound) or heart sound (e.g., a so-called "thrill" in the medical literature). Breath sensors can detect movement of the chest wall, abdomen or other body parts associated with ventilation, or acoustic data (sound) associated with breaths, or oxygenation associated with breathing. Chemical sensors can detect chemical signals on the skin or other membranes that reflect body chemistry such as oxygenation and deoxygenation, acidosis (pH), stress (catecholamines), glucose levels, certain drugs or other states that will be familiar to those skilled in the biochemistry arts. Sensors can also detect images using a camera or lens requiring contact from the fingerprint or other body part, or sense movement from specific muscles, or sense iris dilation or oscillations from photosensors in a contact lens. Positional sensors can identify positions of body parts and changes over time (including gait) or contact sensing of the position of certain body parts at one point in time or over time (e.g., a facial droop, a facial tick or another idiosyncratic movement). In exemplary embodiments of the inventive system, multiple sensors may be used in communication with a central computing device or which may form a network linked via BLUETOOTH, WI-FI, or other protocol to form an intranet or internet of things (IoT) of biological sensors.

In some embodiments, "signal" may include electronic, electromagnetic, digital or other information that can be sensed or acquired. Sensing signals are detected unaltered from their natural form (e.g., recorded) with no transformation. Sensing signals are typically biological signals. Sensing signals can be detected by humans (e.g., sound, visual, temperature) but also machines such as microphones, auditory recorders, cameras, thermometers. Acquired signals are detected in a transformed state, such as an ECG recording. Such signals may be biological, since cardiac bioelectricity generates the ECG, or non-biological signals, e.g., vibration sensed after application of sonic or ultrasonic energy, or a haptic signal transduced from a sensed electrical, sonic or another signal. Signals may be sensed via physical contact with a sensor.

The following description and accompanying figures provide examples of applications of the inventive system and method for personalizing treatment by analyzing personal digital records of health and disease, to detect regions of interest for biological rhythm disorders and treat such regions of interest. The examples described herein are intended to be illustrative only. As will be evident to those of skill in the art, additional variations and combinations may be formed employing the inventive principles disclosed herein.

Treatment System

FIG. 1 illustrates a treatment system 100 for the operation of a heart treatment device 105, according to one or more embodiments. The treatment system 100 includes the heart treatment device 105, the control system 110, a generator 115, an irrigation pump 120, and a input/output device 125. The various components of the treatment system 100 are connected via a network 130. Additional or fewer components may be implemented in the treatment system 100. For example, another non-invasive device comprising a wearable electrode array can be utilized in conjunction with the other components shown in FIG. 1. Other embodiments incorporate an external sheath, which is first inserted into the patient and translocated to the treatment site, followed by insertion of the heart treatment device 105 into the sheath.

The heart treatment device 105 is used for invasive access and treatment of heart rhythm disorders. The heart treatment device 105 includes, among other components, a handle 145, a shaft 150, and a catheter 155. The handle 145 is where a physician or automated control system controls movement of the shaft 150 and the catheter 155. The handle 145 also includes interfaces for connection to other components in the treatment system 100, e.g., the generator 115, the irrigation pump 120, and the network 130. The shaft 150 is inserted into a patient via a vascular access point. The shaft 150 is directed to the tissue requiring treatment. The catheter 155 is deployed from the shaft 150, where the catheter 155 is configured to sense electrical signals for guidance of the catheter 155 and to deliver ablation energy to one or more source regions identified in the tissue. The various components of the heart treatment device 105 will be further described in the figures below.

Figure 26:
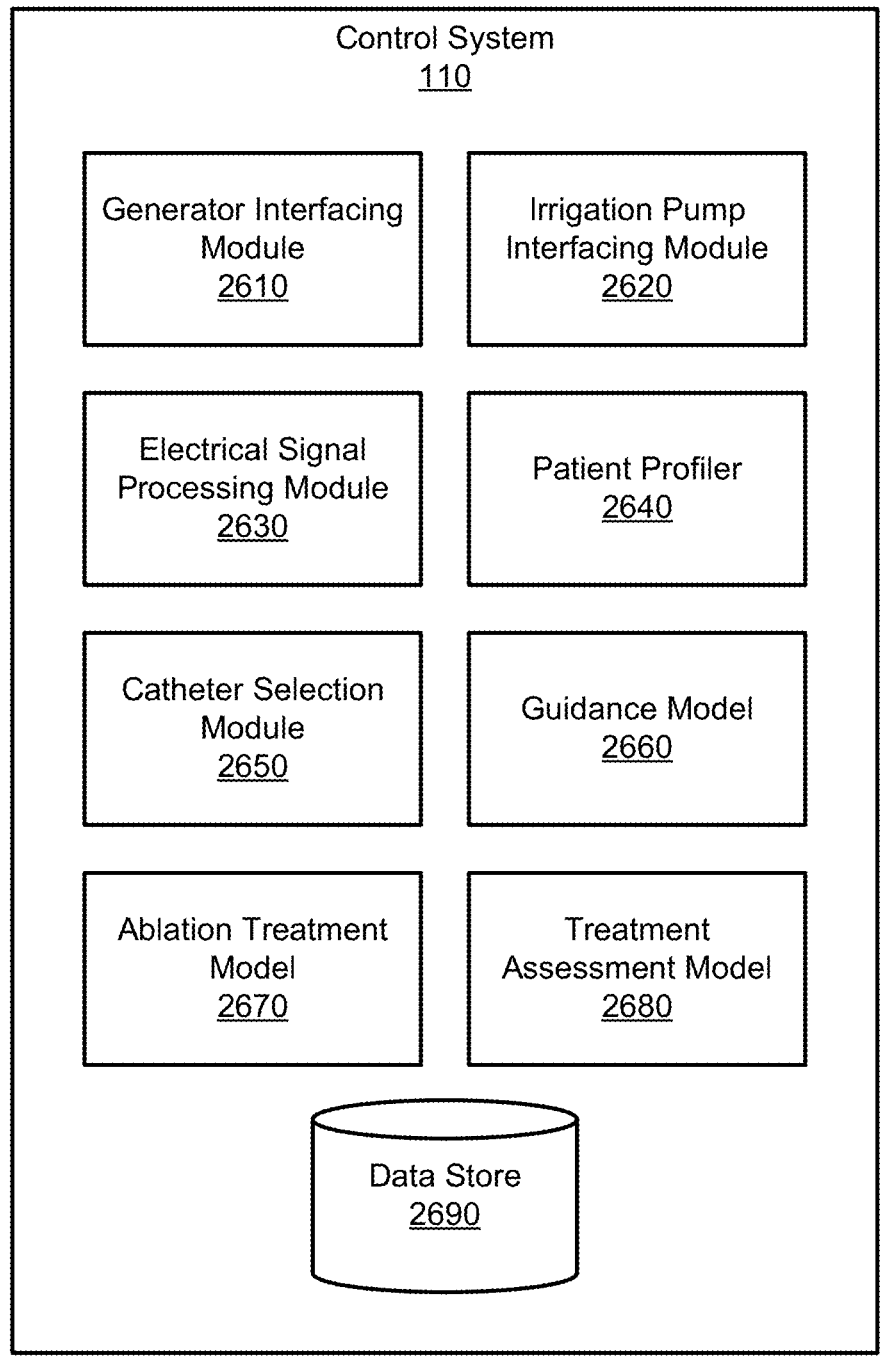
FIG. 26 illustrates a block diagram of the control system used in conjunction with the heart treatment device, according to one or more embodiments.

The control system 110 controls the various components of the treatment system 100. The control system 110, further described in FIG. 26, is configured to receive data from the various components and provide instructions to the various components. For example, the control system 110 receives electrical signals sensed by the heart treatment device 105. The control system 110 may process and analyze the electrical signals to determine guidance controls for the heart treatment device 105. The control system 110 may provide the guidance controls for movement of the catheter 155 when deployed and in contact with the patient's heart. The control system 110 may further determine an optimal ablation procedure upon identifying the location of a source region in the patient's heart that is a contributor to the heart rhythm disorder. The control system 110 may provide instructions for carrying out the ablation procedure to the generator 115, the irrigation pump 120, and the heart treatment device 105. The control system 110 may also receive inputs from a user, e.g., a physician, to aid in the treatment procedure. The control system 110 may also provide real-time data and/or updates to the input/output device 125 for displaying such data and/or updates during the treatment procedure.

The generator 115 provides electrical energy to the heart treatment device 105 for performing an ablation procedure. The generator 115 may comprise an energy source 135 and an interposer 140. The energy source 135 generates the electrical energy for use in the ablation procedure. The energy source 135 may in turn fetch the electrical energy from another energy source (e.g., an electrical outlet, an electricity generator, a battery, etc.) for conversion into the electrical energy for use in the ablation procedure. For example, the ablation procedure requires a particular energy frequency, a particular waveform, a particular duration, other ablation procedure parameters, etc. The energy source 135 can then generate electrical energy at the appropriate frequency, with the appropriate waveform, and for the appropriate duration. The interposer 140 electrically connects the energy source 135 to the electrode array on the catheter 155. The interposer 140 may control connection to each electrode of the electrode array. For example, if the ablation procedure requires actuation of a subset of the electrodes in the electrode array, then the interposer 140 may switch off connections for the remaining electrodes not required during the ablation procedure. As another example, the interposer 140 may control which mode each electrode is operating in. As described above, the electrode array of the novel catheter 155 is advantageous in that each electrode may be used for sensing and ablation. The interposer 140 may utilize switches connected to each electrode, for switching the electrode between a sensing mode, an ablation mode, and an off mode (e.g., the electrode being connected to an electrical ground). The interposer 140 is further described in FIGS. 25A & 25B.

The irrigation pump 120 controls pumping of irrigant to the heart treatment device 105. The irrigation pump 120 may include various vessels and fluid channels for directing stored irrigant to the heart treatment device 105. The types of irrigant that may be used include: a chemical buffer or a saline infusate. Delivery of irrigant during an ablation procedure prevents overheating of the heart tissue and the catheter 155, which avoids scarring of the heart tissue and potential damage to the catheter 155. Prevention of overheating also allows for deeper energy delivery without needing to prematurely stop the ablation procedure, providing greater efficacy in the ablation procedure.

The input/output device 125 is configured to display visual data to a user of the heart treatment device 105, e.g., a physician. The input/output device 125 may be a touch display capable of receiving user inputs. In such embodiments, the input/output device 125 may present a graphical user interface that a user is capable of interacting with. The user can provide inputs to the control system 110, e.g., inputs for adjusting operation of the various components. Example controls include steering of the heart treatment device 105 whilst in the patient, deploying and/or retracting the catheter of the heart treatment device 105 whilst in the patient, controlling a start of an ablation procedure, toggling parameters for the generator 115, toggling parameters of the irrigation pump 120, among other operations described herein this disclosure. The input/output device 125 can provide a real-time mapping of the patient's heart tissue as sensed by the electrode array of the heart treatment device 105. Upon identification of one or more source regions, the control system 110 may alert the physician via the input/output device 125. The input/output device 125 may provide further updates during treatment, e.g., during the ablation procedure.

The network 130 provides connections to the components of the treatment system 100 through one or more sub-networks, which may include any combination of local area and/or wide area networks, using both wired and/or wireless communication systems. In some embodiments, a network 130 uses standard communications technologies and/or protocols. For example, a network 130 may include communication links using technologies such as Ethernet, 802.11, worldwide interoperability for microwave access (WiMAX), 3G, 4G, Long Term Evolution (LTE), 5G, code division multiple access (CDMA), digital subscriber line (DSL), etc. Examples of network protocols used for communicating via the network 130 include multiprotocol label switching (MPLS), transmission control protocol/Internet protocol (TCP/IP), hypertext transport protocol (HTTP), simple mail transfer protocol (SMTP), and file transfer protocol (FTP). Data exchanged over a network 130 may be represented using any suitable format, such as hypertext markup language (HTML), extensible markup language (XML), or JSON. In some embodiments, all or some of the communication links of a network 130 may be encrypted using any suitable technique or techniques such as secure sockets layer (SSL), transport layer security (TLS), virtual private networks (VPNs), Internet Protocol security (IPsec), etc. The network 130 also includes links and packet switching networks such as the Internet.

Heart Treatment Device

The heart treatment device 105 (or more generally the treatment device) comprises a handle 145, a shaft 150, and a catheter 155, though there can be different components in some embodiments. Prior to insertion into the patient, the catheter 155 is sheathed within a sheath, e.g., that may be a separate component. The shaft 150 (e.g., sheathed within the sheath) is inserted into the patient and directed to the heart tissue with the catheter 155 in a compact state. Upon reaching the heart tissue, the catheter 155 is unsheathed from the sheath, transitioning from the compact state to an expanded state, as shown in FIG. 1. In the expanded state, the catheter 155 can be moved by steering of the shaft 150. The handle 145 provides ability to (1) control transitioning of the catheter 155 between the compact state and the expanded state and (2) control movement of the catheter 155.

Figure 2A:
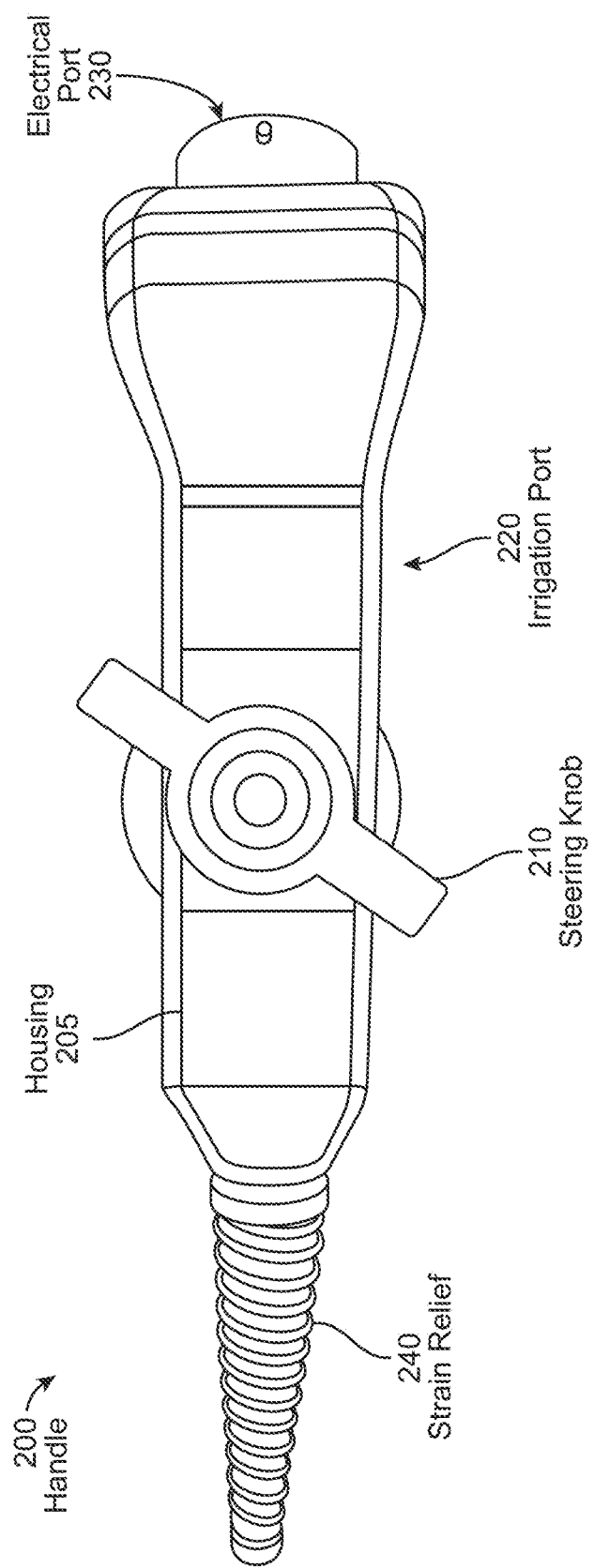
FIG. 2A illustrates a top view of a handle of the heart treatment device, according to one or more embodiments.

FIG. 2A illustrates a top view of a first handle 200 of the heart treatment device 105, according to one or more embodiments. The handle 200 comprises a housing 205, a steering knob 210, an irrigation port 220, an electrical port 230, and a strain relief 240. The handle 200 may comprise additional, fewer, or different components than those listed herein.

The housing 205 is a rigid body with an interior chamber. The housing 205 may be sized and shaped to be held by a human hand. The housing 205 may be composed of a substantially rigid material, e.g., thermoplastics. The housing 205 may be substantially non-conductive. The housing 205 has an interior chamber for routing of irrigation fluid channels and wiring for the catheter 155.

The steering knob 210 controls movement of the catheter 155. The steering knob 210, as shown in FIG. 2A, is a dial that can be rotated about an axis that is perpendicular to the plane of the paper. The steering knob 210 may be attached to one or more steering wires, such that rotation of the steering knob 210 creates tension on the steering wires. The tension created in the steering wires affects movement of the catheter 155. In one embodiment, the steering knob 210 comprises a pair of steering wires. Rotation of the steering knob 210 clockwise from a neutral position creates tension in one steering wire which induces a curvature in the shaft 150 bending the catheter 155 towards the handle 200 in a first direction. Rotation of the steering knob 210 counter-clockwise from the neutral position creates tension in the second steering wire which, consequently, induces a curvature in the shaft 150 bending the catheter 155 towards the handle 145 in a second direction, that is opposite the first direction. Other mechanisms for creating tension in the steering wires may be implemented in conjunction with or in substation of the steering knob 210, e.g., a button with three positions (left, neutral, and right) can be used to create tension in a left string causing the catheter 155 to bend towards the left or in a right string causing the catheter 155 to bend towards the right. Typically, the sheath remains relatively fixed within the blood vessel (femoral vein or femoral artery), pericardial space or other tissue plane, although some sheath movement is also provided. The catheter is sheathed and unsheathed by manual withdrawal and advancement from the handle-side of the catheter by the physician. In some embodiments, this can be achieved by motorized assistance or by entirely robotic control. The steering knob or steering controller can take on other designs as well, including a knob having a different shape or including being one or more buttons or sliders, a joystick or other video game type controller, among other designs. In one or more embodiments, a motor assembly may be implemented in the handle for controlling movement of the catheter.

The irrigation port 220 provides a connection of an irrigant fluid channel from the irrigation pump 120 to the irrigant fluid channel within the housing 205. The irrigant fluid channel within the housing 205 and routed to the catheter 155 also connect to the irrigation port 220. Irrigant that is pumped from the irrigation pump 120 flows through the fluid channel, through the irrigation port 220, and into the fluid channel routed to the catheter 155, where irrigant can be dispensed by the catheter 155, e.g., during an ablation procedure.

The electrical port 230 provides a connection between electrical wiring from the generator 115 and the electrical wiring within the housing 205. Electrical energy that is provided from the generator 115 is directed, at the electrical port 230, into the plurality of electrical wires in the housing 205 that are connected to the electrode array of the catheter 155.

The strain relief 240 provides relief from strain and other stress on the shaft 150. The strain relief 240 is an elastic portion that absorbs strain and other stresses from focusing at the transition between the flexible shaft (150) and the rigid handle (145) which could lead to kinking of the shaft in this location. In one or more embodiments, the strain relief 240 comprises a spring that surrounds the shaft 150 and may further include a protective rubber coating. Other designs for the strain relief 240 may be implemented such as a wire mesh. The strain relief 240 acts to dissipate strain in the shaft 150 along the length of this strain relief 240 that would otherwise be focused locally at the point of transition to the handle. FIG. 2 provides one example, but the strain relief 240 can take on other shapes and designs than what is shown in FIG. 2A.

FIGS. 2B & 2C illustrate a second handle 250 that may be implemented in the heart treatment device 105, according to one or more embodiments. In particular, FIG. 2B illustrates a side view of a handle of the heart treatment device 105. FIG. 2C illustrates an internal view of a handle of the heart treatment device 105, according to one or more embodiments.

The second handle 250 includes a housing 255, an irrigation port 260, an electrical port 265, and a strain relief 270, though there can be different components in some embodiments. The housing 255 is an embodiment of the housing 205. In the second handle 250, the housing 255 is shaped having a bulbous center for fitting into a palm of a user of the heart treatment device 105. The irrigation port 220 is located along a protrusion towards the proximal end of the handle 145, where irrigation channels and electrical connections would be connected to the handle 145 via the irrigation port 220 and the electrical port 230, respectively.

Figure 3A:
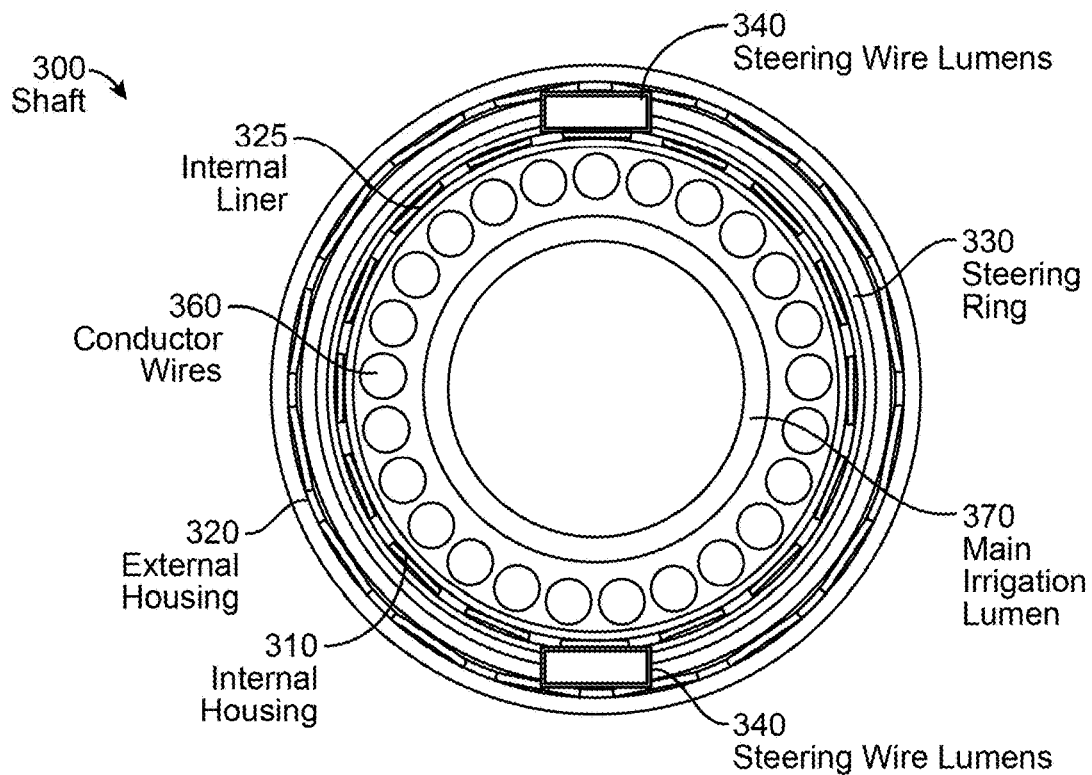
FIG. 3A illustrates a proximal cross-section view of a first shaft of the heart treatment device, according to one or more embodiments.
Figure 3B:
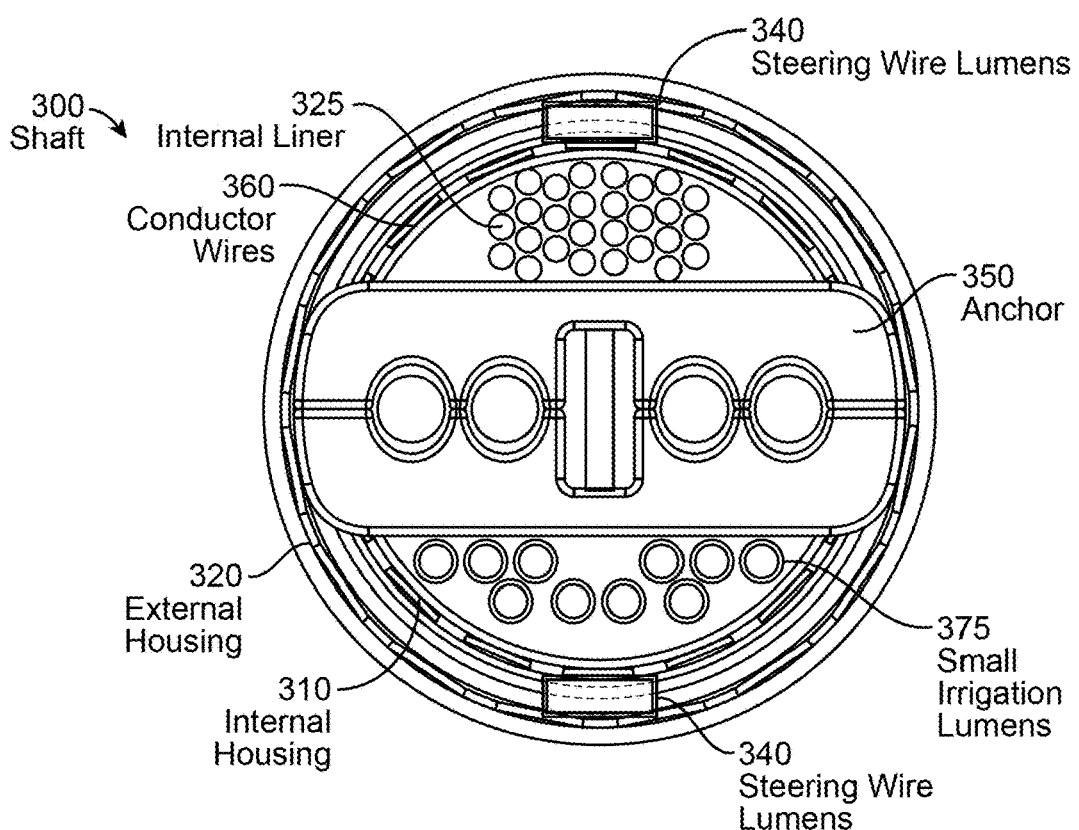
FIG. 3B illustrates a distal cross-section view of the first shaft, according to one or more embodiments.
Figure 3C:
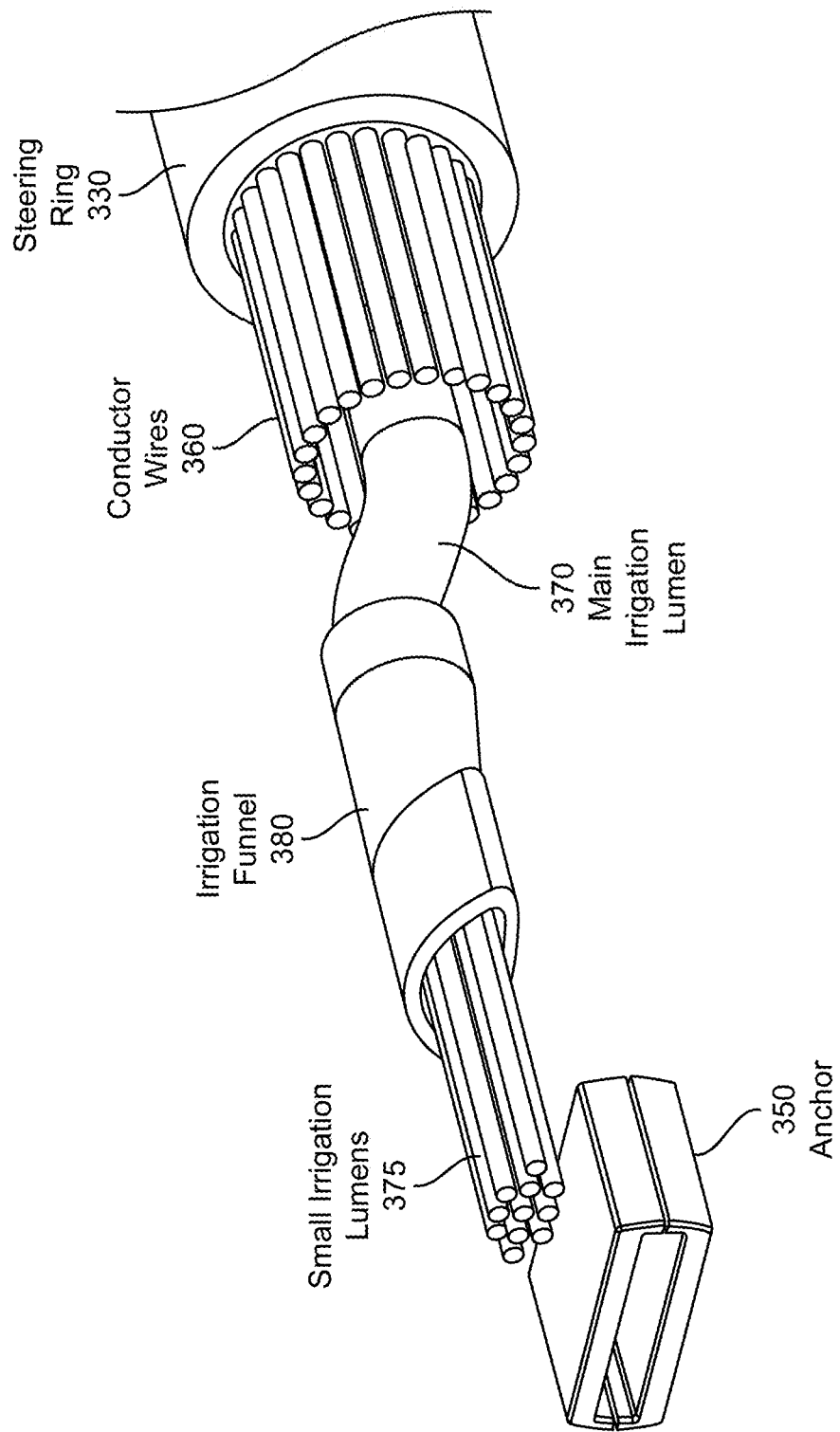
FIG. 3C illustrates a cutaway perspective view of a distal portion of the shaft 150, according to one or more embodiments.

FIGS. 3A & 3B illustrate various views of a first shaft 300 of the heart treatment device 105, according to one or more embodiments. FIG. 3A illustrates a proximal cross-section view of the shaft 300 of the heart treatment device 105, according to one or more embodiments. FIG. 3B illustrates a distal cross-section view of the shaft 300, according to one or more embodiments. FIG. 3C illustrates a cutaway perspective view of a distal portion of the shaft 300, according to one or more embodiments.

The shaft 300 is a strong and flexible cylinder that extends from the handle 145 to the catheter 155. The shaft 300 has a length to ensure that the catheter 155 can be inserted at an access point of the patient and reach the heart tissue to be treated. The shaft 300 comprises, among other components, an internal housing 310, an external housing 320, an internal liner 325, a steering ring 330, steering wire lumens 340, an anchor 350, conductor wires 360, and irrigation lumens. As shown in FIG. 3A, the shaft 300 is generally shaped as a cylinder forming a cavity, through which other components may be passed through, e.g., wiring and irrigation lumens that connect to the catheter 155. However, the shaft 300 can take on other designs as well, including having square-shaped cross section, having a different length, having different arrangement of the components shown in FIGS. 3A & 3B (e.g., fewer or more steering wire lumens 340 or different positioned steering wire lumens 340).

The internal housing 310 and the external housing 320 form the structural support for the shaft 150. The internal housing 310 and the external housing 320 may be formed from sufficiently strong yet flexible material, e.g., a metal, a metal alloy, etc. Disposed radially between the internal housing 310 and the external housing 320 is the steering ring 330. A coating layer may be coupled to the steering ring 330 to ensure no metal is exposed to the body.

On an internal surface of the internal housing 310 is an internal liner 325. The internal liner 325 may be sufficiently waterproof to prevent liquids from entering the cavity within the internal housing 310. Example material for the internal liner 325 may be polytetrafluoroethylene (PTFE) which is a synthetic fluoropolymer with hydrophobic properties.

The steering wire lumens 340 provide a cavity for steering wires to be disposed. The steering wires are connected to the steering ring 330 at a distal end of the shaft 150, i.e., in proximity to the catheter 155. When one steering wire is pulled, the pull ring is pulled to bend the shaft 150 towards the side with the pulled steering wire.

FIG. 3B illustrates a distal cross-section view showing an anchor 350. The anchor 350 couples to one or more of the other components in the shaft 300, e.g., the internal housing 310, the external housing 330, some other component, etc. The anchor 350 serves as a structural anchor for attachment of the catheter 155 to the shaft 300. Various anchors 350 that may be implemented with the catheter 155 are described below in FIG. 20, or the design may not necessarily have an anchor or the design may have a structure other than an anchor to perform a similar function.

The conductor wires 360 are conductive and configured to transmit electrical energy between the electrode array of the catheter 155 and the handle 145. The conductor wires 360 are formed of conductive materials, e.g., copper, gold, platinum, other conductive metals, other conductive metal alloys, etc. In the embodiments shown in FIGS. 3A & 3B, the conductor wires 360 are disposed radially around the irrigation lumens at a proximal end of the shaft (FIG. 3A) and transition to being disposed on one side of the anchor 350 (FIG. 3B).

The irrigation lumens form a channel for transmission of irrigant fluid between the handle 145 and the catheter 155. The irrigation lumens may be formed from rigid or compliant materials. At a proximal end of the shaft 300 (towards where the shaft 300 connects to the handle 145), the irrigation lumens may include one main irrigation lumen 370 which then splits into small irrigation lumens 375 at a distal point along the shaft 300, e.g., towards the catheter 155.

FIG. 3C illustrates a cutaway view of the transition between the main irrigation lumen 370 to the small irrigation lumens 375. In the embodiment shown, the shaft 300 further comprises an irrigation funnel 380 that connects a distal end of the main irrigation lumen 370 to proximal ends of the small irrigation lumens 385. The small irrigation lumens 375 connect to the catheter 155, e.g., to one or more irrigation pores disposed on the catheter 155. The irrigation funnel 380 is formed of a rigid material and includes one or more funneling channels that can split irrigant fluid provided from the main irrigation lumen 370 into the small irrigation lumens 375. The irrigation funnel 380 may also serve as a structural anchor to hold the irrigation lumens in place within the shaft 150.

Figure 3D:
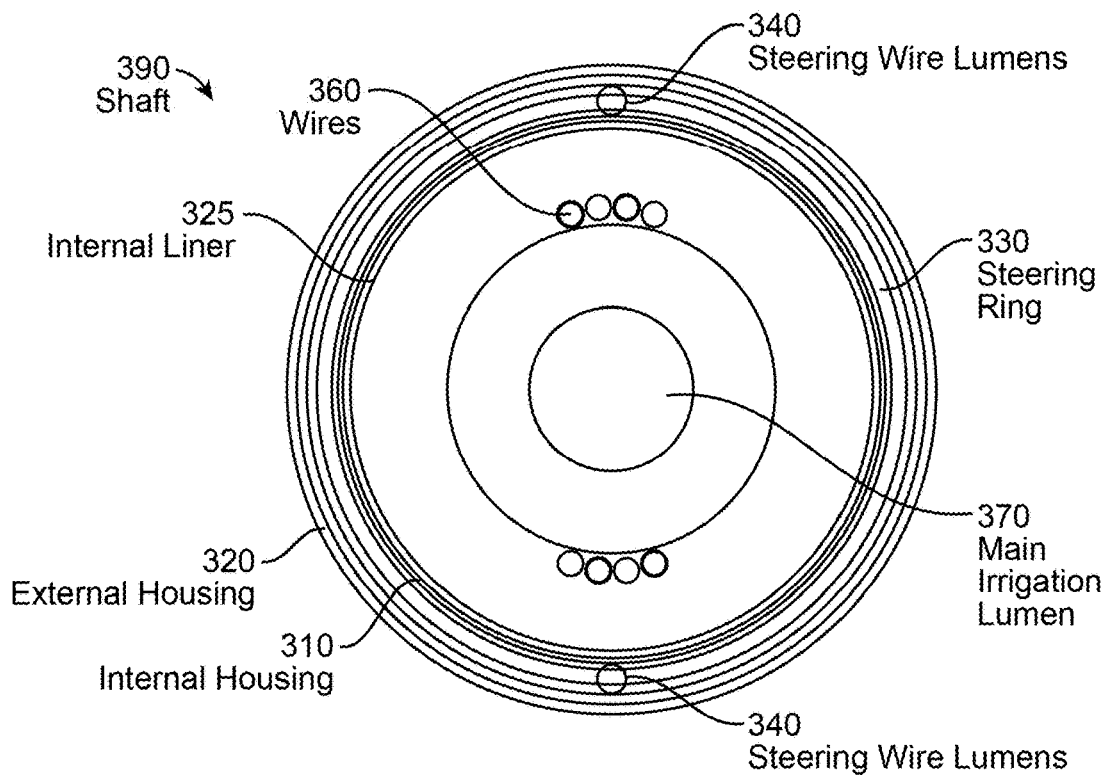
FIG. 3D illustrates a proximal cross-section view of a second shaft of the heart treatment device, according to one or more embodiments.
Figure 3E:
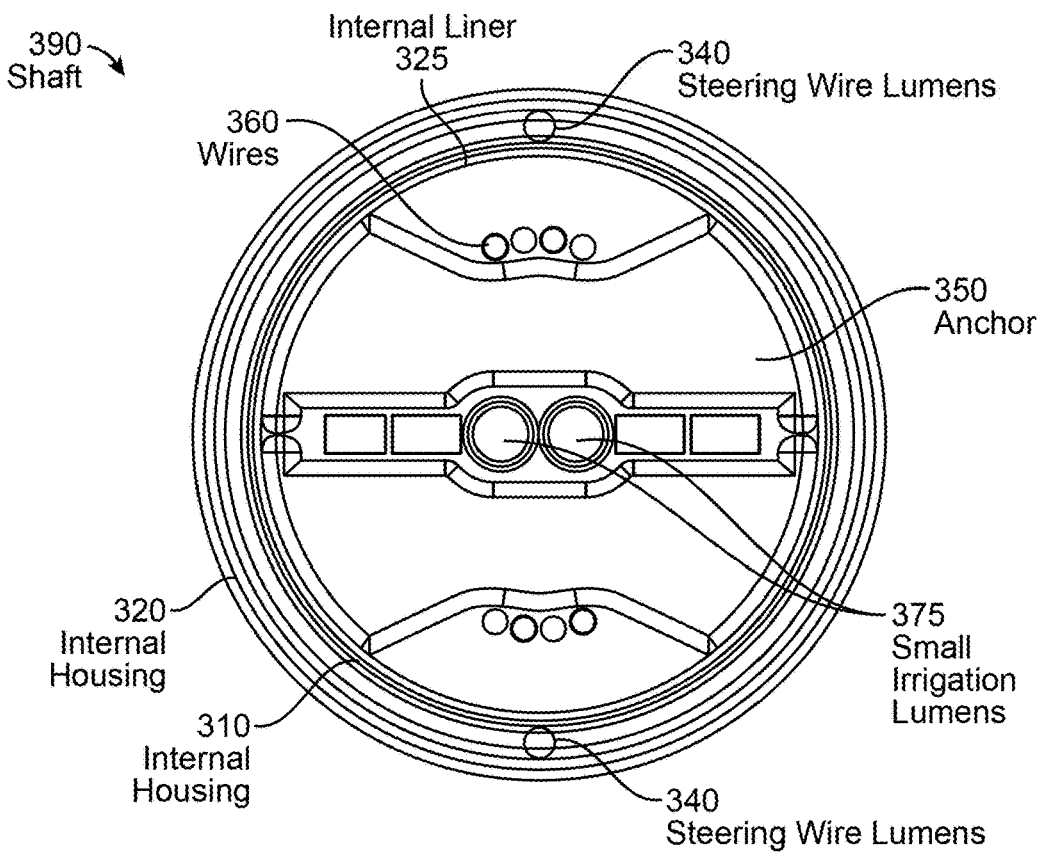
FIG. 3E illustrates a distal cross-section view of the second shaft, according to one or more embodiments.

FIGS. 3D & 3E illustrate cross-section views of a second shaft 390 that may be implemented in the heart treatment device 105, according to one or more embodiments. FIG. 3D illustrates a proximal cross-section view of the second shaft 390 of the heart treatment device, according to one or more embodiments. FIG. 3E illustrates a distal cross-section view of the shaft 390, according to one or more embodiments.

The shaft 390 comprises many similar components to the shaft 300. In particular, the shaft 390 comprises, among other components, an internal housing 310, an external housing 320, an internal liner 325, a steering ring 330, steering wire lumens 340, an anchor 395, conductor wires 360, and irrigation lumens. The anchor 350 of the shaft 390 is shaped differently than the anchor 350 of the shaft 300. The anchor 350 of the shaft 390 comprises two pieces that interface along two contact points towards the circumference of the shaft 390. The anchor 350 of the shaft 390 has a larger cross-section area in proportion to the cross-section area of the shaft 390 than the anchor 350 of the shaft 300. The thicker anchor 350 provides added strength and support. In the shaft 390, the wires are also dispersed in both halves of the shaft 390, the halves created based on the coupling contact points of the two pieces of the anchor 350. Also the shaft 390 comprises two small irrigation lumens 375 that split from the main irrigation lumen 370 towards a proximal end of the shaft 390.

Figure 4A:
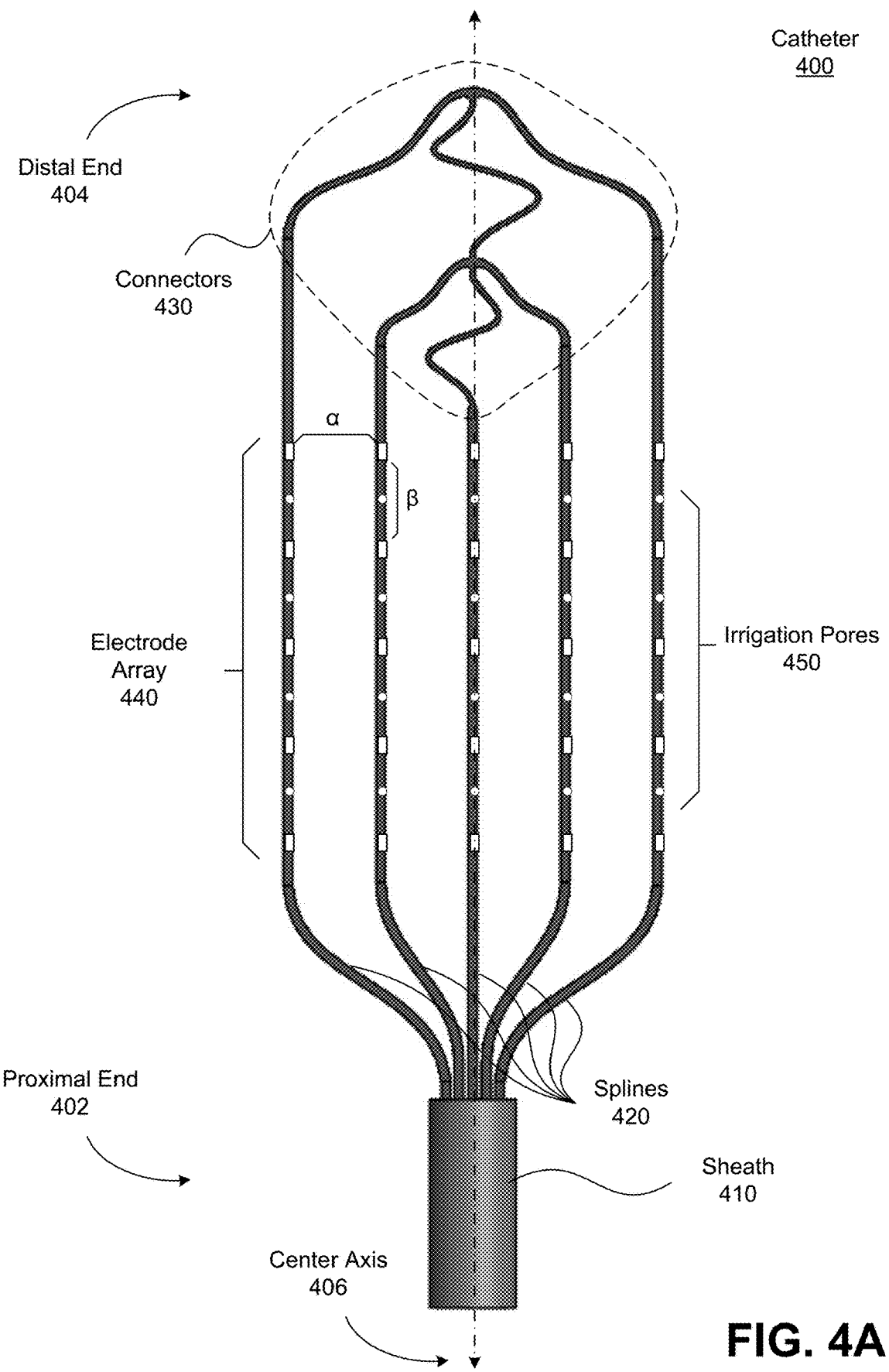
FIG. 4A illustrates a top view of a first catheter that may be implemented in the heart treatment device, according to one or more embodiments.

FIG. 4A illustrates a top view of a first catheter 400 that may be implemented in the heart treatment device 105, according to one or more embodiments. The catheter 400 is an embodiment of the catheter 155. The catheter 400 is shown in an expanded state, wherein the catheter 400 is unsheathed from the sheath 410, i.e., extended away from the sheath 410. The catheter 400 comprises, among other components, a plurality of splines 420, a plurality of connectors 430, an electrode array 440, and irrigation pores 450. Other sensors in some embodiments include temperature sensors, force-sensing elements, photoelectric sensors to identify changes to tissue composition prior to and during ablation to verify treatment effect. For some embodiments, magnets can be added to enable positional sensing within the body for some mapping systems. Other sensors that will be apparent to one skilled in the art. In one or more embodiments, the sheath 410 is a component of the heart treatment device 105. However, in other embodiments, the sheath 410 may also be an external component, such that the catheter 400 and the shaft 150 are inserted into the sheath 410.

For discussion purposes, a proximal end 402 of the catheter 400 is towards the shaft 150 and the handle 145, whereas a distal end 404 of the catheter 400 is opposite from the proximal end 402. A center axis 406 runs through the center of the sheath 410 and the shaft 150 from the proximal end 402 to the distal end 404.

The sheath 410 is configured to store the catheter 400 in a compact state. The sheath 410 is a substantially rigid component that can hold the catheter 400 in the compact state as it is introduced into the blood vessel. The rigidity of the sheath 410 must be sufficient to avoid elastic deformation when the catheter 400 is held in the compact state and applying an outward force against the sheath 410 e.g., in a radial direction away from the center axis 406. In one or more embodiments, the sheath 410 is substantially of a cylindrical shape capable of fitting around the shaft 150. As such, the sheath 410 can translate along the center axis 406 relative to the shaft 150. The catheter 400 extends beyond the sheath 410 to transition into the expanded state and retracts into the sheath 410 to transition into the compact state (also referred to as the compact state). In some embodiments, the catheter 400 is moved relative to the sheath 410 by the handle 145. In other embodiments, the sheath 410 is moved relative to the catheter 400 by the handle 145.

The sheath 410 can be straight or have varying degrees of curvature at the distal end to facilitate maneuverability to regions within the organ. In one embodiment, the sheath has a tapered shape at the distal end to facilitate extension and retraction of the catheter 400. Some sheaths have varying "deflectable" curvatures. Collapse of the catheter within the sheath should be smooth without undue force. It also should not inadvertently trap tissue as it is pulled into the sheath. The closed design of the electrode array catheter in many embodiments prevents such events. Catheter shapes in other embodiments may include the ability to deliberately 'attach' to structures for stability, such as for ablation of the papillary muscles which is typically limited by catheter slippage.

In embodiments where the sheath 410 is a separate component from the catheter 400, an introducer tool may be implemented for compacting the catheter 400 to the compact state for insertion into the sheath 410. The introducer tool may have a tapered form that aids in transitioning the catheter 400 into its compact state. The introducer tool may also couple to the sheath 410 at a proximal end that remains external to the patient during the procedure. A physician inserts the catheter 400 through the introducer tool to transition the catheter into its compact state and into the sheath 410. The catheter 400 in its compact state can be translocated through the sheath 410 to a distal end that is guided to the treatment site.

The plurality of splines 420 provide a structure for contacting the heart tissue with the catheter 155. The splines 420 are flexible and insulative, e.g., formed with Nitinol having an insulative coating composed of polyether block amide (PEBA). In other embodiments, other flexible materials, that are also safe for invasive procedures, may be used. Other example materials that may be used for the splines include, but are not limited to, alloys composed of Ti—Nb, Ti—Mo, Ti—V, other Beta titanium alloys, Cu—Zn—Al, other Beta brass alloys, Cu—Al—Ni, Cu—Al—Be, other bronzes, Fe—Mn—Si, Fe—Co—Cr, other iron-based alloys, Ni—Al, In—Tl, U—Nb, Au—Cd, Ag—Cd, Ru—Ta, other alloys of sufficient flexibility and elasticity (atomic symbols used herein). Other example insulative materials that may be used include, but are not limited to, polyimides, polyamide-imides, PTFE, other high performance plastics, etc. The flexibility allows for the splines to flex and conform to non-planar topography of the heart tissue. The flexibility of the splines 420 helps in the extension and retraction from the sheath 410. The splines 420 include a substantially linear portion where the electrodes of the electrode array 440 are disposed. Towards the proximal end 402, one or more splines include a curved portion that connect the respective linear portion extended beyond the sheath 410 and another linear portion that remains within the sheath 410. The curved portion aids in the expansion and the collapse of the catheter 400, which will be described further in conjunction with FIG. 4C. Within the plurality of splines 420 are wiring and irrigant fluid channels, which connect to the electrode array 440 and the irrigation pores 450. In the expanded state, the plurality of splines 420 are spaced apart. As shown, the splines 420 are evenly spaced apart; however, other embodiments may utilize variation in the spacing between adjacent splines.

The connectors 430 connect the splines 420 to ensure the splines 420 remain in a planar orientation. The connectors 430 are also flexible and insulative, e.g., formed with Nitinol with an insulative coating. Each connector includes one or more bends in its shape. The one or more bends in a connector are capable of storing energy when deformed, wherein that energy is used to separate the splines when the catheter 400 is unsheathed, i.e., extended from the sheath 410. As the catheter 400 is retracted into the sheath 410 (into a compact state, also referred to as a compact state), the one or more bends of the connectors are deformed storing potential energy in the bends. Each bend has a particular curvature. As the curvature is changed by deformation, i.e., increased or decreased, the material stores both compressive and tensile potential energy. As the catheter 400 is extended from the sheath 410 (into an expanded state), the stored potential energy causes the connectors 430 to return to a default shape where the splines 420 are spaced apart. In one or more embodiments, the splines 420 and the connectors 430 may be monolithic, i.e., formed from one contiguous piece of material.

The electrode array 440 is disposed on the splines 420. The electrode array in preferred embodiments should be large enough to cover critical areas for biological rhythm disorders, yet small enough so that a practical number of electrodes can provide high-spatial resolution recordings. The size of this intracardiac system is personalized to the biological rhythm disorder.

As shown in FIG. 4A, the array may be a substantially rectangular array defined by a repeating rectangular grid with dimensions α×β, wherein α is the dimension perpendicular to the center axis 406 and β is the dimension parallel to the center axis 406, and wherein an electrode is placed at each vertex of the rectangular pattern. As a numerical example, there is a total of twenty-five electrodes in the electrode array, with five electrodes disposed on each of five splines, with rectangular grid dimensions: α is 2 mm and β is 2 mm.

The range of electrodes for an intracardiac system for heart rhythm applications is typically 4 to 128. In the embodiment in FIG. 4, the mapping electrode array (or 'waffle', or 'spade' or 'grid') is about 2 cm×2 cm (W×L) (range 1 cm×1 cm to 5 cm×5 cm). A typical arrangement for mapping AF would be 16-64 electrodes in an area of 2 cm$^2$ to 16 cm$^2$. A typical arrangement for mapping gaps in a pulmonary vein encircling line would be 4-16 electrodes in an area of 1-2 cm$^2$. A typical arrangement for mapping critical regions for ventricular tachycardia would be 9-25 electrodes in an area of 2-4 cm$^2$. The size of this electrode array can also be personalized to the profile of the patient, using tools such as machine learning calibrated to patients of similar clinical type and data.

FIG. 4A illustrates 5×5 electrodes in a uniform grid. The choice of an odd number of electrodes along each axis enables the device to provide a 'center point' with peripheral electrodes in a symmetrical design to map centrifugal activation from a focus or uniform circular re-entry around this central point. Configurations with 4×4 electrode combinations are less well suited for this specific application but have other potential applications. Other even combinations of electrodes require an off-center electrode at the center of rotation or focal activity, with an asymmetry of surrounding electrodes which is wasteful of size and may introduce difficulties of recording from practical clinical electrophysiological amplifiers that have a fixed number of recording channels.

The size of the electrode array will vary with the organ being treated. The size may be smaller for a device in the brain, where small size is at a premium to avoid destruction of tissue, than for a device in the heart, where larger mapping and ablation areas are sometimes needed. The therapy tool contacts the organ by conforming to its surface at a plurality of locations.

In other embodiments, the array may be imperfect, i.e., the array is not formed by repetition of one grid. For example, the spacing between adjacent splines 420 can vary or the spacing between electrodes on a single spline can vary. Typically, the number of channels that can be sensed in a patient is limited by the recording amplifier. The advantage of a variably spaced array is this fixed number of electrodes can be distributed with a high-spatial solution in a central cluster to define ablation patterns, yet with peripheral electrodes to enhance directional navigation (for instance "move catheter left") In one or more embodiments, the characteristics of the electrode array 440, i.e., placement of each electrode within the electrode array 440, can be tailored and optimized for a particular patient, as will be further described in FIG. 16-17.

Each electrode of the electrode array 440 is capable of sensing electrical signals of the heart tissue and for delivering ablation energy to the heart tissue. Each electrode is formed from a conductive material coupled circumferentially to the respective spline that the electrode is disposed on. Example materials that can be used to form the electrodes include, but are not limited to, gold, platinum, metal alloys containing gold, metal alloys containing platinum, gold-plated copper, other conductive metals, other conductive metal alloys, etc. In one or more embodiments, the electrode material is also safe for use in blood. For example, the size of each electrode in FIG. 4 is on the order of 0.8 mm diameter (it is a cylinder), measured along the center axis 406 and 1 mm along the spline. This small electrode sizing provides for very-high-resolution sensing by the electrode array 440. It is well understood that the size of a measurement device (in this case, an electrode of the array 440) limits the measurement resolution that can be achieved by the measurement device.

Coupled to each electrode is a wire that transfers electrical energy from the handle 145 to the electrode. The wires connected to the electrodes may be substantially large in diameter to transfer the required ablation energy from the generator 115 to the electrodes. This includes the ablation energy required for pulsed field ablation or other high energy applications. In one or more embodiments, the wires are formed from copper. Other example wire materials include gold, platinum, silver, other conductive metals, other conductive metal alloys, etc. The wires connected to the electrodes of the electrode array 440 may be insulated to prevent unwanted discharge of electrical energy that could cause damage to tissue not being treated or damage to the components of the heart treatment device 105.

The inventive process includes the novel ability to provide deep and durable tissue modification or destruction ("ablation") through small electrodes which are also well suited to sense at high resolution. This enables very precise and specific ablation patterns to be delivered in regular, irregular and personalized shapes tailored to the specific rhythm disturbance in that patient. The ability to deliver ablation through these small electrodes is attributable to the materials used in the inventive process and the energy waveform approaches.

In a sensing configuration, each electrode can be configured to measure electrical signals and to provide the electrical signals to the control system 110. The electrical signals collected by each electrode can include: a voltage signal, a current signal, an impedance signal, another electrical parameter, etc. The spacing between adjacent electrodes in the electrode array 440 can be sufficiently small so as to provide high-resolution sensing of the electrical activity of the heart tissue. The electrical signals are used by the control system 110 to determine guidance instructions for movement of the catheter 400 towards a source region that requires ablation therapy.

In an ablation configuration, each electrode can be configured to deliver ablation energy to heart tissue. The ablation energy is in the form of electrical energy received from the generator 115. As noted above, the ablation energy may be tailored, e.g., at a particular frequency or wavelength, with a particular waveform, over a particular duration. This includes common 'moderate power, moderate duration' energy such as 30-50 W at 15-60 seconds, as well as 'high power short duration' energy such as 50-90 W at 5-15 seconds. This also includes very high powers associated with pulsed field ablation (to cause irreversible electroporation). Each electrode, in the ablation configuration, is capable of achieving >3 mm in depth of delivery of ablation energy. As each electrode is addressable independently, the electrode array 440 is capable of delivering ablation energy in a variety of ablation patterns that can be tailored to each critical region for the biological rhythm disorder identified by the control system 110. This is advantageous as the catheter 400 need not perform multiple ablation steps to achieve a particular pattern, which would otherwise be the case with singular ablation electrode catheters or even linear ablation catheters. For example, to create a cross pattern with a linear ablation catheter, the linear ablation catheter would need to perform at least two steps to ablate the two arms of the cross pattern with the additional movement necessary to change positions of the catheter. However, the electrode array 440 of the catheter 400 could achieve the cross pattern by selectively addressing all the electrodes in the middle spline and the middle electrodes in the other splines. The electrode array 440 could thus ablate with the cross pattern in a single step, without needing to reposition the catheter 400. In this fashion a circular, arc shaped or other ablation configuration can be readily delivered depending on the physician selection for that biological rhythm disorder in that patient.

The irrigation pores 450 vent irrigant during an ablation procedure. The irrigation pores 450 are openings in the splines 420 which permit liquid irrigant to escape from the splines 420. The splines 420 thus can also operate as irrigant fluid channels. As shown in FIG. 4A, the irrigation pores 450 are disposed in between adjacent electrodes on a spline. Following the numerical example above, there is a total of twenty irrigation pores 450, with four irrigation pores 450 disposed on each spline of five splines, interlaced between the electrodes on each spline. The irrigation pores 450 can be both on the top side (in view from the top view) and on the bottom side (obscured from the top view), that is opposite the top side. In another example, there is a total of forty irrigation pores 450, twenty on the top side and twenty on the bottom side. In other embodiments, there can be additional or fewer irrigation pores then shown in FIG. 4A. For example, the ratio of irrigation pores to electrodes can range from 2:1 (two irrigation pores to each electrode) to 1:9 (one irrigation pore to nine electrodes). Venting irrigant during an ablation procedure is important to prevent searing of the tissue, the irrigant acts to spread the energy so that no region becomes too hot, thus searing the tissue. Prevention of tissue-searing allows for lengthier ablation procedures which can help achieve greater depth in delivery of ablation therapy and can also prevent scarring of the tissue. Irrigation pores can be independently addressable to limit the extent of fluid delivery, for instance in patients with existing heart failure. Typically, for safety, all irrigation pores will be used simultaneously. The placement of the irrigation pores 450 in proximity to (e.g., within a couple of millimeters) to the electrodes of the electrode array 440 provide sufficient irrigant to prevent tissue char, thereby enabling the potential for delivering the ablation energy in a variety of ablation patterns.

In one or more embodiments, one or more temperature sensors may be implemented on the catheter 400. The temperature sensors measure a temperature of tissue in contact with the temperature sensors. Temperature sensors can be near multiple electrodes, on each spline or in other configurations. In one or more implementations, the temperature sensors measure a change in electrical resistance, electrical voltage, or another electrical metric within a circuitry having a temperature-sensitive material. Example temperature sensors include a resistance temperature detector, a thermocouple, a thermistor, etc. In other embodiments, non-contact temperature sensors may be used, e.g., infrared photoelectric sensor.

In one or more embodiments, one or more force-sensing elements may be implemented on the catheter 400. The force-sensing elements measure a contact force between the catheter 400 and the tissue. The measured contact force can be used to verify contact between the catheter 400 and the tissue during sensing and/or ablation. The force-sensing elements may be piezoelectric sensors, surface capacitance sensors, etc.

In one or more embodiments, one or more photoelectric sensors may be implemented on the catheter 400. The photoelectric sensors may be used to identify changes to tissue composition prior to, during, or after ablation. The photoelectric sensors may also be infrared sensitive to determine a temperature of the tissue.

Figure 4B:
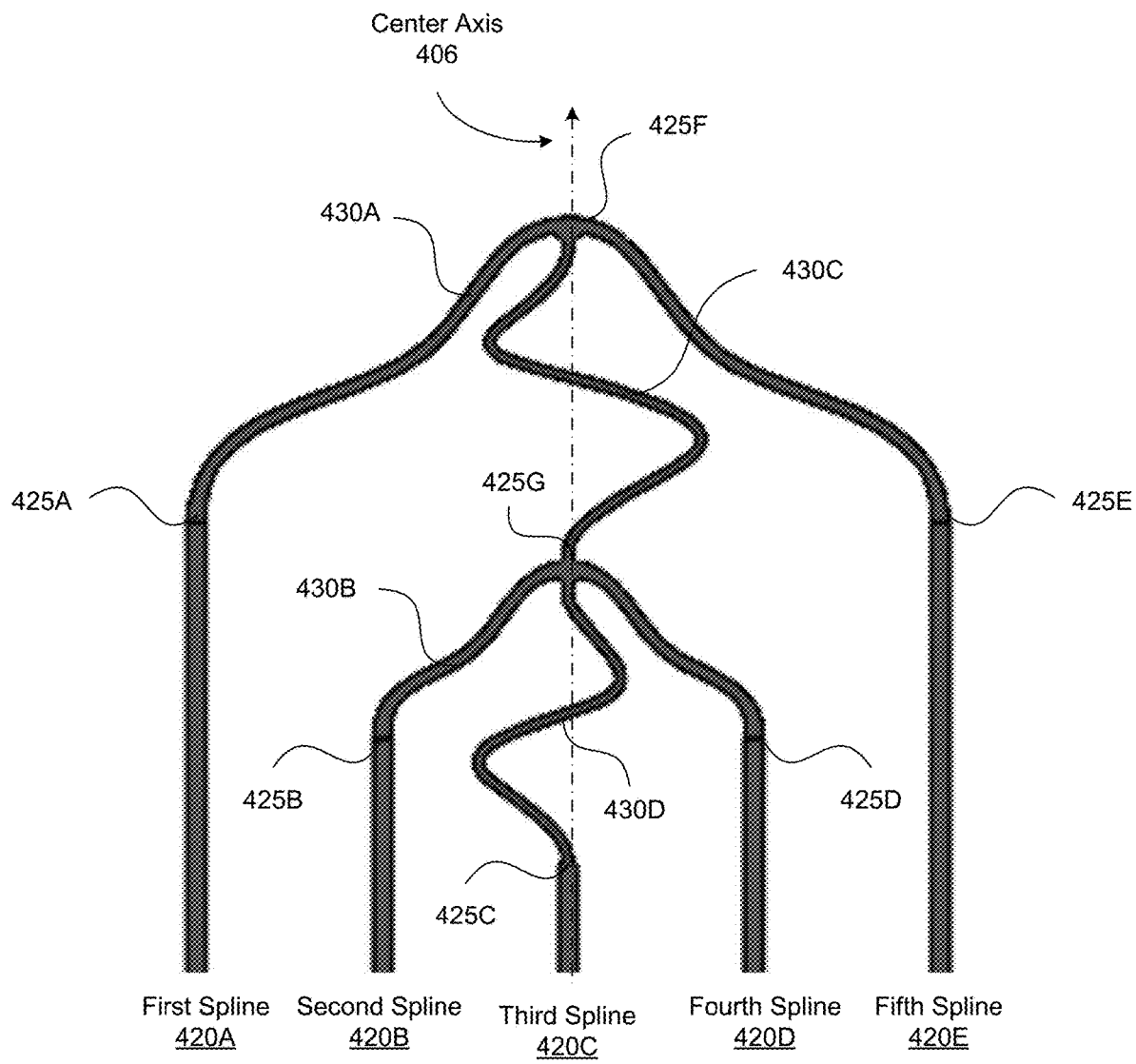
FIG. 4B illustrates an expanded view of the first catheter of FIG. 4A, according to one or more embodiments.

FIG. 4B illustrates an expanded view of a distal end of the first catheter 400 of FIG. 4A, according to one or more embodiments.

The splines 420 include a first spline 420A, a second spline 420B, a third spline 420C, a fourth spline 420D, and a fifth spline 420E. The third spline 420C is aligned with the center axis 406 of the shaft 150, also referred to as the middle spline.

The first spline 420A and the fifth spline 420E are connected by connector 430A to form an outer loop. Connector 430A is connected to a distal end of the first spline 420A at joint 425A. Connector 430A is also connected to a distal end of the fifth spline 420E at joint 425E. The second spline 420B and the fourth spline 420D are connected by connector 430B to form an inner loop. Connector 430B is connected to a distal end of the second spline 420B at joint 425B. Connector 430B is also connected to a distal end of the fourth spline 420D at joint 425D. The outer loop is connected to the inner loop with connector 430C, which attaches to connector 430A at joint 425F and to connector 430B at joint 425G. The inner loop is connected to the third spline 420C with connector 430D, which attaches to connector 430B at joint 425G and to the third spline 420C at joint 425C.

Connector 430A and connector 430B have a rounded V-shape. Connector 430A connects a distal end of the first spline 420A and a distal end of the fifth spline 420E. If starting from the first spline 420A, connector 430A extends diagonally towards a distal direction, away from the shaft 150, and towards the center axis 406. Upon crossing the center axis 406, connector 430 extends diagonally towards a proximal direction, towards the shaft 150, and away from the center axis 406 to the distal end of the fifth spline 420E. The V-shaped bend intersects the center axis 406. The V-shaped bend is rounded, i.e., not pointed, so as to decrease chances of puncturing tissue. Joint 425A and joint 425E are also bends of connector 430A. Connector 430B follows a similar pathway as connector 430A, but from the second spline 420B to the fourth spline 420D. In sum, connector 430B has bends at joint 425B, joint 425D, and the V-shaped bend at joint 425G.

Connector 430C and connector 430D have a substantially sinusoidal shape. Between joint 425F and joint 425G, connector 430C has a single-wave sinusoidal shape along the center axis 406, with one peak and one trough. The peak and the trough serve as two bends in connector 430C. Connector 430D also has a sinusoidal shape between joint 425G and joint 425C, with one peak and one trough. The peak and the trough serve as two bends in connector 430D. Connector 430C tethers the outer loop, comprised of the first spline 420A, connector 430A, and the fifth spline 420E, to the inner loop, comprised of the second spline 420B, connector 430B, and the fourth spline 420D. Tethering the inner loop and the outer loop together with connector 430C ensures the inner loop and the outer loop stay in the same plane, in the expanded state. Connector 430D tethers the inner loop to the third spline 420C. Tethering the inner loop to the middle spline ensures the inner loop and the middle spline stay in the same plane, in the expanded state. With both connector 430C and connector 430D, the splines 420 are ensured to be substantially planar when in the expanded state.

In the expanded state of the catheter 400, the connectors are in a minimal energy state. When the catheter 400 transitions to the compact state, the first spline 420A and the fifth spline 425E move towards the center axis 406, which pushes joint 425A and joint 425E towards the center axis and joint 425F in a distal direction, away from the shaft 150. The movement of joint 425A and joint 425E towards the center axis 406 increases the curvature in the bend at joint 425F, placing connector 430A in a high energy state. Similarly, when transitioning to the compact state, connector 430B transitions to a high energy state as the curvature in its bend increases. As the first spline 420A, the second spline 420B, the fourth spline 420D, and the fifth spline 420E move towards the center axis 406, joint 425F and joint 425G move away from joint 425C. In particular, a distance between joint 425F and joint 425G is increased, decreasing the curvature in the bends of connector 430C. The decreasing curvature places connector 430C in a high energy state. Similarly, as a distance between joint 425G and joint 425C increases, there is a decrease in the curvature in the bends of connector 430D, placing connector 430D in a high energy state. As the catheter 400 is unsheathed, i.e., extended from the sheath, the stored energy in the connectors 430 is released, transitioning the connectors 430 into their minimal energy states. An animated sequence of the transition between the expanded state and the compact state is shown in FIG. 4C.

Figure 4C:
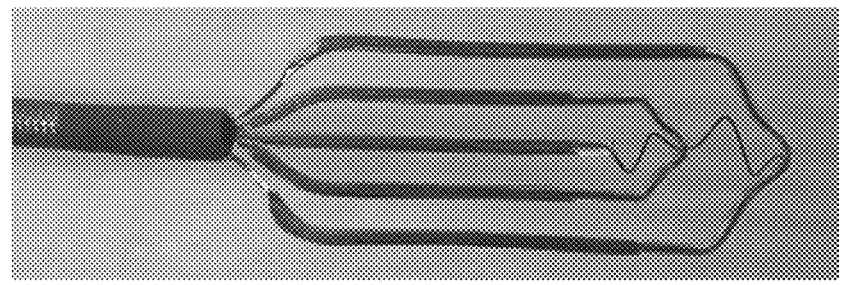
FIG. 4C illustrates withdrawal of the first catheter into a sheath or holding tube, according to one or more embodiments.
Figure 4C:
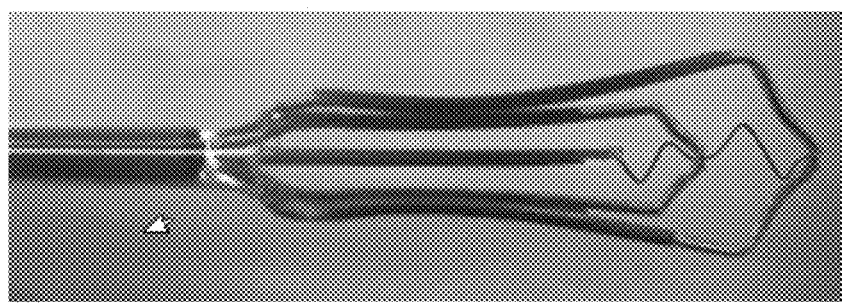
Figure 4C:
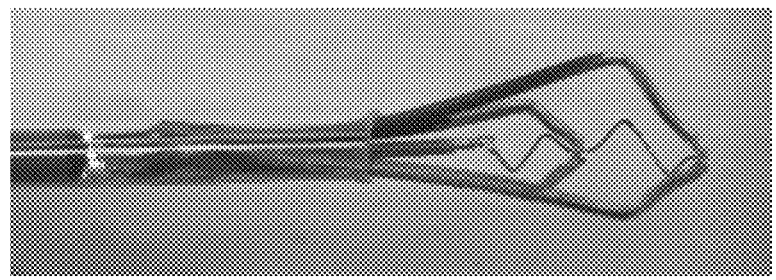
Figure 4C:
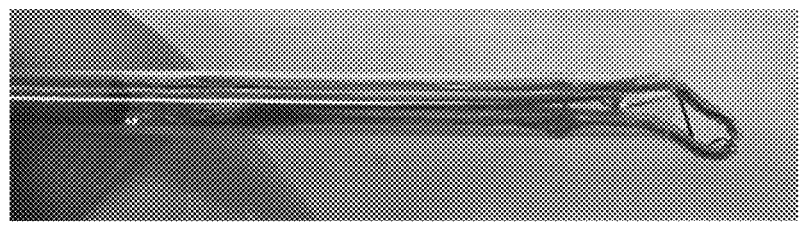
Figure 4C:
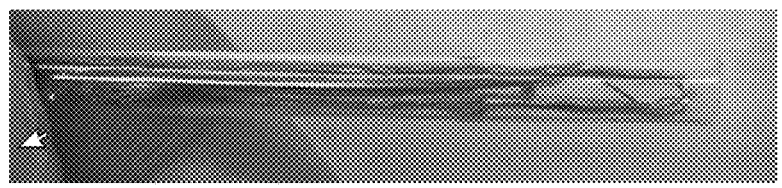

FIG. 4C illustrates a transition between an expanded state and a compact state of the first catheter 400 of FIG. 4A, according to one or more embodiments. In this animated sequence, the catheter 400 is retracted into the sheath 410, which is transparent for viewability of the catheter 400.

At step 462, the catheter 400 is in an expanded state. The connectors 430 are in a minimal energy state.

At step 464, the sheath 410 comes in contact with the splines 420 at a proximal end of the catheter 400. The sheath 410 applies a force on the outer splines (420A and 420E in FIG. 4B), such that the outer splines are touching the inner splines (420B and 420D in FIG. 4B). The curved portion of the outer splines are deformed, i.e., the curvature of the curved portion has been decreased, thereby energy in a high energy state.

At step 466, a sheath approaches a halfway point, wherein half of the catheter 400 is held within the sheath 410. The inner splines (420B and 420D in FIG. 4B) are also pulled in, such that all the splines, towards the proximal end 402, are proximate to the center axis 406. The curved portion of the inner splines are also deformed, i.e., the curvature of the curved portion has been decreased, thereby storing energy in a high energy state.

At step 468, the sheath 410 approaches a three-quarters point, wherein three-quarters of the catheter 400 is held within the sheath 410. The sinusoidal-shaped connector (430D in FIG. 4B) attached to the middle spline (420A in FIG. 4B) is now stretched out within the sheath 410.

At step 470, the sheath 410 fully envelops the catheter 400, wherein the catheter 400 is in the compact state. The second sinusoidal-shaped connector (430C in FIG. 4B) furthest towards the distal end of the catheter 400 is also stretched out in the sheath 410. In addition, some or all of the other bends in the connectors 430 are deformed and in a high energy state.

In the compact state, the catheter 400 and the shaft 150 can be inserted via an access point (e.g., a vascular access point) and steered to the tissue (e.g., the heart tissue). At the tissue, the catheter 400 can be deployed to the expanded state for treatment of a heart rhythm disorder. Once treatment is complete, the catheter 400 can be retracted to the compact state for removal from the patient.

Transitioning back to the expanded state, as the catheter 400 extends beyond the sheath, the bends of the connectors 430 and/or the curved portions of some of the splines 420 want to relax and return to their minimal energy state. As the sheath allows for the catheter 400 to expand, the stored energy in the connectors 430 expands and spaces out the splines 420, back to the expanded state shown in step 462.

Ablation in a preclinical model is shown in FIG. 4D. The catheter was passed through femoral veins into the right atrium of a 25 kg pig under general anesthesia. Segments of 2×2 electrodes were ablated while titrating power and duration. A selected experiment is shown. The left panel shows gross pathology on the right atrium for an area >1 cm×1 cm ablated, as expected slightly larger than the physical electrode subarray of 3.6 mm (0.8 mm diameter, with 3.0 mm center to center spacing) in one axis and 4.0 mm in the orthogonal axis (0.8 mm diameter, with 3.0 mm center to center spacing). The right panel shows full transmural ablation from this configuration, indicating depth >3 mm. Power of 40-100 W across 4 electrodes for 30 seconds can achieve varying depths of penetration, depending on irrigation. Irrigation prevents charring and minimizes safety issues from ablation.

Figure 5A:
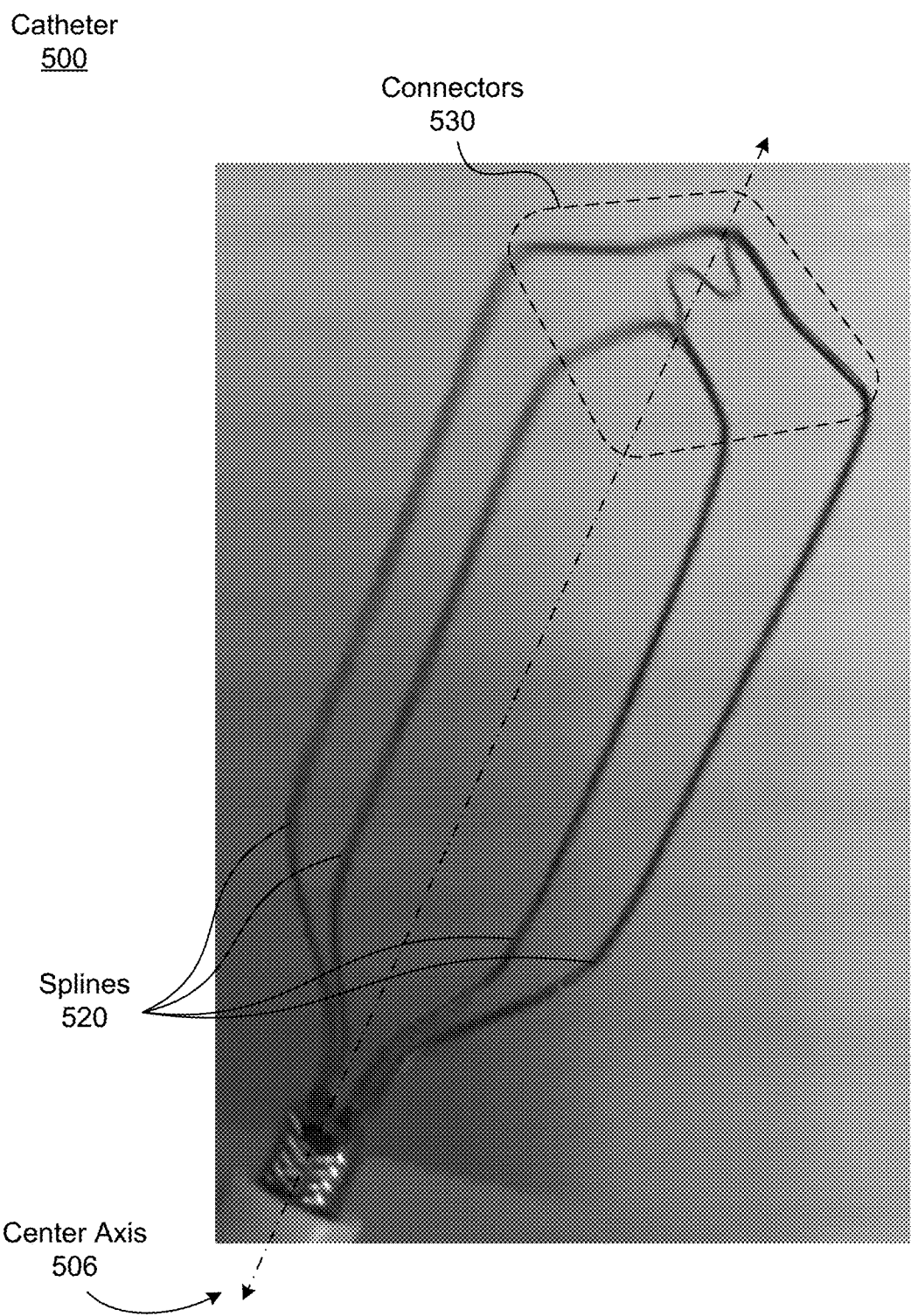
FIG. 5A illustrates a top view of a second catheter that may be implemented in the heart treatment device, according to one or more embodiments.

FIG. 5A illustrates a top view of a second catheter 500 that may be implemented in the heart treatment device 105, according to one or more embodiments. The catheter 500 is shown in an expanded state, wherein the catheter 500 is unsheathed. The catheter 500 comprises, among other components, a plurality of splines 520 and a plurality of connectors 530. The plurality of splines 520 is an embodiment of the plurality of splines 420, and the plurality of connectors 530 is an embodiment of the plurality of connectors 430. The catheter 500 also comprises an electrode array and a plurality of irrigation pores, though not presently shown, which may be an embodiment of the electrode array 440 and the plurality of irrigation pores 450 on the catheter 400 in FIG. 4. Various other sensors and/or components described under catheter 400 may also be implemented.

In the catheter 500, the splines 520 include four splines. The splines 520 of the catheter 500 are similar to the splines 420 but omitting the middle spline 420C. Similarly, the connectors 530 are similar to the connectors 430 but omitting connector 430D connecting the middle spline 420C to other connectors.

The electrode array and the irrigation pores for the catheter 500 are disposed on the splines 520. For numerical examples, the electrode array of the catheter 500 may include twenty electrodes, with five electrodes on each of the four splines. In one or more embodiments, the splines 520 may be arranged to be evenly spaced between adjacent splines. In other embodiments, the splines 520 may have different spacing between adjacent splines. The irrigation pores are also disposed on the splines 520. The irrigation pores, like the irrigation pores 450, may be disposed between adjacent electrodes on a spline.

Figure 5B:
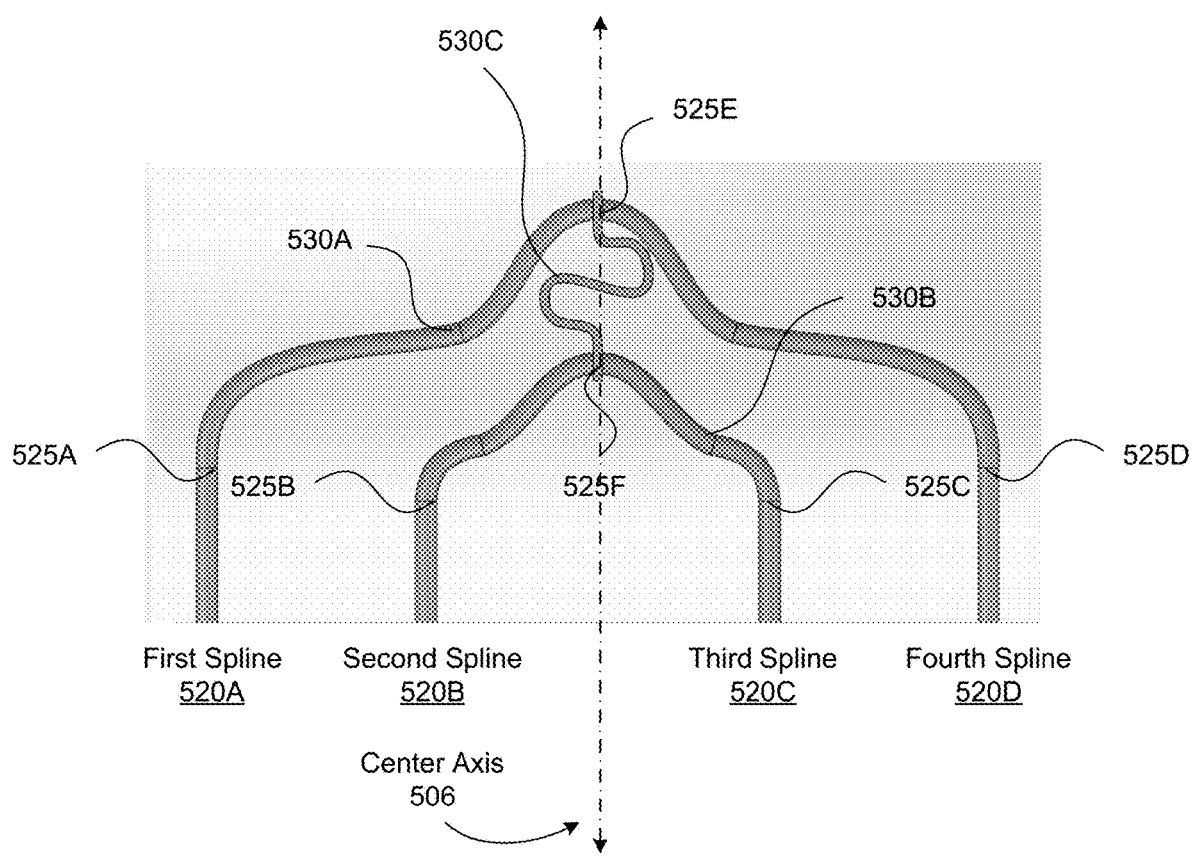
FIG. 5B illustrates an expanded view of the second catheter of FIG. 5A, according to one or more embodiments.

FIG. 5B illustrates an expanded view of a distal end of the second catheter 500 of FIG. 5A, according to one or more embodiments.

The splines 520 include a first spline 520A, a second spline 520B, a third spline 520C, and a fourth spline 520D. No spline is disposed along the center axis. The second spline 520B and the third spline 530C are the inner splines, and the first spline 520A and the fourth spline 520D are the outer splines.

The outer splines (first spline 520A and fourth spline 520D) are connected by connector 530A to form an outer loop. Connector 530A is connected to a distal end of the first spline 520A at joint 525A. Connector 530A is also connected to a distal end of the fourth spline 520D at joint 525D. The second spline 520B and the third spline 520C are connected by connector 530B to form an inner loop. Connector 530B is connected to a distal end of the second spline 520B at joint 525B. Connector 530B is also connected to a distal end of the third spline 520C at joint 525C. The outer loop is connected to the inner loop with connector 530C, which attaches to connector 530A at joint 525E and to connector 530B at joint 525F.

Connector 530A and connector 530B have a rounded V-shape. Connector 530A connects a distal end of the first spline 520A and a distal end of the fourth spline 520D. If starting from the first spline 520A, connector 530A extends diagonally towards a distal direction, away from the shaft 150, and towards the center axis. Upon crossing the center axis, the connector 530 extends diagonally towards a proximal direction, towards the shaft 150, and away from the center axis to the distal end of the fourth spline 520D. The V-shaped bend intersects the center axis. The V-shaped bend is rounded, i.e., not pointed, so as to decrease chances of puncturing tissue. Joint 525A and joint 525D are also bends of connector 530A. Connector 530B follows a similar pathway as connector 530A, but from the second spline 520B to the third spline 520C. In sum, connector 530B has bends at joint 525B, joint 525C, and the V-shaped bend at joint 525F.

Connector 530C is substantially S-shaped. Between joint 525E and joint 525F, connector 530C has two linear portions aligned with the center axis and an S-shaped portion disposed between the two linear portions. The two linear portions attach to joint 525E and joint 525F. In sum, connector 530C comprises at least four bends. The bends of connector 530C are capable of storing energy when the curvatures of the bends are adjusted, either increased or decreased. The stored energy places connector 530C in a high energy state. The stored energy is capable of returning connector 530C to its form in its minimal energy state, as shown in FIG. 5B.

The 4-spline catheter provides the benefit of 'bracketing' larger regions where internal sensing would be of limited value, such as delineating a region of scar in the heart, or enclosing a focal or reentry region. Ablation can then be delivered to enclose the region quickly and efficiently, rather than ablating across regions which may not be needed (for instance if the center is scar). This increases the versatility of the approach.

Figure 5C:
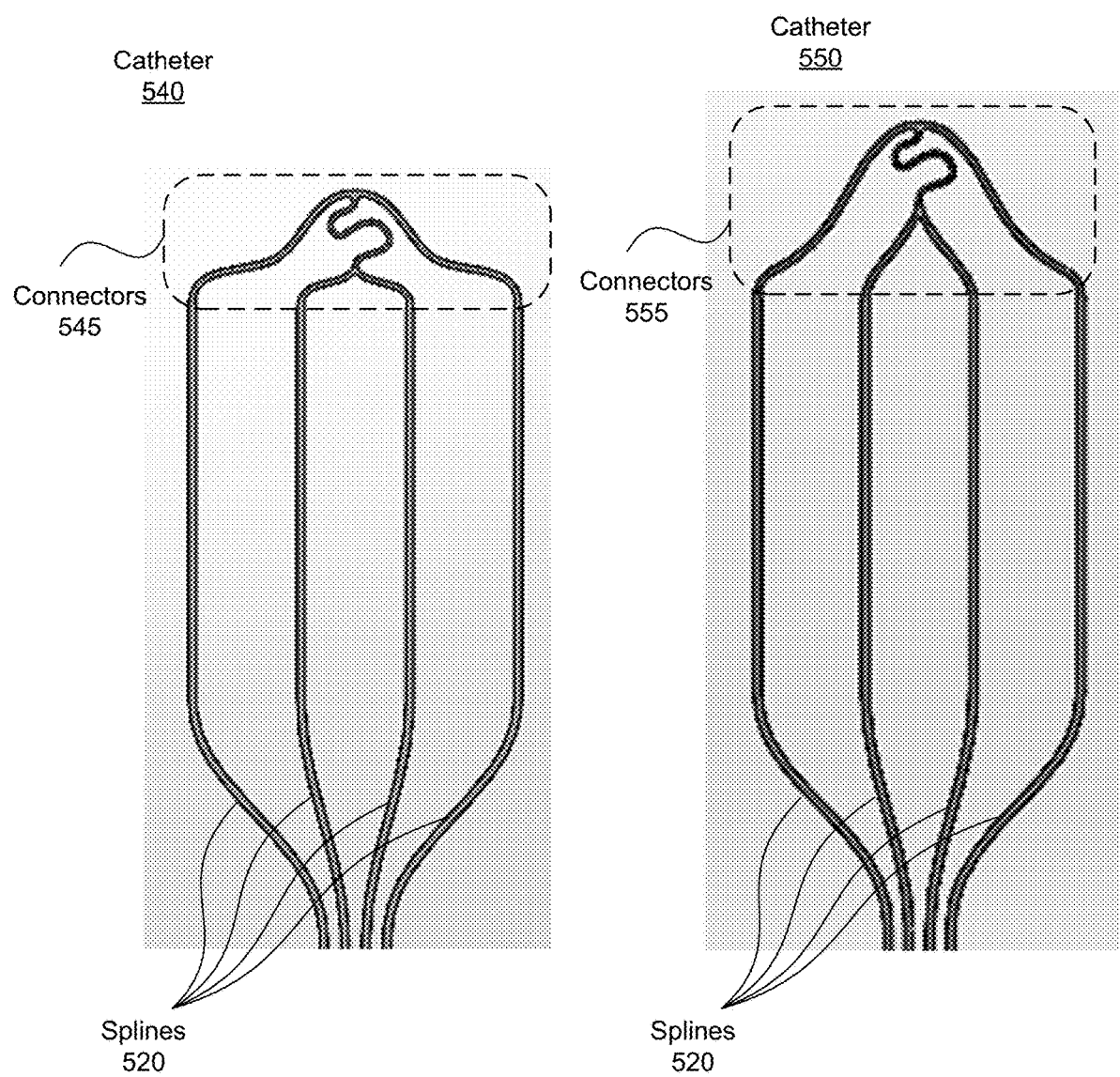
FIG. 5C illustrates a top view of a third and a fourth catheter that may be implemented in the heart treatment device, according to one or more embodiments.

FIG. 5C illustrates a top view of a third catheter 540 and a fourth catheter 550 that may be implemented in the heart treatment device 105, according to one or more embodiments. The third catheter 540 and the fourth catheter 550 are similar to the second catheter 500, having four splines 520 with the inner two splines connected with a connector and the outer two splines connected with a connector and with a third s-shaped connector connecting the outer loop and the inner loop. The third catheter 540 and the fourth catheter 550 may be monolithically formed, e.g., laser cutting a nitinol sheet. The third catheter 540's connectors 545 extend away from the proximal end less than the fourth catheter 550's connectors 555. Catheter 540 and catheter 550 have the same linear portion length of their splines, allowing for identical electrode spacing once electrodes are loaded. Catheter 550 has a slightly longer overall length from proximal end to distal end. Having a shorter length, the catheter 540 may have improved maneuverability compared to catheter 550. The catheter 550 has more gradual curves in the connectors forming the two loops, making collapsing and deploying of the catheter 550 more gradual compared to the catheter 540.

Figure 6:
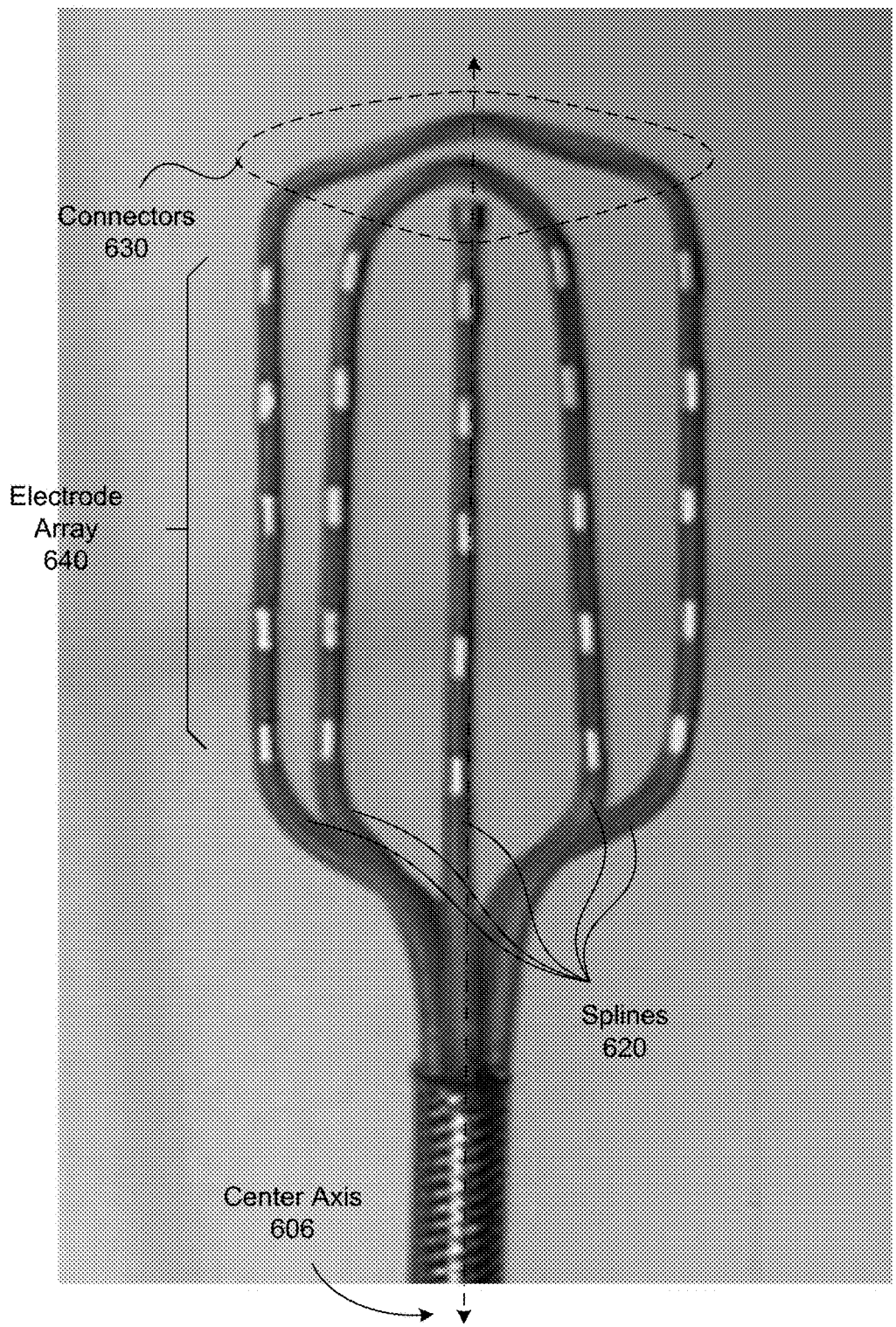
FIG. 6 illustrates a top view of a fifth catheter that may be implemented in the heart treatment device, according to one or more embodiments.

FIG. 6 illustrates a top view of a fifth catheter 600 that may be implemented in the heart treatment device 105, according to one or more embodiments. The catheter 600 is shown in an expanded state, wherein the catheter 600 is unsheathed or deployed. The catheter 600 comprises, among other components, a plurality of splines 620 and a plurality of connectors 630. The plurality of splines 620 is an embodiment of the plurality of splines 420, and the plurality of connectors 630 is an embodiment of the plurality of connectors 430. The catheter 600 also comprises an electrode array 640, which may be an embodiment of the electrode array 440. The catheter 600 may further include a plurality of irrigation pores (not shown), which may be an embodiment of the plurality of irrigation pores 450 on the catheter 400 in FIG. 4. Various other sensors and/or components described under catheter 400 may also be implemented.

The splines 620 are similar to the splines 420 of the catheter 400. The splines 620 include a total of 5 splines. A middle spline (similar to the third spline 420C) is aligned with the center axis of the shaft. Two inner splines disposed on either side of the middle spline (similar to the second spline 420B and the fourth spline 420D) are connected by a connector of the connectors 630 to form an inner loop. Two outer splines disposed on either side of the inner loop are connected by a connector of the connectors 630 to form an outer loop. In contrast to the catheter 400, the inner loop is not connected to the outer loop nor the middle spline.

As with the catheter 400, the bends of the connectors 630 and the curved portions of the splines 620 store energy when the catheter 600 is in a compact state, i.e., the catheter 600 is sheathed. As the catheter 600 is deployed, i.e., extended beyond the sheath, the stored energy is released causing the splines 620 to expand and to space apart in the expanded state.

Figure 7A:
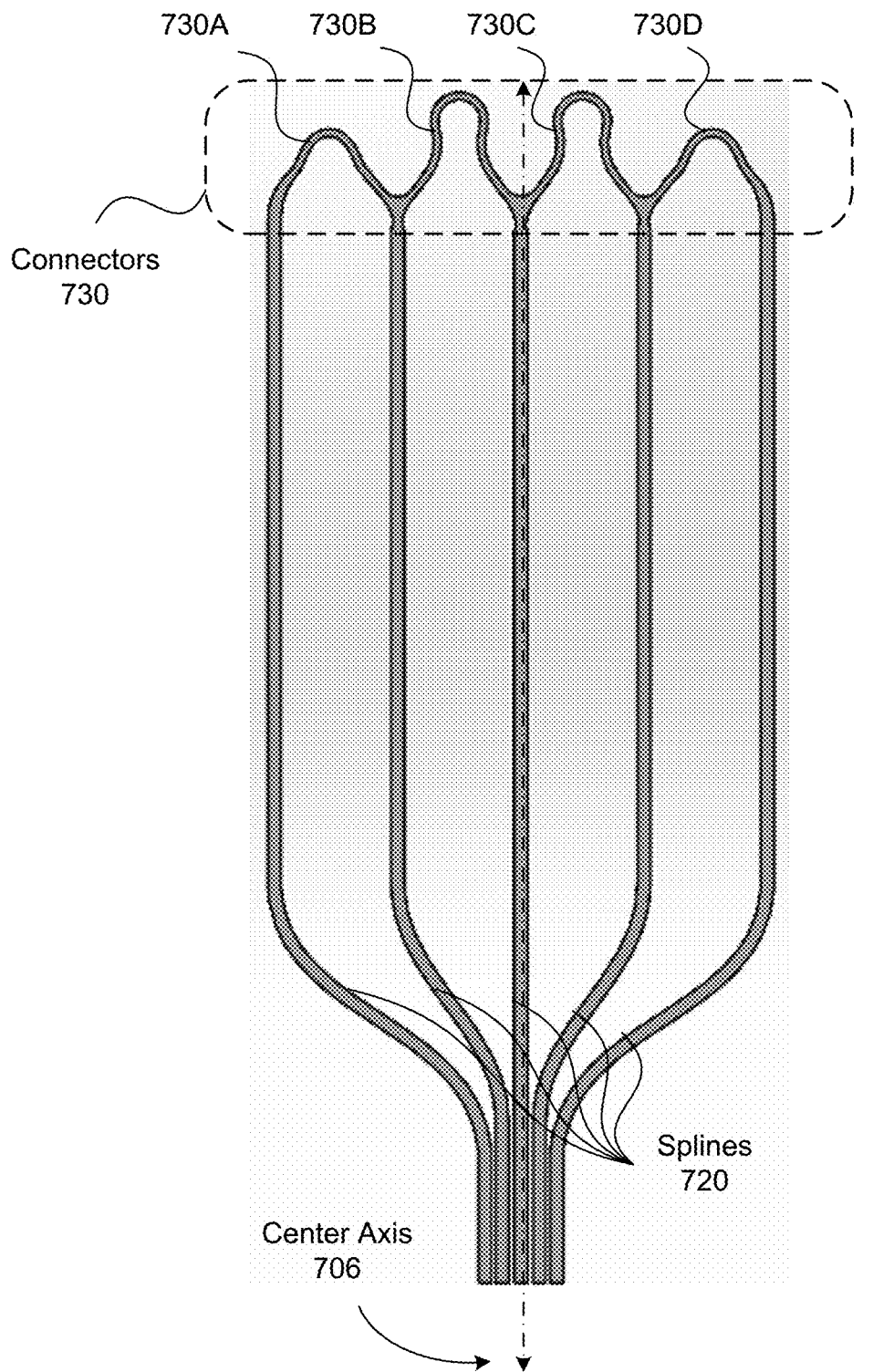
FIG. 7A illustrates a sixth catheter that may be implemented in the heart treatment device, according to one or more embodiments.

FIG. 7A illustrates a top view of a sixth catheter 700 that may be implemented in the heart treatment device 105, according to one or more embodiments. This catheter has a shorter overhang beyond the electrodes than some other designs, which may assist in maneuvering the catheter into small or tight spaces in the heart for diagnosis or therapy. The catheter 700 is shown in an expanded state, wherein the catheter 700 is unsheathed or deployed. The catheter 700 comprises, among other components, a plurality of splines 720 and a plurality of connectors 730. The plurality of splines 720 is an embodiment of the plurality of splines 420, and the plurality of connectors 730 is an embodiment of the plurality of connectors 430. The catheter 700 also comprises an electrode array (not shown), which may be an embodiment of the electrode array 440. The catheter 700 may further include a plurality of irrigation pores (not shown), which may be an embodiment of the plurality of irrigation pores 450. Various other sensors and/or components described under catheter 400 may also be implemented.

The catheter 700 includes five total splines in the splines 720. The five splines include a middle spline aligned with the center axis 706, two inner splines disposed on either side of the middle spline, and two outer splines disposed on either side of the inner splines (as shown in FIG. 7). The five splines are all substantially parallel to one another. In the embodiment of catheter 700, the splines 720 have linear portions, where the electrode array is disposed, that are substantially the same length. Put in another manner, the linear portions of the splines 720 extend to the same distance as measured along the center axis 706.

The catheter 700 includes four connectors in the connectors 730. Each connector connects distal ends of adjacent splines. Connector 730A connects the left outer spline to the left inner spline. Connector 730B connects the left inner spline to the middle spline. Connector 730C connects the middle spline to the right inner spline. Connector 730D connects the right inner spline to the right outer spline.

Connectors 730A, 730B, 730C, and 730D all have a U-shaped bend. Connector 730A and connector 730D have substantially the same length measured along the center axis 706. Connector 730B and connector 730C have substantially the same length measured along the center axis 706, which is greater than the lengths of connector 730A and connector 730D. The variable lengths of connectors in this design enables the catheter to slide past obstacles, rather than hitting them face on. Several different embodiments are possible which can be tailored for the biological rhythm disorder and organ structure in question.

Figure 7B:
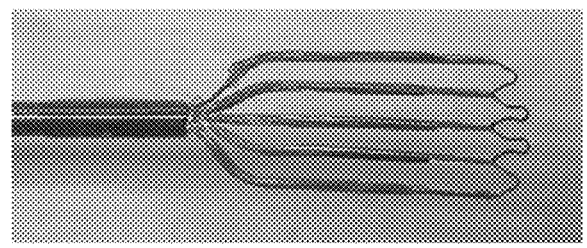
FIG. 7B illustrates withdrawal of the sixth catheter into a sheath or holding tube, according to one or more embodiments.
Figure 7B:
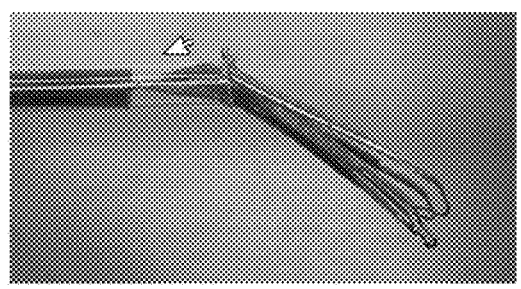
Figure 7B:
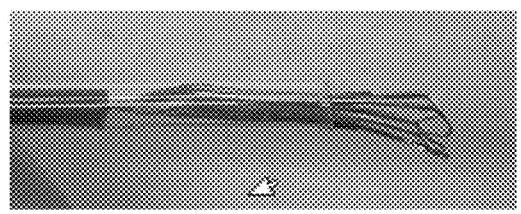
Figure 7B:
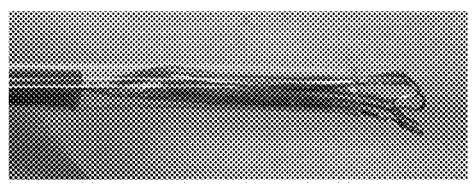
Figure 7B:
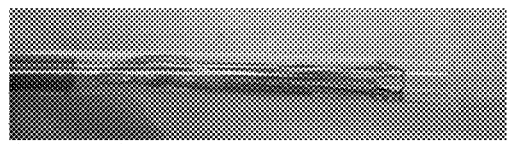

FIG. 7B illustrates a transition between an expanded state and a compact state of the catheter 700 of FIG. 7A, according to one or more embodiments. In this animated sequence, the catheter 700 is retracted into the sheath, which is transparent for viewability of the catheter 700.

At step 762, the catheter 700 is an expanded state. The splines 720 are spaced out, and the connectors 730 are in a minimal energy state.

At step 764, the sheath envelops one quarter of the catheter 700. Curved portions of the outer splines at the proximal end begin to deform.

At step 766, the sheath envelops half of the catheter 700. The curved portions of all splines 720 are deformed, i.e., straightened out. The connectors 730 are also beginning to deform, wherein the curvature in the bends of the connectors are changing.

At step 768, the sheath envelops three quarters of the catheter 700. The connectors 730 continue to deform.

At step 770, the sheath fully envelops the catheter 700, wherein the catheter 700 is in a compact state. The splines 720 are substantially straightened out. Some or all bends of the splines 720 and/or the connectors 730 are in a high energy state.

In the compact state, the catheter 700 and the shaft 150 can be inserted via an access point (e.g., a vascular access point) and steered to the tissue (e.g., the heart tissue). At the tissue, the catheter 700 can be deployed to the expanded state for treatment of a heart rhythm disorder. Once treatment is complete, the catheter 700 can be retracted to the compact state for removal from the patient.

Transitioning back to the expanded state, as the catheter 700 extends beyond the sheath, some or all bends of the splines 720 and/or the connectors 730 want to relax and return to their minimal energy state. As the sheath allows for the catheter 700 to expand, the stored energy in the deformed bends expands and spaces out the splines 720, back to the expanded state shown in step 762.

Figure 8A:
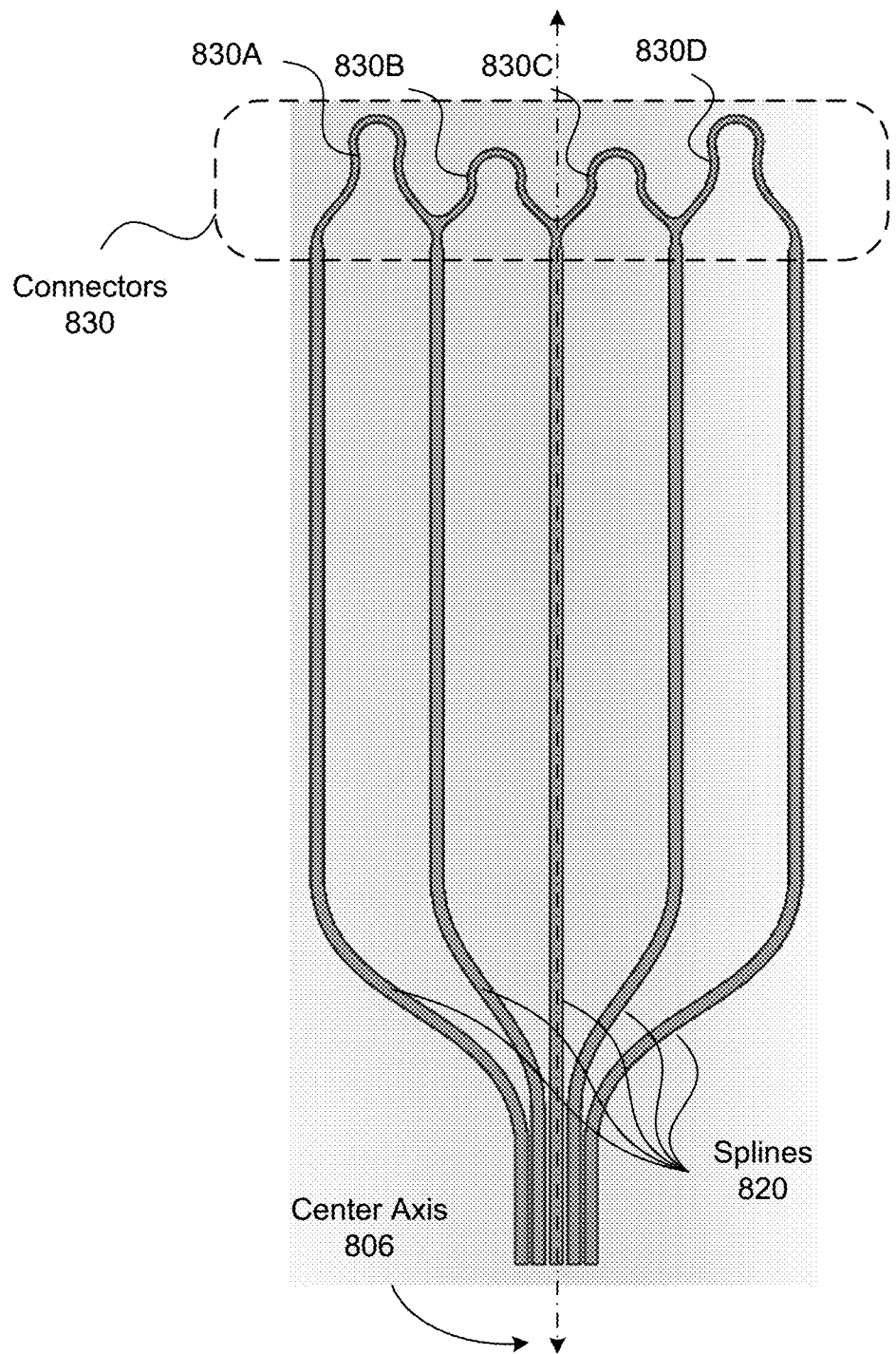
FIG. 8A illustrates a top view of a seventh catheter that may be implemented in the heart treatment device, according to one or more embodiments.

FIG. 8A illustrates a top view of a seventh catheter 800 that may be implemented in the heart treatment device 105, according to one or more embodiments. The catheter 800 is shown in an expanded state, wherein the catheter 800 is unsheathed or deployed. The catheter 800 comprises, among other components, a plurality of splines 820 and a plurality of connectors 830. The plurality of splines 820 is an embodiment of the plurality of splines 420, and the plurality of connectors 830 is an embodiment of the plurality of connectors 430. The catheter 800 also comprises an electrode array (not shown), which may be an embodiment of the electrode array 440. The catheter 800 may further include a plurality of irrigation pores (not shown), which may be an embodiment of the plurality of irrigation pores 450. Various other sensors and/or components described under catheter 400 may also be implemented.

The catheter 800 includes five total splines in the splines 820. The five splines include a middle spline aligned with the center axis 806, two inner splines disposed on either side of the middle spline, and two outer splines disposed on either side of the inner splines (as shown in FIG. 8A). The five splines are all substantially parallel to one another. In the embodiment of catheter 800, the splines 820 have linear portions, where the electrode array is disposed, that are substantially the same length. Put in another manner, the linear portions of the splines 820 extend to the same distance as measured along the center axis 806.

The catheter 800 includes four connectors in the connectors 830. Each connector connects distal ends of adjacent splines. Connector 830A connects the left outer spline to the left inner spline. Connector 830B connects the left inner spline to the middle spline. Connector 830C connects the middle spline to the right inner spline. Connector 830D connects the right inner spline to the right outer spline.

Connectors 830A, 830B, 830C, and 830D all have a U-shaped bend. Connector 830A and connector 830D have substantially the same length measured along the center axis 806. Connector 830B and connector 830C have substantially the same length measured along the center axis 806, which is smaller than the lengths of connector 830A and connector 830D. In additional embodiments, the length of the connectors 830 have varying lengths.

Figure 8B:
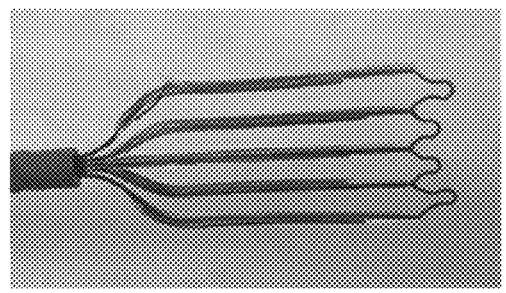
FIG. 8B illustrates withdrawal of the seventh catheter into a sheath or holding tube, according to one or more embodiments.
Figure 8B:
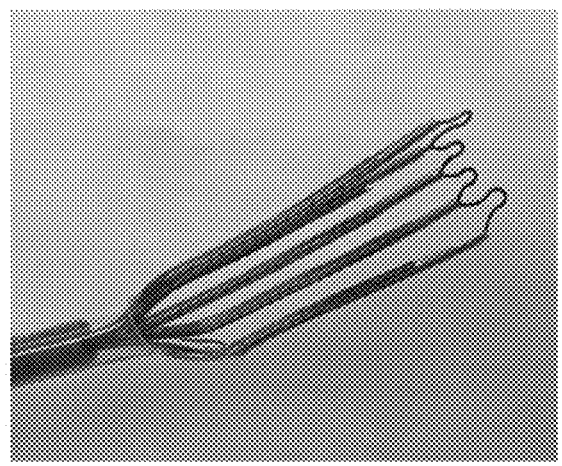
Figure 8B:
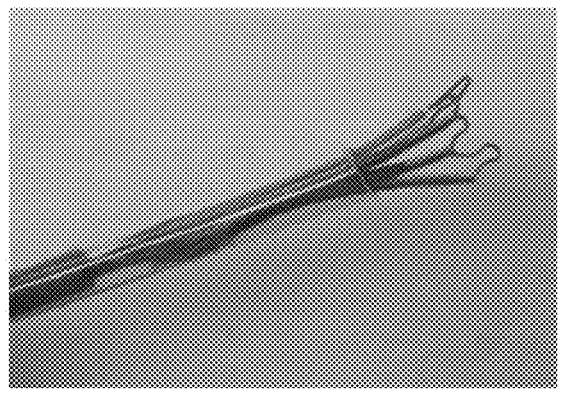
Figure 8B:
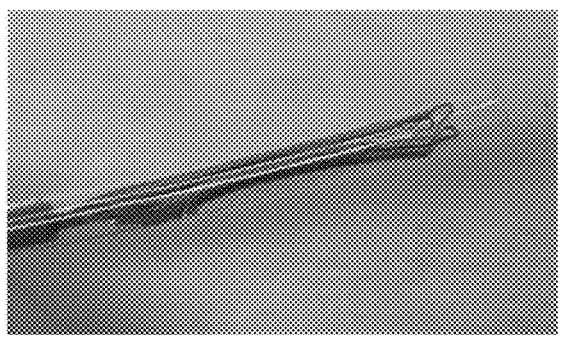

FIG. 8B illustrates a transition between an expanded state and a compact state of the catheter 800 of FIG. 8A, according to one or more embodiments. In this animated sequence, the catheter 800 is retracted into the sheath, which is transparent for viewability of the catheter 800.

At step 862, the catheter 800 is an expanded state. The splines 820 are spaced out, and the connectors 830 are in a minimal energy state.

At step 864, the sheath envelops one fifth of the catheter 800. Curved portions of the outer splines at the proximal end begin to deform.

At step 866, the sheath envelops two thirds of the catheter 800. The curved portions of all splines 820 are deformed, i.e., straightened out. The connectors 830 are also beginning to deform, wherein the curvature in the bends of the connectors are changing.

At step 868, the sheath fully envelops the catheter 800, wherein the catheter 800 is in a compact state. The splines 820 are substantially straightened out. Some or all bends of the splines 820 and/or the connectors 830 are in a high energy state.

In the compact state, the catheter 800 and the shaft 150 can be inserted via an access point (e.g., a vascular access point) and steered to the tissue (e.g., the heart tissue). At the tissue, the catheter 800 can be deployed to the expanded state for treatment of a heart rhythm disorder. Once treatment is complete, the catheter 800 can be retracted to the compact state for removal from the patient.

Transitioning back to the expanded state, as the catheter 800 extends beyond the sheath, some or all bends of the splines 820 and/or the connectors 830 want to relax and return to their minimal energy state. As the sheath allows for the catheter 800 to expand, the stored energy in the deformed bends expands and spaces out the splines 820, back to the expanded state shown in step 862.

Figure 9:
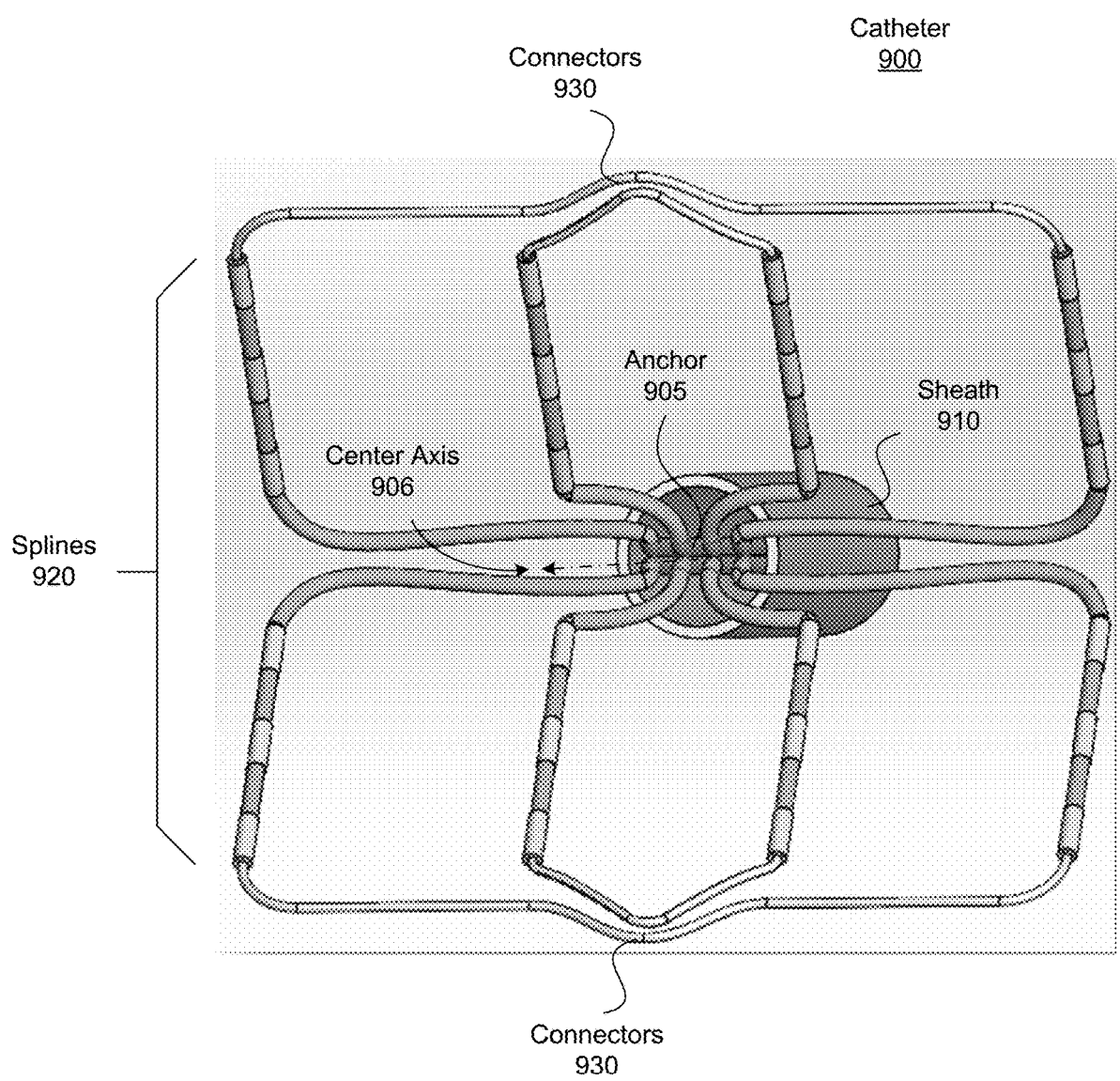
FIG. 9 illustrates an eighth catheter that may be implemented in the heart treatment device, according to one or more embodiments.

FIG. 9 illustrates a top view of an eighth catheter 900 that may be implemented in the heart treatment device 105, according to one or more embodiments. The catheter 900 is shown in an expanded state, wherein the catheter 900 is unsheathed or deployed. The catheter 900 comprises, among other components, a plurality of splines 920 and a plurality of connectors 930. The plurality of splines 920 is an embodiment of the plurality of splines 920, and the plurality of connectors 930 is an embodiment of the plurality of connectors 930. The catheter 900 also comprises an electrode array (not shown), which may be an embodiment of the electrode array 440. The catheter 900 may further include a plurality of irrigation pores (not shown), which may be an embodiment of the plurality of irrigation pores 450. Various other sensors and/or components described under catheter 400 may also be implemented.

The splines 920 comprise of eight splines that expand into a substantially planar configuration that is perpendicular to the center axis 906 of the shaft and sheath 910. Four splines expand away from the center axis 906 towards one side, while another four splines expand away from the center axis 906 towards an opposite side. The first set of four splines on a first side are substantially parallel to one another and planar. The second set of four splines on a second side are substantially parallel to one another and planar. Each of the splines 920 includes one or more bends in curved portions connecting to the anchor 905. The bends act to store energy when the splines 920 are collapsed into the compact state.

The connectors 930 comprise at least four connectors connecting the splines 920. As shown in FIG. 9, two connectors connect the first set of four splines, with another two connectors connecting the second set of four splines. A first connector of the first set connects outer splines of the first set of four splines to form an outer loop. A second connector of the first set connects inner splines of the first set of four splines to form an inner loop. Similar with the second set of four splines, one connector connects the outer splines to form an outer loop and a second connector connects the inner splines to form an inner loop. Each connector have a substantially V-shaped bend capable of storing energy for transitioning the splines 920 into their expanded state. In one or more embodiments, the splines 920 and the connectors 930 are monolithically formed. In other embodiments, each loop (e.g., each inner loop and each outer loop) is monolithically formed.

Figure 10:
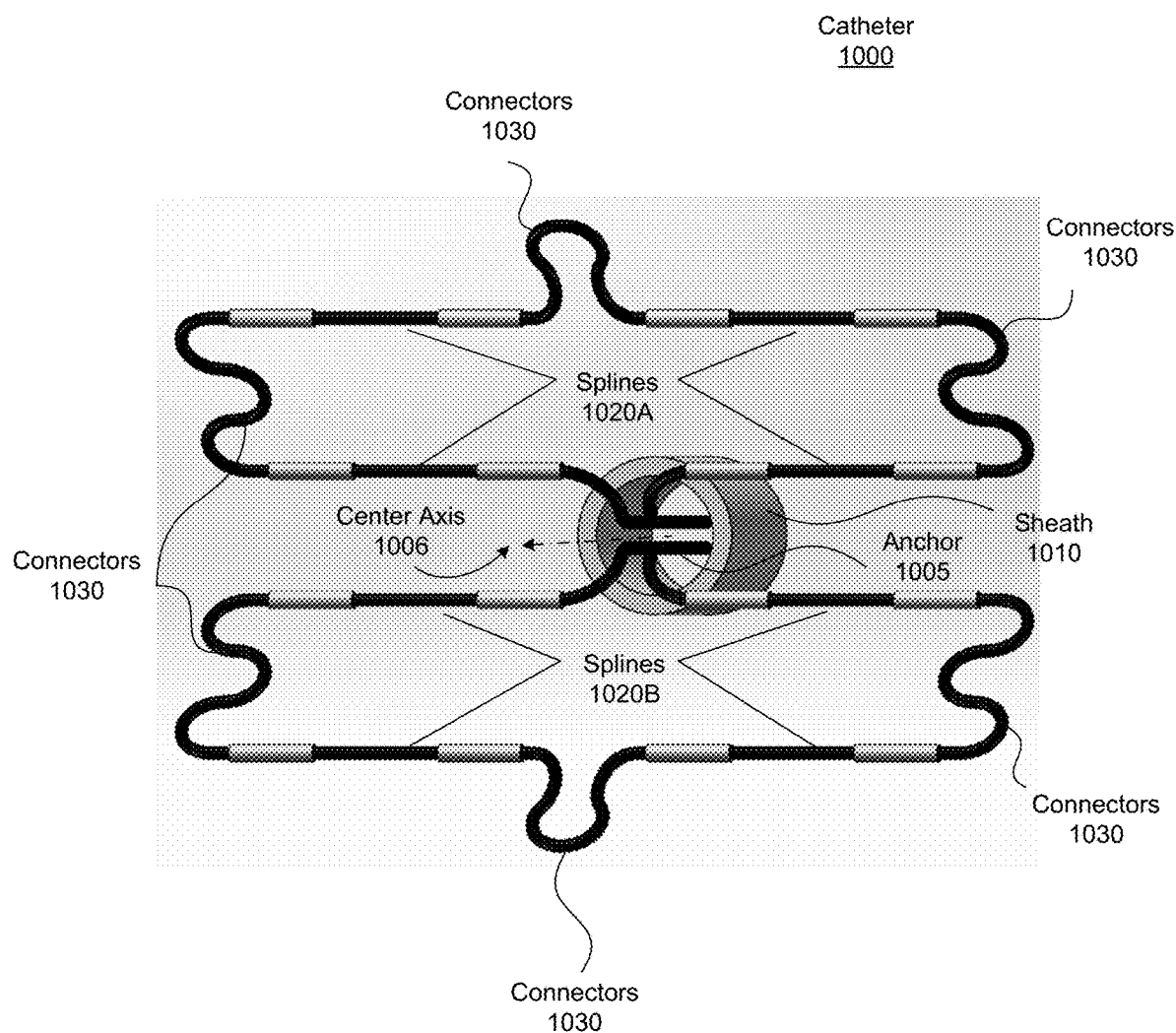
FIG. 10 illustrates a ninth catheter that may be implemented in the heart treatment device, according to one or more embodiments.

FIG. 10 illustrates a top view of a ninth catheter 1000 that may be implemented in the heart treatment device 105, according to one or more embodiments. The catheter 1000 is shown in an expanded state, wherein the catheter 1000 is unsheathed or deployed. The catheter 1000 comprises, among other components, a plurality of splines 1020 and a plurality of connectors 1030. The plurality of splines 1020 is an embodiment of the plurality of splines 1020, and the plurality of connectors 1030 is an embodiment of the plurality of connectors 1030. The catheter 1000 also comprises an electrode array (not shown), which may be an embodiment of the electrode array 440. The catheter 1000 may further include a plurality of irrigation pores (not shown), which may be an embodiment of the plurality of irrigation pores 450. Various other sensors and/or components described under catheter 400 may also be implemented.

The splines 1020 comprise eight splines, that expand into a substantially planar configuration that is perpendicular to the center axis 1006 of the shaft and sheath 1010. The splines 1020 are also split into two sets of four splines. The first set of four splines 1020A are connected by three connectors 1030 to form a single loop. The second set of four splines 1020B are connected by another three connectors 1030 to form a second loop. Both loops are substantially planar and perpendicular to the center axis 1006.

The connectors are substantially ring-shaped, with one or more bends included in each connector. In the first loop including splines 1020A, two connectors connect inner splines closest to the center axis 1006 to outer splines furthest from the center axis 1006. These two connectors extend towards an interior area enclosed by the loop. A third connector connects the two outer splines, closing the loop. The third connector, situated at the top of FIG. 10, extends towards away from the interior area enclosed by the loop. Similarly, with the second loop, shown at the bottom of FIG. 10, there are three connectors—two connectors connecting the inner splines to the outer splines and a third connector connecting the outer splines. The two connectors connecting the inner splines to the outer splines extend towards an interior area enclosed by the loop, while the third connector, situated at the bottom of FIG. 10, extends towards away from the interior area enclosed by the loop. In other embodiments, the connectors 1030 could be oriented differently, e.g., all of the connectors 1030 extend away from the interior area enclosed by the loops, or all of the connectors 1030 extend toward the interior area enclosed by the loops.

Figure 11A:
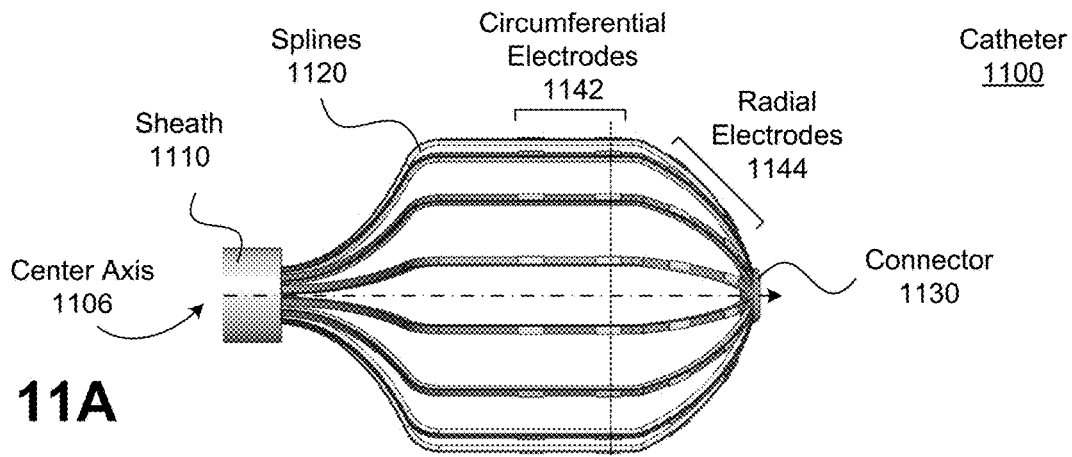
FIGS. 11A-11C illustrate multiple views of a tenth catheter that may be implemented in the heart treatment device, according to one or more embodiments.
Figure 11B:
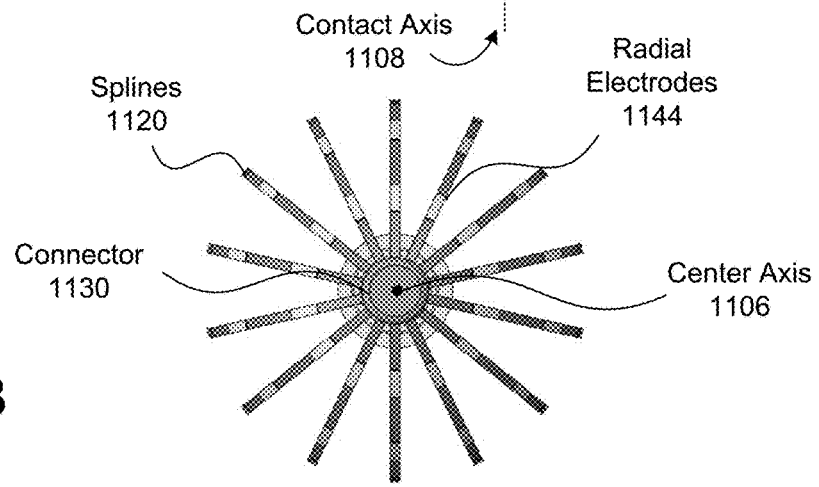
Figure 11C:
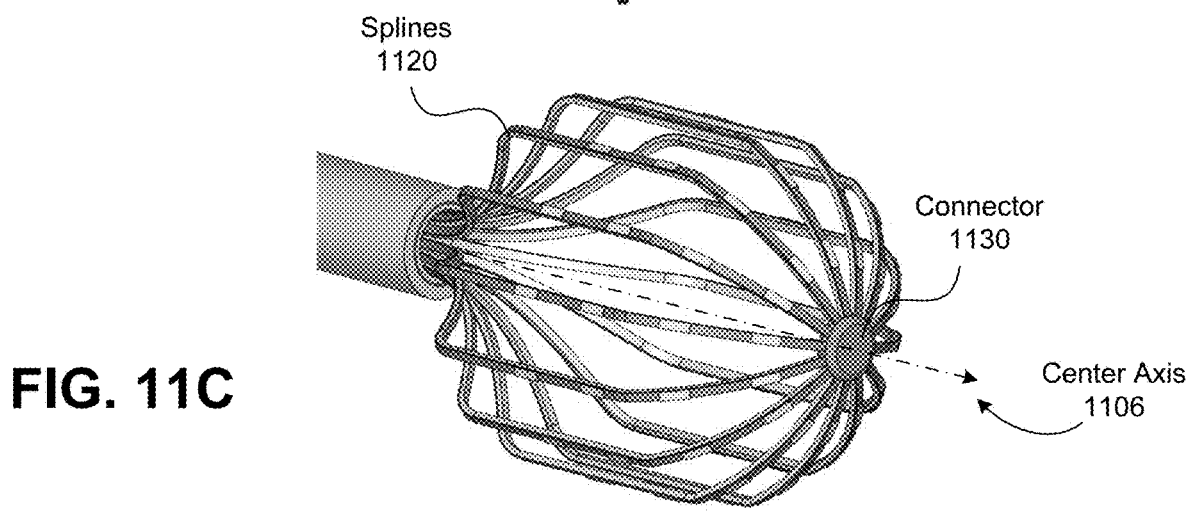

FIGS. 11A-11C illustrate multiple views of a tenth catheter 1100 that may be implemented in the heart treatment device 105, according to one or more embodiments. FIG. 11A is a side view of the catheter 1100; FIG. 11B is a head-on view down the center axis 1106; and FIG. 11C is a perspective view of the catheter 1100. The catheter 1100 includes a plurality of splines 1120 that form a basket-like shape with the electrode array disposed on the splines 1120. The catheter 1100 may further include a plurality of irrigation pores (not shown), which may be an embodiment of the plurality of irrigation pores 450. Various other sensors and/or components described under catheter 400 may also be implemented.

The splines 1120 form a basket-like shape for the electrode array. Each spline has a similar shape, which includes a first portion that extends from the sheath 1110 and away from the center axis 1106. A second portion is linear and substantially parallel to the center axis 1106. A third portion has a circular curvature. The splines 1120 all connect at a distal end of the center axis 1106 via a connector 1130. In FIG. 11B, the splines are evenly spaced radially about the center axis 1106. The first portion of the splines 1120 forms a conical shape, the second portion of the splines 1120 forms a cylindrical shape, and the third portion of the splines 1120 from a semispherical shape. Each spline 1120 comprises a plurality of bends for storing energy when in the compact state. In other embodiments, each spline can have varying shapes, wherein the combined set of splines 1120 is capable of forming a basket-like shape, enclosing a radially symmetrical volumetric portion. Other embodiments may have more or less splines.

The electrode array comprises circumferential electrodes 1142 and radial electrodes 1144. As electrodes are disposed on both the cylindrical portion of the splines 1120 and the semispherical portion of the splines 1120, contacting heart tissue at any point from the contact axis 1108 and towards the distal end of catheter 1100 ensures at least 9 or more electrodes of the electrode array to be in contact with the heart tissue. The catheter 1100, thus, has versatility, being able to be oriented in any number of ways whilst still retaining high throughput functionality by the electrode array. The circumferential electrodes 1142 are placed on the cylindrical portion of the splines 1120. In FIGS. 11A-11C, there are two circumferential electrodes placed on each spline on the cylindrical portion. The radial electrodes 1144 are place on the semispherical portion of the splines 1120. In FIGS. 11A-11C, there are two radial electrodes placed on each spline on the semispherical portion. With a total of 14 splines, that results in 56 total electrodes, 28 circumferential electrodes and 28 radial electrodes. In other embodiments, there may be more or less electrodes placed on each spline.

Figure 12A:
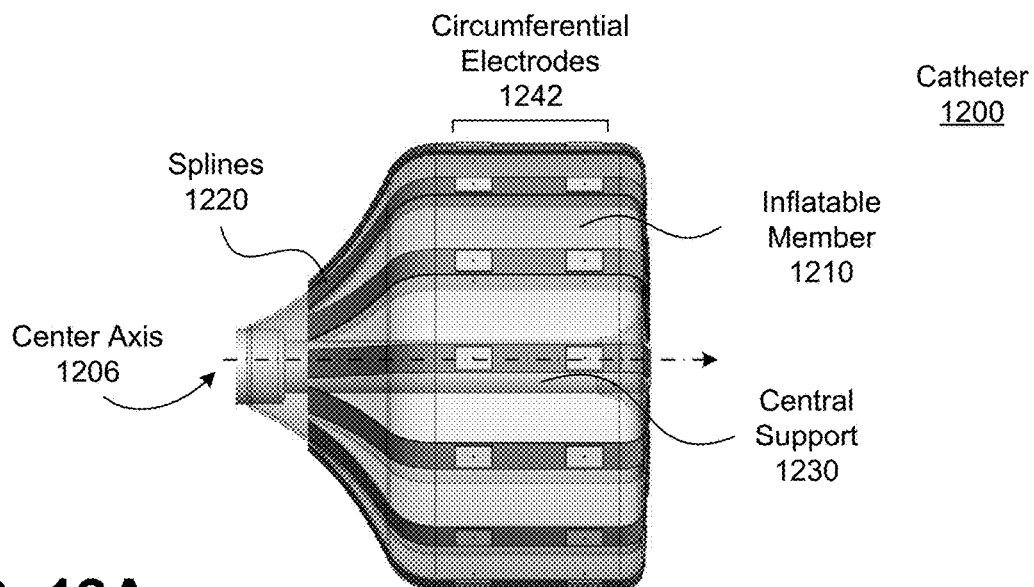
FIGS. 12A-12C illustrate multiple views of an eleventh catheter that may be implemented in the heart treatment device, according to one or more embodiments.
Figure 12B:
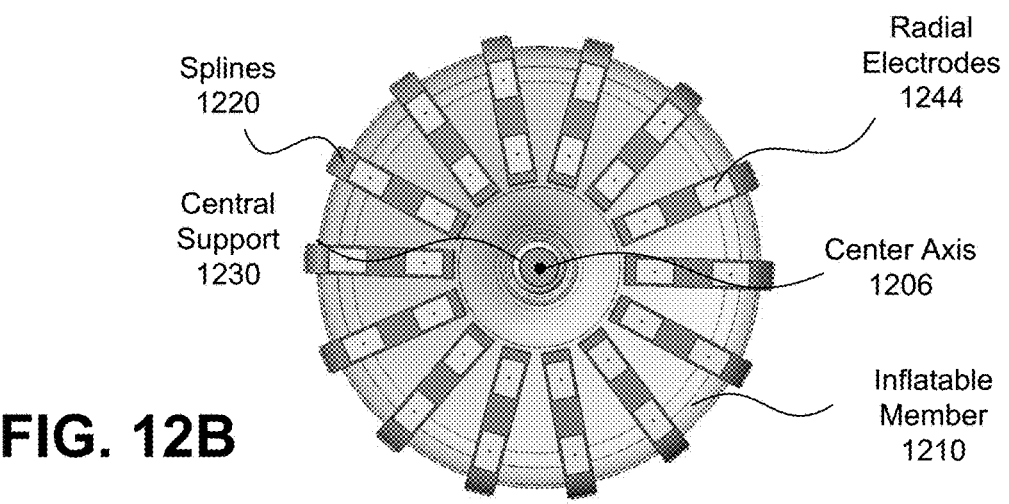
Figure 12C:
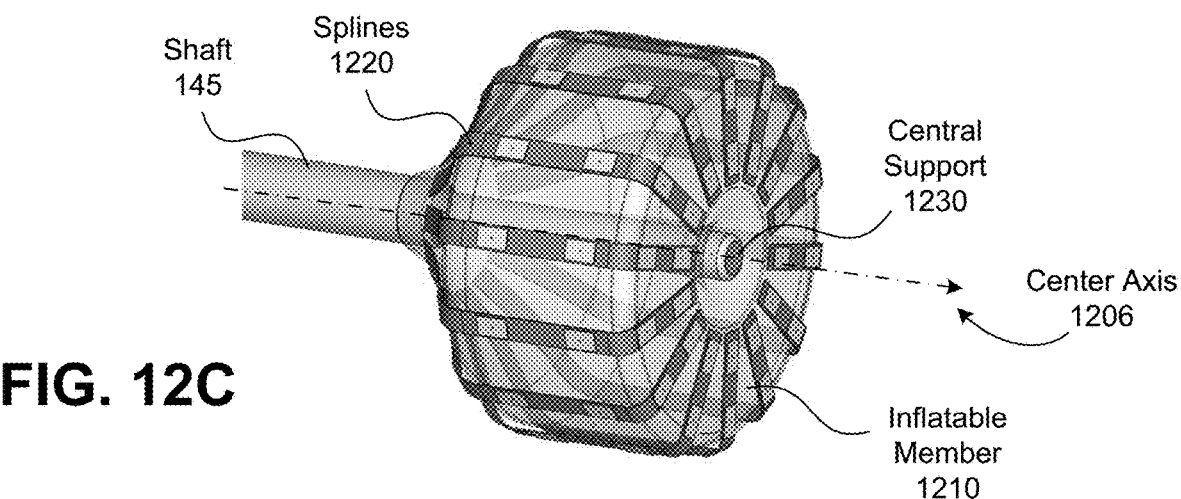

FIGS. 12A-12C illustrate multiple views of an eleventh catheter 1200 that may be implemented in the heart treatment device 105, according to one or more embodiments. FIG. 12A is a side view of the catheter 1200; FIG. 12B is a head-on view down the center axis 1206; and FIG. 12C is a perspective view of the catheter 1200. The catheter 1200 includes an inflatable member 1210, a plurality of splines 1220 coupled to the inflatable member 1210, an electrode array disposed on the splines 1220, and a central support 1230. The catheter 1200 may further include a plurality of irrigation pores (not shown), which may be an embodiment of the plurality of irrigation pores 450. Various other sensors and/or components described under catheter 400 may also be implemented.

The inflatable member 1210 is an elastic portion that is configured to inflate and deflate by movement of a fluid in and out of the inflatable member 1210. The inflatable member 1210 is composed of a relatively thin and strong membrane that is configured to hold a volume of the fluid. The inflatable member 1210 may be configured to expand and stretch when inflated with the fluid. In other embodiments, the inflatable member 1210 is not composed of a compliant material yet fills and expands when inflated with the fluid. The fluid may be any liquid or gas that is safe for use in a patient's body. For example, the fluid may be a saline infusate. The inflatable member 1210 may comprise a valve located at a distal end of the shaft 145 where the inflatable member 1210 is connected to the shaft 145. The valve is configured to allow fluid movement in and/or out of the inflatable member 1210. The valve may also be configured to seal the fluid within the inflatable member 1210, e.g., when the inflatable member 1210 is in the expanded state. In the shaft 145, there can be one or more fluid channels for pumping the fluid into and out of the inflatable member 1210. In the embodiment shown in FIGS. 12A-12C, the inflatable member 1210 has a first portion that is substantially conical in shape and a second portion that is substantially cylindrical in shape.

The splines 1220 provide support for placement of the electrode array. The splines 1220 couple to the inflatable member 1210 from a connection point between the inflatable member 1210 and the shaft 145 towards the center axis 1206 at a distal end of the catheter 1200. The splines 1220 may be formed from a bendable material that conforms to the shape of the inflatable member 1210. As such, the spline 1220 expand to the expanded state shown in FIGS. 12A-12C when the inflatable member is inflated into the expanded state. In one or more embodiments, the splines 1220 are coated with an insulative material to prevent operability of the electrode array. The splines 1220 may further house one or more irrigant channels within the splines 1220, wherein the irrigant channels connect to the irrigation pores on the catheter 1200, and electrical wiring to connect to the electrodes disposed on the splines 1220. As shown in FIGS. 12A-12C, in the expanded state, each spline has a first portion that is linear and starts at a proximal end of the catheter, i.e., where the catheter 1200 (or more specifically the inflatable member 1210) is coupled to the shaft 145, and extends away at a non-right angle from the center axis 1206, a second portion that is substantially linear and is parallel to the center axis 1206, and a third portion that is substantially linear and is perpendicular to the center axis 1206. There are 14 splines 1220 that are radially distributed shown in FIGS. 12A-12C, however, other embodiments have additional or fewer splines. Together, the splines 1220 form a first section that is conically shaped and a second section that is cylindrically shaped.

The central support 1230 provides structural stability to the catheter 1200. The central support 1230 is composed of rigid and strong material. The central support 1230 is linear and affixed to the shaft 145 at a distal end of the shaft 145 and extends along the central axis 1206 towards a distal direction. The inflatable member 1210 is affixed to either end of the central support 1230. In other embodiments, the central support 1230 can have varying shape and length. In one or more embodiments, the central support 1230 houses one or more fluid channels for controlling movement of the fluid in and out of the inflatable member 1210.

The electrode array comprises circumferential electrodes 1242 and radial electrodes 1244. The circumferential electrodes 1242 are disposed on the cylindrical portion of the splines 1220, specifically on the linear portions of each spline that run parallel to the center axis 1206. The radial electrodes 1244 are disposed on the cylindrical portion of the splines 1220, specifically on the linear portions of each spline that are perpendicular to the center axis 1206. Due to the placement of the circumferential electrodes 1242 and the radial electrodes 1244, the electrode array is capable of contacting heart tissue from numerous directions while ensuring at least 6 or more electrodes of the electrode array to be in contact with the heart tissue. In particular, at least 6 circumferential electrodes are contacted when the side of the cylindrical portion of the splines 1220 is in contact with heart tissue, and at least 12 or more electrodes of the electrode array would be contacted when the distal end of the cylindrical portion is contacted with the heart tissue. The catheter 1200, thus, has versatility, being able to be oriented in any number of ways whilst still retaining high throughput functionality by the electrode array. In FIGS. 12A-12C, there are two circumferential electrodes 1242 placed on each spline on the portion parallel to the center axis 1206. In FIGS. 12A-12C, there are two radial electrodes placed on each spline on the portion perpendicular to the center axis 1206. With a total of 14 splines, that results in 56 total electrodes, 28 circumferential electrodes 1242 and 28 radial electrodes 1244. In other embodiments, there may be more or less electrodes placed on each spline.

Figure 13:
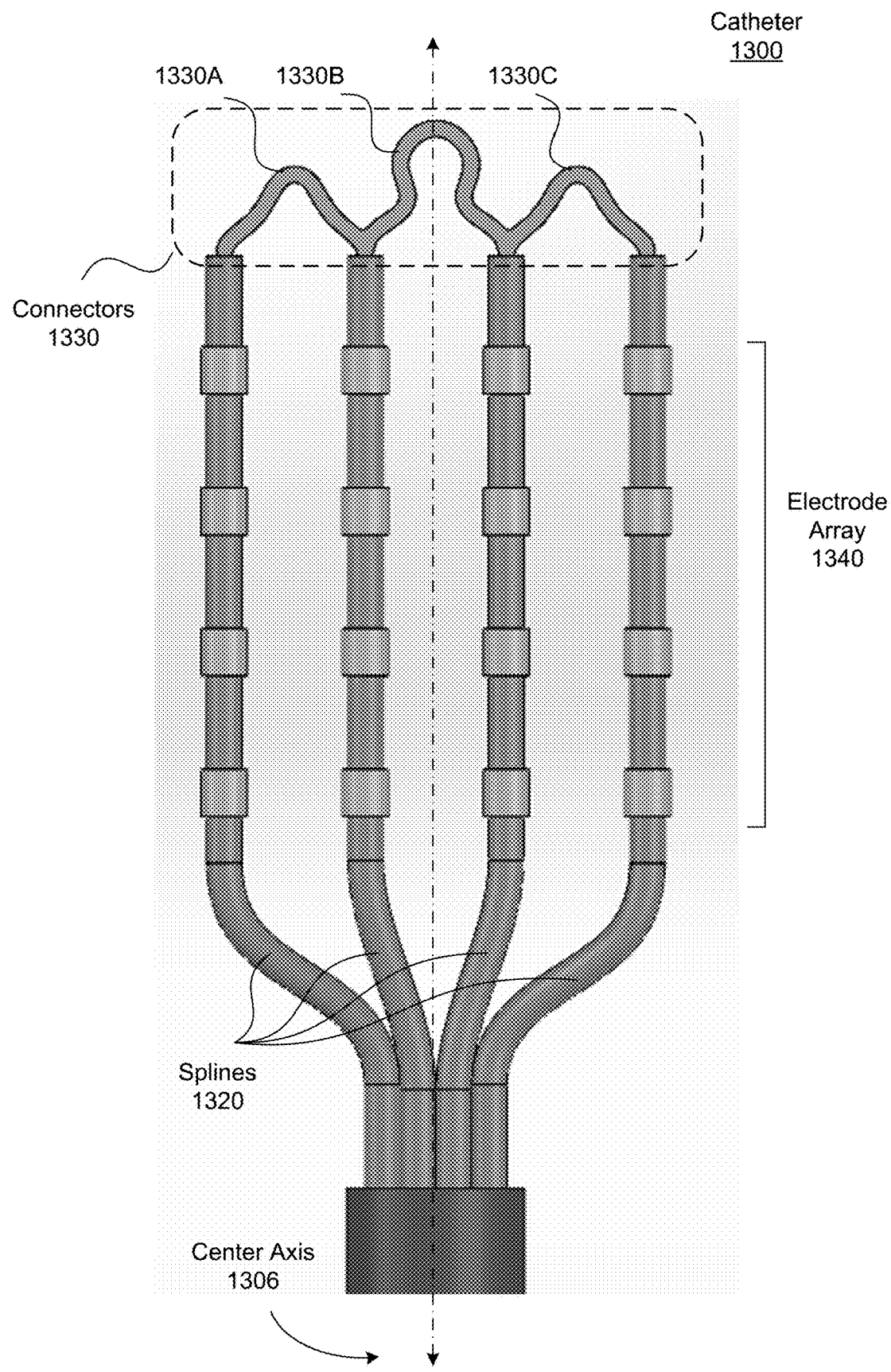
FIG. 13 illustrates a twelfth catheter that may be implemented in the heart treatment device, according to one or more embodiments.

FIG. 13 illustrates a twelfth catheter 1300 that may be implemented in the heart treatment device 105, according to one or more embodiments. The catheter 1300 comprises four splines 1320 with connectors 1330 connecting adjacent splines. The splines 1320 and connectors 1330 may be monolithically formed. As shown, there are three connectors 1330, connector 1330A connects adjacent inner spline and outer spline, connector 1330B connects the two inner splines, and connector 1330C connects the other adjacent inner spline and outer spline. The connectors 1330A and 1330C are substantially v-shaped. The connector 1330B comprises a 270° arc of a circle and linear portions connecting ends of the arc to the inner splines. The connector 1330B extends beyond the other connectors along the center axis 1306. The electrode array 1340 is disposed on the splines 1320.

Figure 14:
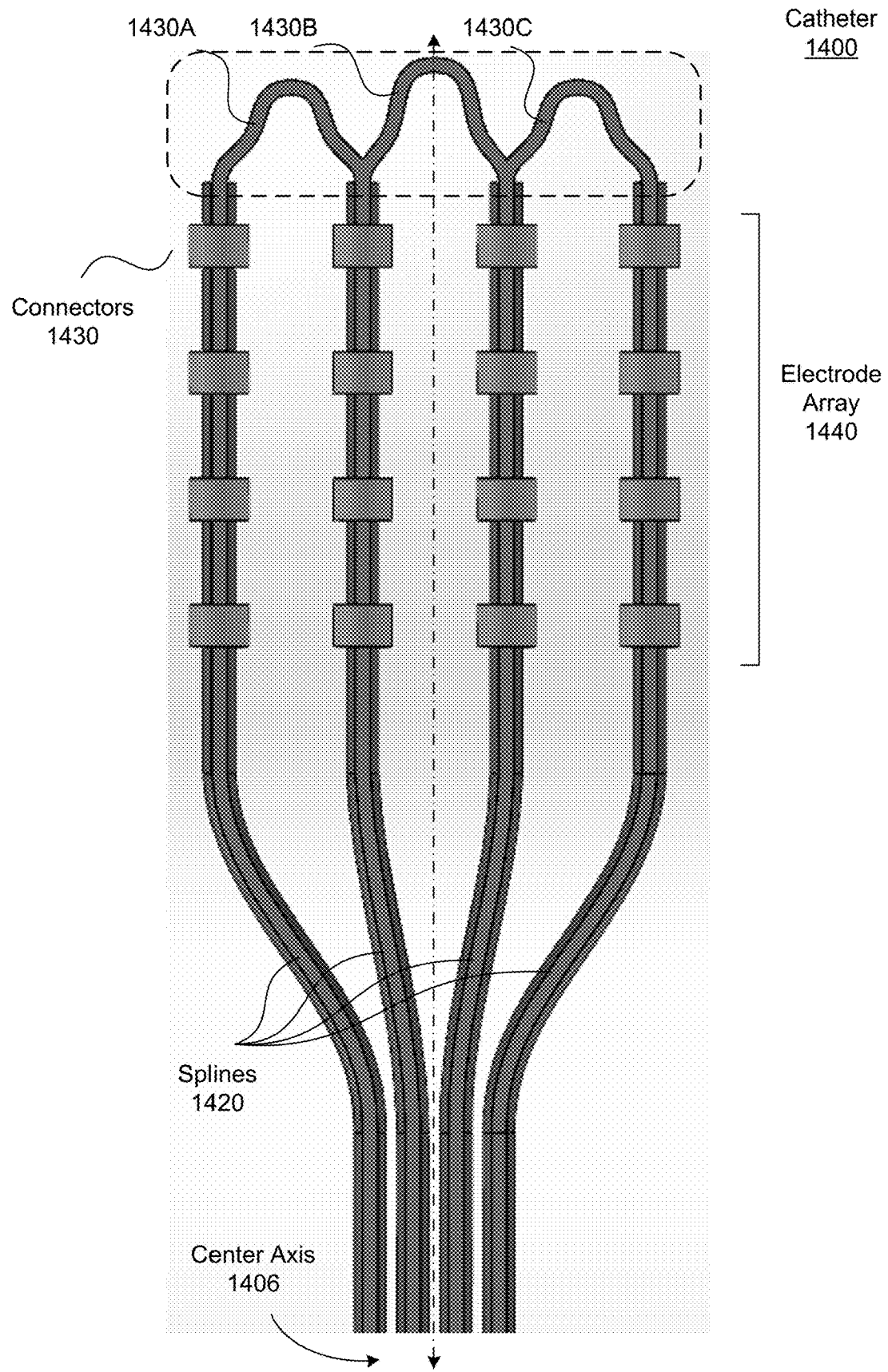
FIG. 14 illustrates a thirteenth catheter that may be implemented in the heart treatment device, according to one or more embodiments.

FIG. 14 illustrates a thirteenth catheter 1400 that may be implemented in the heart treatment device 105, according to one or more embodiments. The catheter 1400 comprises four splines 1420 with connectors 1430 connecting adjacent splines. The splines 1420 and connectors 1430 may be monolithically formed. As shown, there are three connectors 1430, connector 1430A connects adjacent inner spline and outer spline on a left of the center axis 1406, connector 1430B connects the two inner splines, and connector 1430C connects the other adjacent inner spline and outer spline on a right of the center axis 1406. All three connectors 1430 are substantially u-shaped having a more gradual curve on a distal end of the connectors 1406. The connector 1430B extends beyond the other connectors along the center axis 1406. The electrode array 1440 is disposed on the splines 1420.

Figure 15:
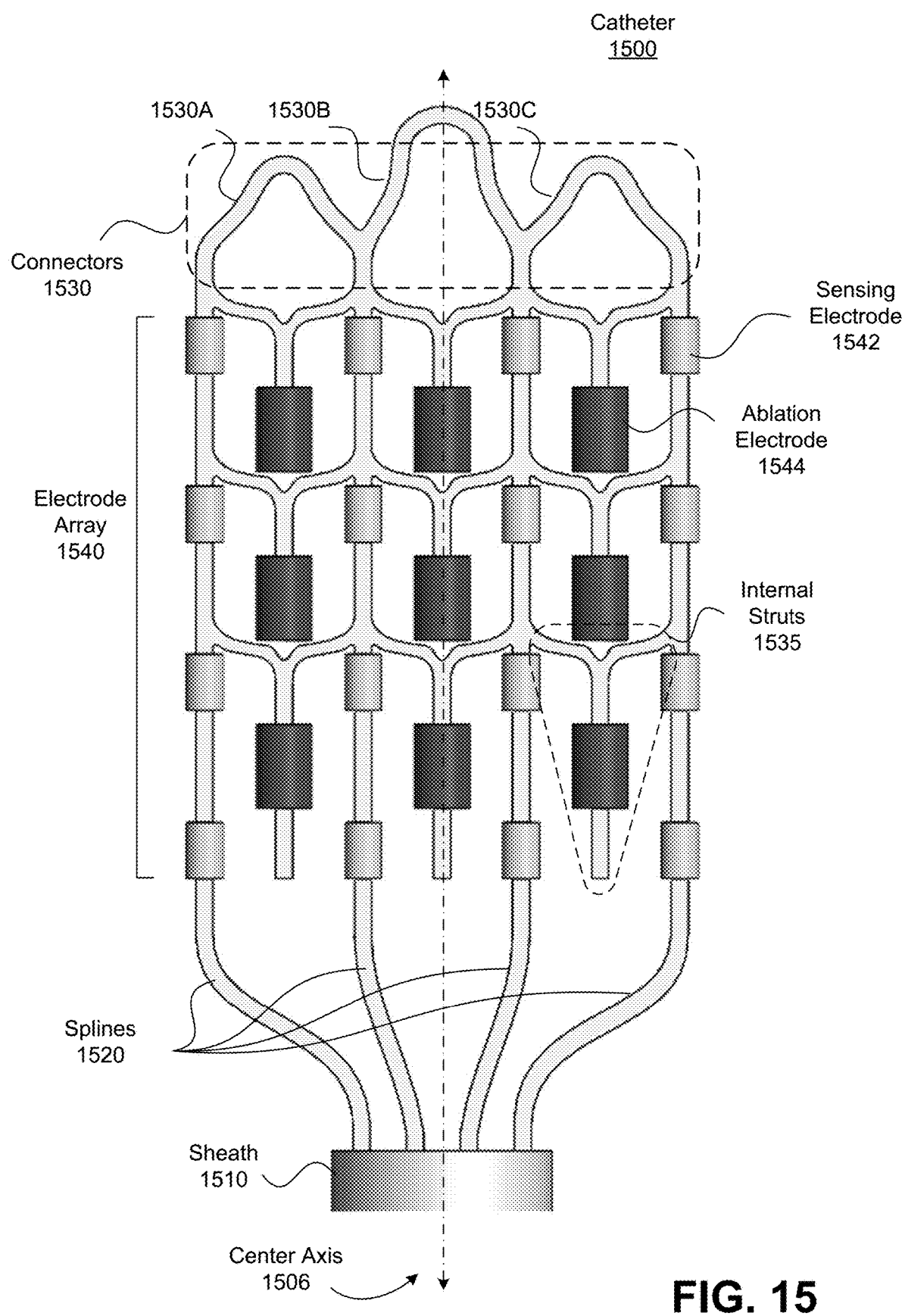
FIG. 15 illustrates a fourteenth catheter that may be implemented in the heart treatment device, according to one or more embodiments.

FIG. 15 illustrates a fourteenth catheter 1500 that may be implemented in the heart treatment device 105, according to one or more embodiments. The catheter 1500 comprises four splines 1520 with connectors 1530 connecting adjacent splines at a distal end of the splines 1520. The connectors 1530 have a similar shape to the connectors 1430 of the catheter 1400. The catheter 1500 further comprises internal struts 1535 that join adjacent splines. Each internal strut 1535 is substantially t-shaped having one linear portion parallel to the center axis 1506 and of shorter length than the linear portion of the splines 1520. The linear portion of the internal strut 1535 is disposed equidistant between adjacent splines. The linear portion of the internal strut 1535 is attached to the adjacent splines with two tail portions that connect to a distal end of the linear portion of the internal strut 1535 and the adjacent splines. The tail portions are substantially perpendicular to the center axis 1506, e.g., within 15° from perpendicular. In the embodiment shown in FIG. 15, there are a total of nine internal struts 1535 with three internal struts between each pair of adjacent splines. The electrode array 1540 is disposed both on the splines 1520 as well as the internal struts 1535. The catheter 1500 comprising the internal struts 1535 provides for a denser spacing of the electrodes of the electrode array 1540. In the embodiment shown in FIG. 15, ablation electrodes 1544 are placed on the internal struts 1535 with the sensing electrodes 1542 places on the splines 1520.

Figure 16:
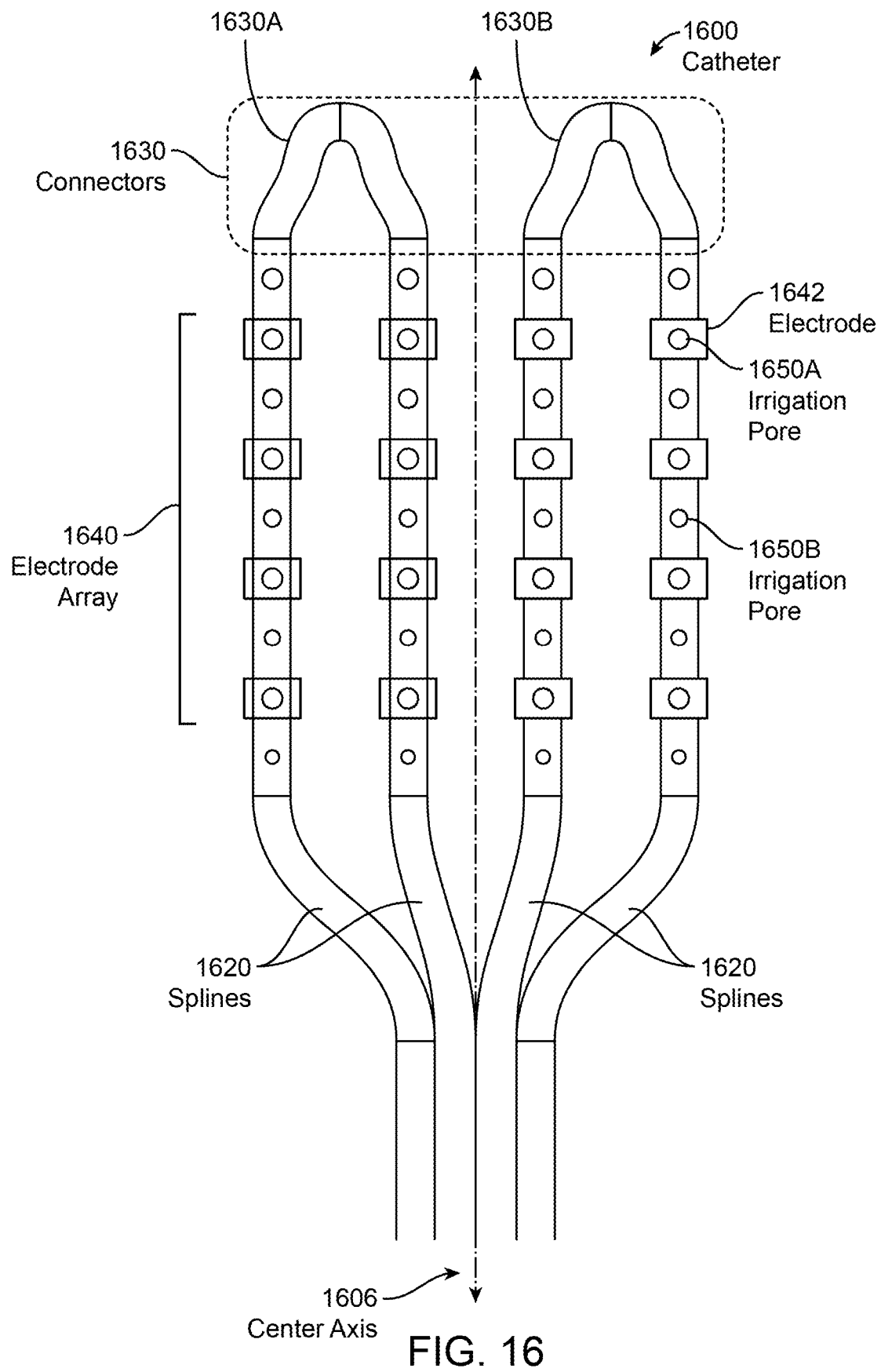
FIG. 16 illustrates a fifteenth catheter that may be implemented in the heart treatment device, according to one or more embodiments.

FIG. 16 illustrates a fifteenth catheter 1600 that may be implemented in the heart treatment device 105, according to one or more embodiments. The catheter 1600 comprises four splines 1620 and connectors 1630 connecting each pair of inner spline and outer spline disposed on each side of the center axis 1606. The connector 1630A connects the inner spline and outer spline on the left side of the center axis 1606, while the connector 1630B connects the inner spline and the outer spline on the right side of the center axis 1606. The connectors 1630 are substantially u-shaped, but may be shaped differently as shown in various connectors. The splines 1620 and the connectors 1630 are hollow, forming an interior cavity. Being hollow, the catheter 1600 can utilize the interior cavity as an irrigation channel with irrigation pores 1650 disposed at various positions along the splines 1620. In one or more embodiments, to ensure even flow across all the irrigation pores 1650, the irrigation pores towards a proximal end of the center axis 1606 are smaller than the irrigation pores towards a distal end of the center axis 1606. For example, irrigation pore 1650A is larger than the irrigation pore 1650B. As irrigant flows out of irrigation pores 1650 towards the proximal end, the flow pressure decreases, such that larger irrigation pores 1650 towards the distal end permit even flow despite decreased pressure.

Figure 17:
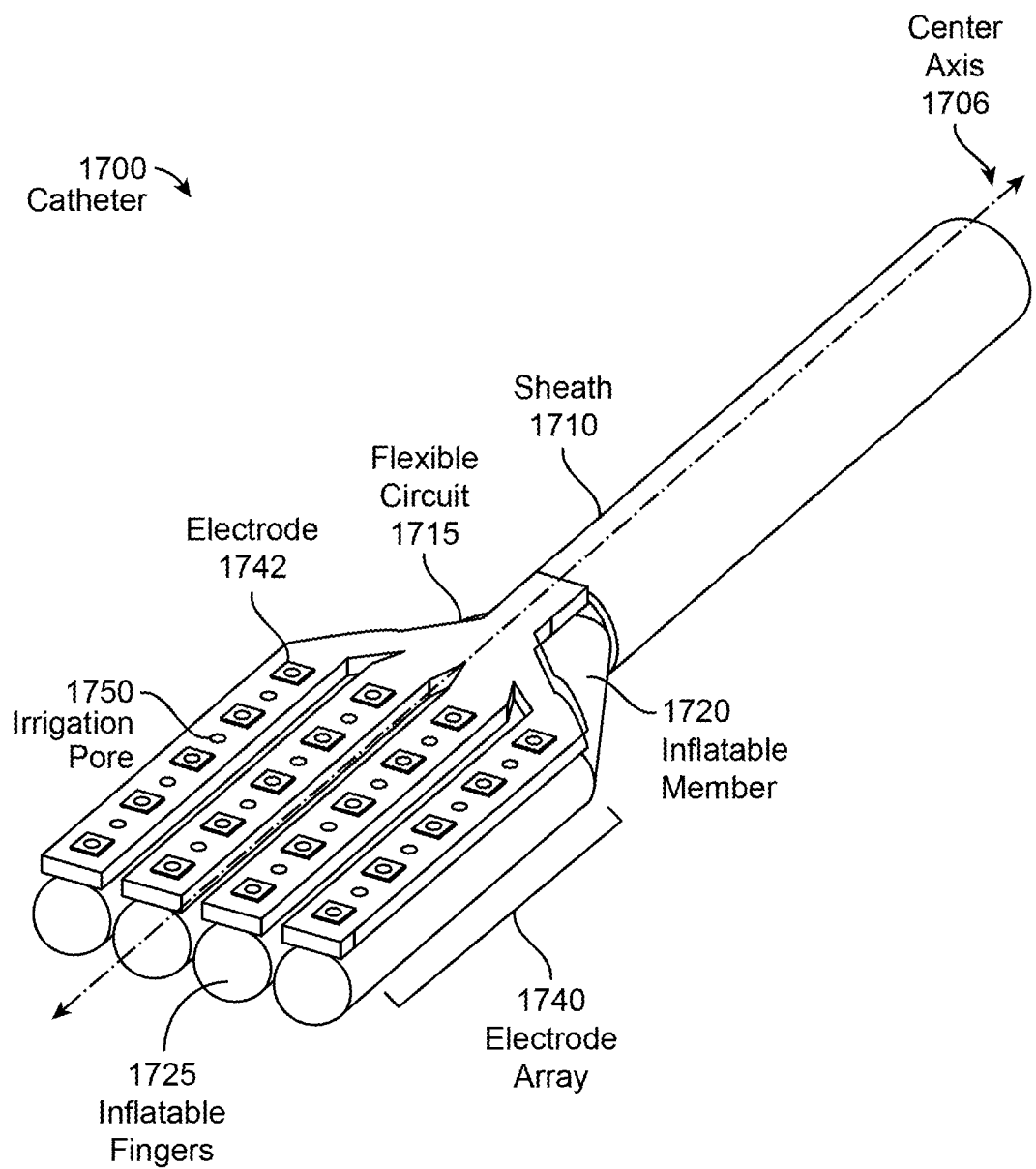
FIG. 17 illustrates a sixteenth catheter that may be implemented in the heart treatment device, according to one or more embodiments.

FIG. 17 illustrates a sixteenth catheter 1700 that may be implemented in the heart treatment device 105, according to one or more embodiments. The catheter 1700 may comprise an inflatable member 1720 and a flexible circuit 1715 coupled to the inflatable member 1720. The inflatable member 1720 may comprise a plurality of inflatable fingers 1725 that run parallel to one another along the center axis 1706. The inflatable member 1720 may be composed of a pliable material that can fold when in a compact state in the sheath 1710. To deploy and expand the inflatable member 1720, a fluid is pumped to expand the inflatable member 1720. In some embodiments, the fluid used to expand the inflatable member 1720 can be irrigant, e.g., also dispersed through irrigation pores 1750. The flexible circuit 1715 is also composed of a pliable material. The flexible circuit 1715 may comprise an insulative base with the circuit printed onto the insulative base. The electrode array 1740 may also be printed onto the insulative base. The electrodes 1742 may be evenly distributed in a rectangular array, as shown in FIG. 17, with 5 electrodes evenly spaced on each of four inflatable fingers 1725.

Figure 18:
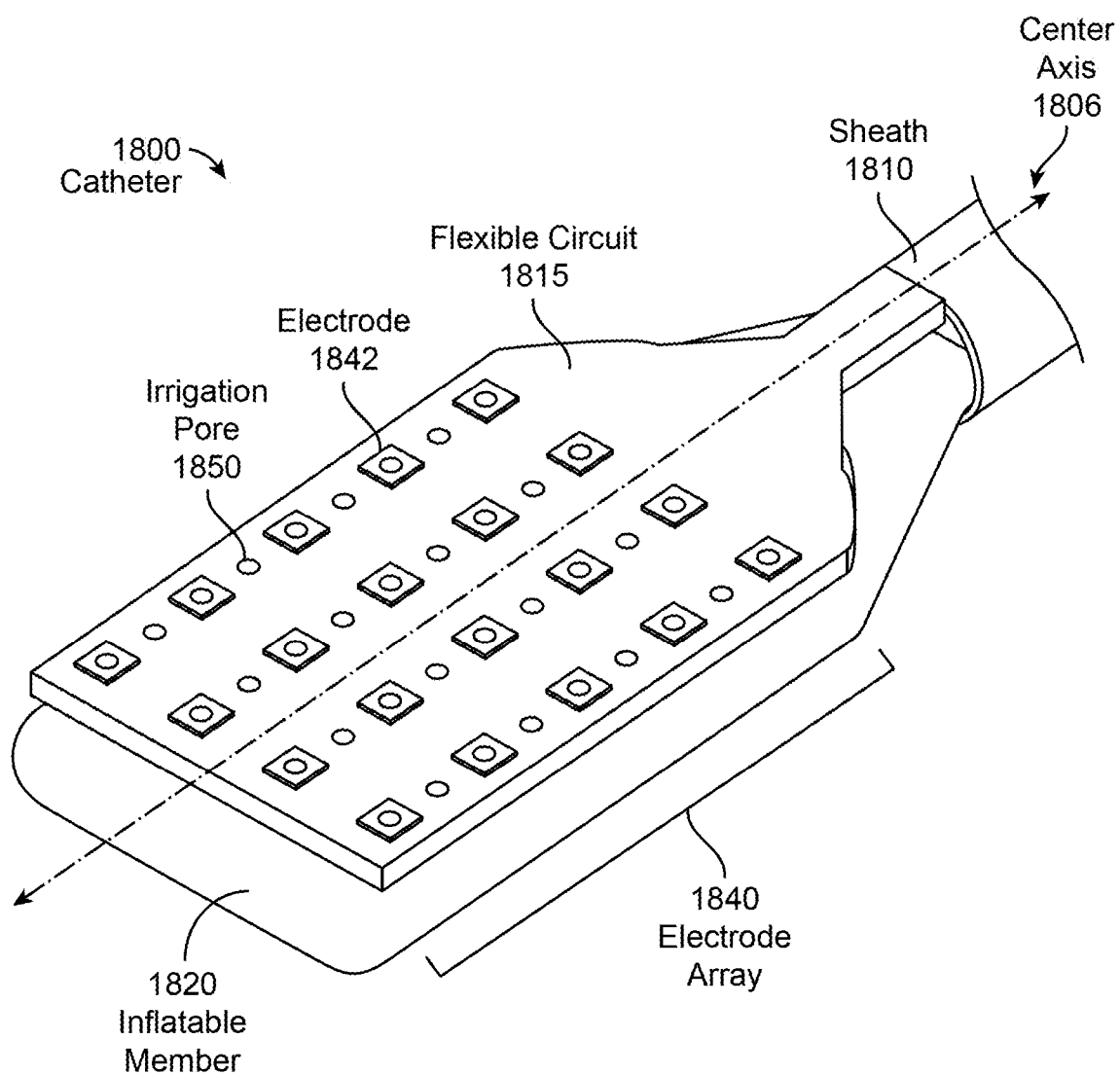
FIG. 18 illustrates a seventeenth catheter that may be implemented in the heart treatment device, according to one or more embodiments.

FIG. 18 illustrates a seventeenth catheter 1800 that may be implemented in the heart treatment device 105, according to one or more embodiments. The catheter 1800 comprises an inflatable member 1820 and a flexible circuit 1815. The inflatable member 1820, when expanded, is substantially rectangular shaped akin to a spatula. The inflatable member 1820 is composed of a pliable material that can fold and expand without deformation. To deploy and expand the inflatable member 1820, a fluid is pumped to expand the inflatable member 1820. In some embodiments, the fluid used to expand the inflatable member 1820 can be irrigant, e.g., also dispersed through irrigation pores 1850. The flexible circuit 1815 is also composed of a pliable material. The flexible circuit 1815 may comprise an insulative base with the circuit printed onto the insulative base. The electrode array 1840 may also be printed onto the insulative base. The electrodes 1842 may be evenly distributed in a rectangular array, as shown in FIG. 18.

Figure 19A:
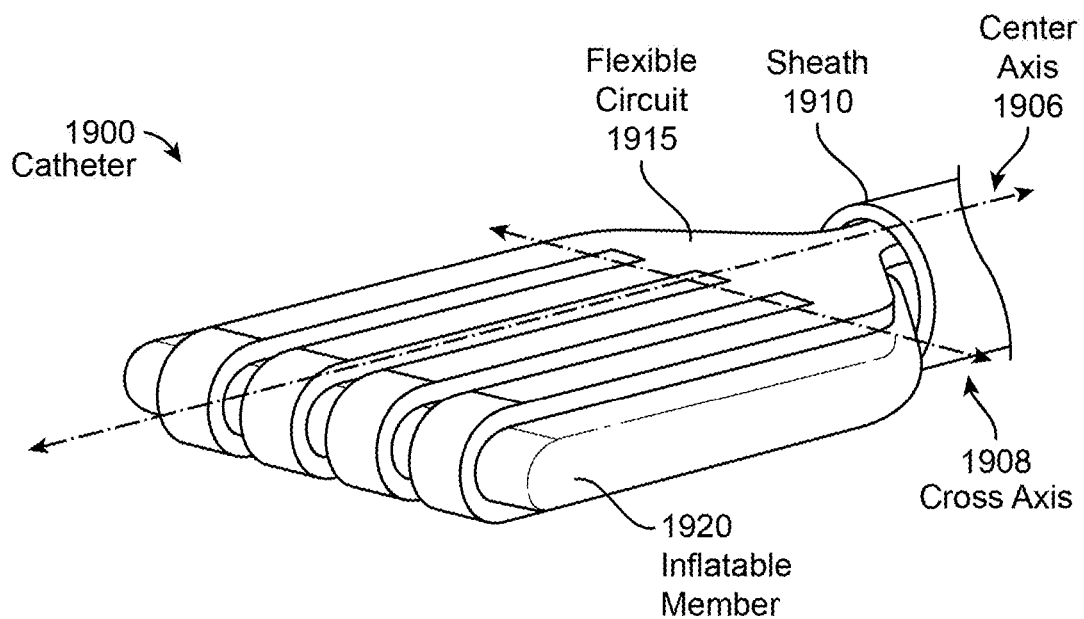
FIG. 19A illustrates a perspective view of an eighteenth catheter that may be implemented in the heart treatment device, according to one or more embodiments.
Figure 19B:
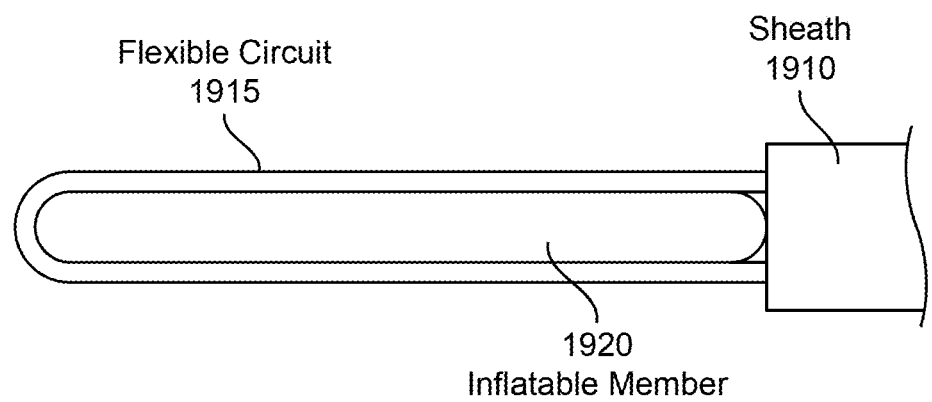
FIG. 19B illustrates a side view of the eighteenth catheter that may be implemented in the heart treatment device, according to one or more embodiments.

FIGS. 19A & 19B illustrate two views of an eighteenth catheter 1900 that may be implemented in the heart treatment device 105, according to one or more embodiments. FIG. 19A illustrates a perspective view of the catheter 1900. FIG. 19B illustrates a side view of the catheter 1900. The inflatable member 1920 is an embodiment of the inflatable member 1820 of the catheter 1800. The flexible circuit 1915 wraps around the inflatable member 1920, with the flexible circuit 1915 extending along a top flat side of the inflatable member 1920, around the distal end of the inflatable member 1920, and further along a bottom flat side of the inflatable member 1920. As the flexible circuit 1915 is on both sides of the inflatable member 1920, an electrode array may also be disposed on either side of the flexible circuit 1915. The flexible circuit 1915 is also composed of a pliable material. The flexible circuit 1915 may comprise an insulative base with the circuit printed onto the insulative base. The electrode array may also be printed onto the insulative base.

Figure 19C:
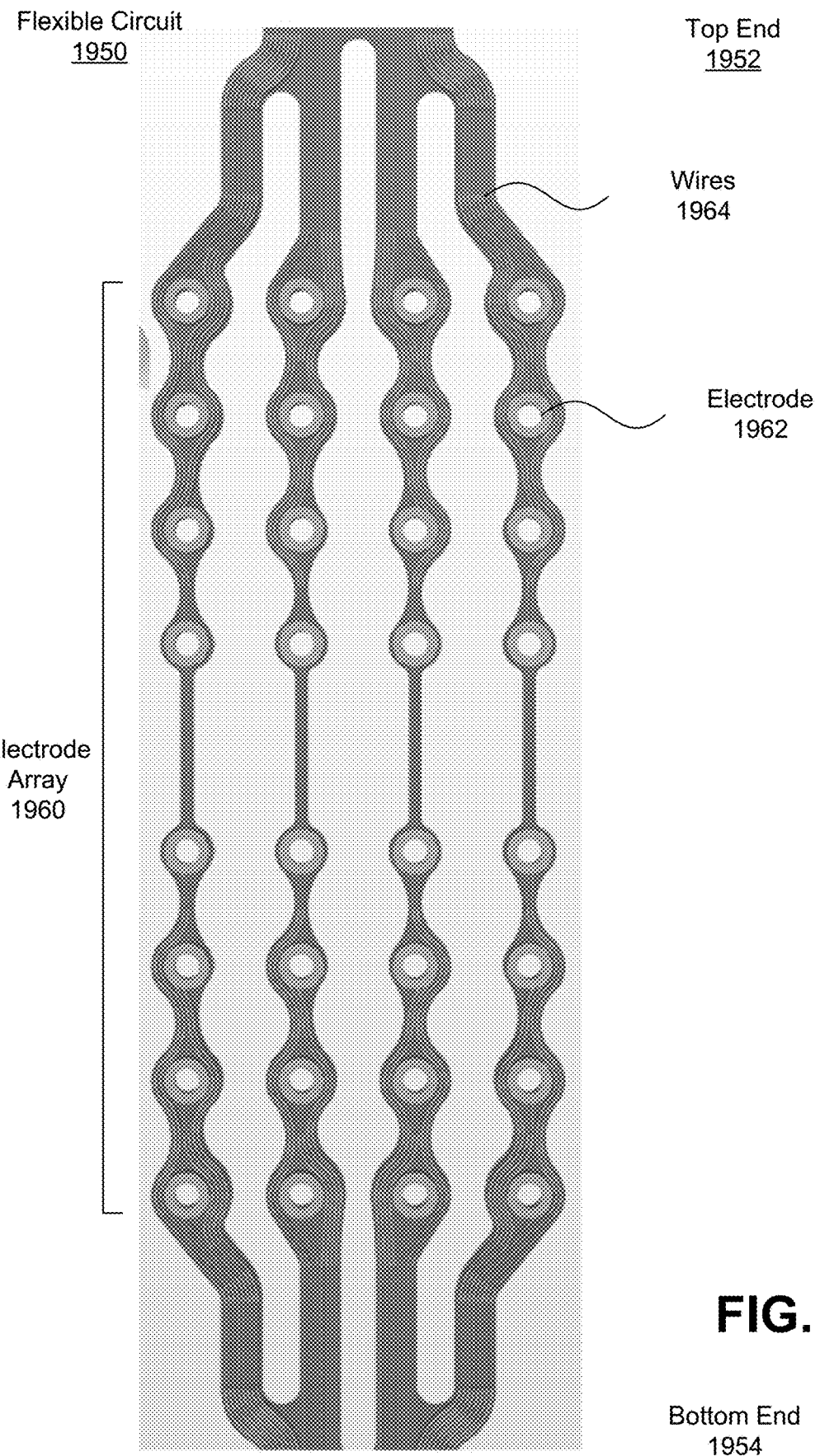
FIG. 19C illustrates a flexible circuit that can be implemented with a catheter of the heart treatment device, according to one or more embodiments.

FIG. 19C illustrates a flexible circuit 1950 that can be implemented with the catheter 1900 of FIGS. 19A & 19B, according to one or more embodiments. The flexible circuit 1950 is an embodiment of the flexible circuit 1915, wrapping around the inflatable member 1920. The flexible circuit 1950 comprises a plurality of tendons that are connected at a top end 1952 and a bottom end 1954. Printed on the tendons are the electrodes 1962 and the wires 1964. As the flexible circuit 1950 wraps around the inflatable member 1920 on a top flat side and a bottom flat side, the electrode array is disposed on both sides, allowing for electrode functionality from either side of the catheter 1900.

Figure 20:
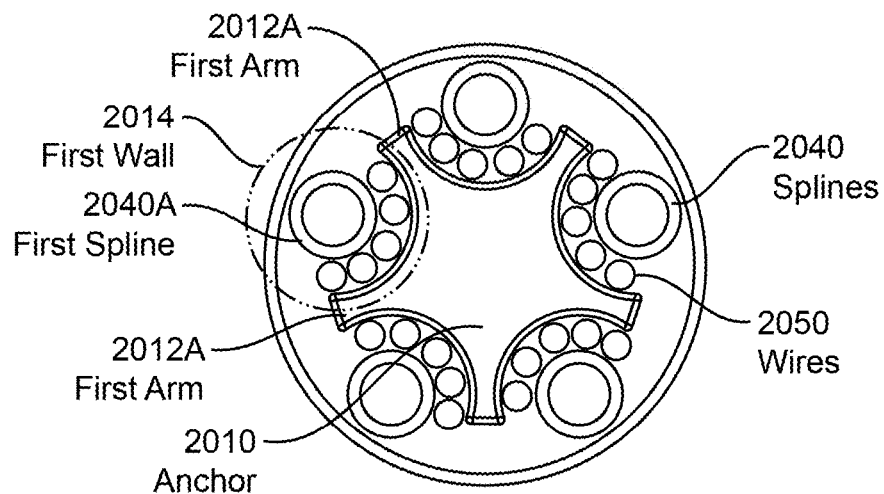
FIG. 20 illustrates cross-section views of three example anchors that may be implemented in the heart treatment device, according to one or more embodiments.
Figure 20:
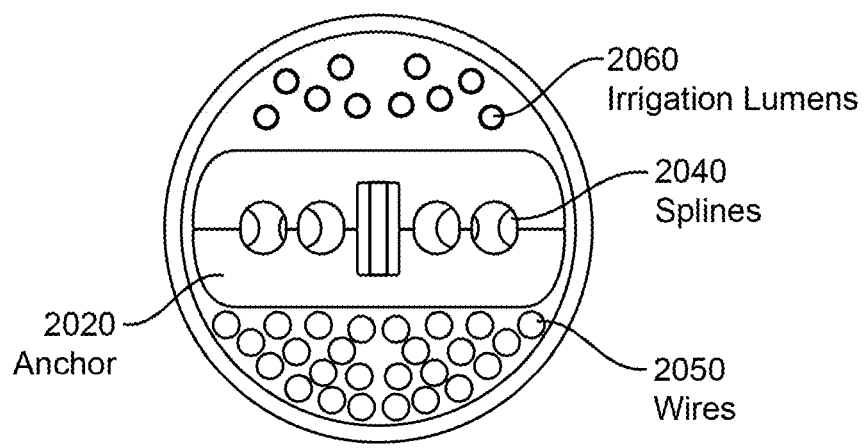
Figure 20:
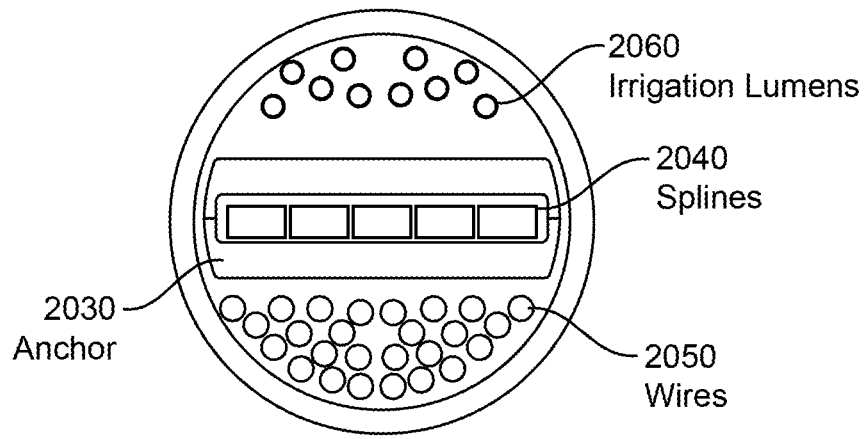

FIG. 20 illustrates cross-sectional views of three example anchors that may be implemented in the heart treatment device 105, according to one or more embodiments. The various anchors connect to the splines of the catheter 155 for securing the splines when in a compact state, i.e., when sheathed within the sheath and/or shaft of the heart treatment device 105. The various anchors described are substantially rigid, i.e., formed from a substantially rigid material. The anchors protect and ensure proper securement of the internal components routed through the shaft 150 and to the catheter 155. The anchors can also aid in the expansion and the collapse of the catheter 155 when sheathed and unsheathed during a treatment procedure.

Anchor 2010 has a star-shaped cross-sectional area. Anchor 2010 has five arms, wherein splines 2040 and wires 2050 are disposed between adjacent arms of the anchor 2010. For example there is a first arm 2012A and a second arm 2012B that extend radially from the center axis. A first well 2014 is formed between the first arm 2012A and the second arm 2012B. In the first well 2014 and against the anchor 2010 are five wires for connecting to five electrodes disposed on the first spline 2040A. The first spline 2040A rests on a side of the wires opposite from the center axis, such that the first spline 2040A and the anchor 2010 sandwich the five wires in the first well 2014. Advantages of the anchor 2010 include a strong central core that can support the splines 2040 and radial symmetry for even radial distribution of the splines 2040, which can help in certain catheter embodiments when collapsing the catheter into the sheath.

Anchor 2020 has a substantially rectangular cross-sectional outline. Anchor 2020 forms five holes that fit the splines 2040, thus securing the splines 2040 to the anchor 2020. As shown, anchor 2020 can be formed from two halves that are joined together for ease of manufacturing. As anchor 2020 has a substantially rectangular cross-sectional outline, a length of the cross-section is approximately a diameter of the shaft 150. The wires 2050 are disposed on one side of anchor 2020, whereas irrigation lumens 2060 are disposed on an opposite of anchor 2020. Anchor 2020 securely aligns the splines 2040 in a linear fashion, when view in the cross-sectional view, which helps to arrange the splines 2040 in a substantially planar manner when in the expanded state.

Anchor 2030 also has a substantially rectangular cross-sectional outline. Anchor 2030 forms a single rectangular hole that fits the splines 2040. The splines 2040 have a substantially rectangular cross-sectional area at their proximal end for securely coupling to anchor 2030. As with anchor 2020, the wires 2050 are disposed on one side of anchor 2030, whereas the irrigation lumens 2060 are disposed on an opposite side. Similarly, with anchor 2020, anchor 2030 linearly arranges the splines 2040 to maintain the splines 2040 in a substantially planar manner when in the expanded state. Anchor 2030 is also formed from two halves that are joined together. With a simplistic shape, each half of anchor 2030 is easier to manufacture, i.e., requires less steps in the manufacturing process.

Figure 21:
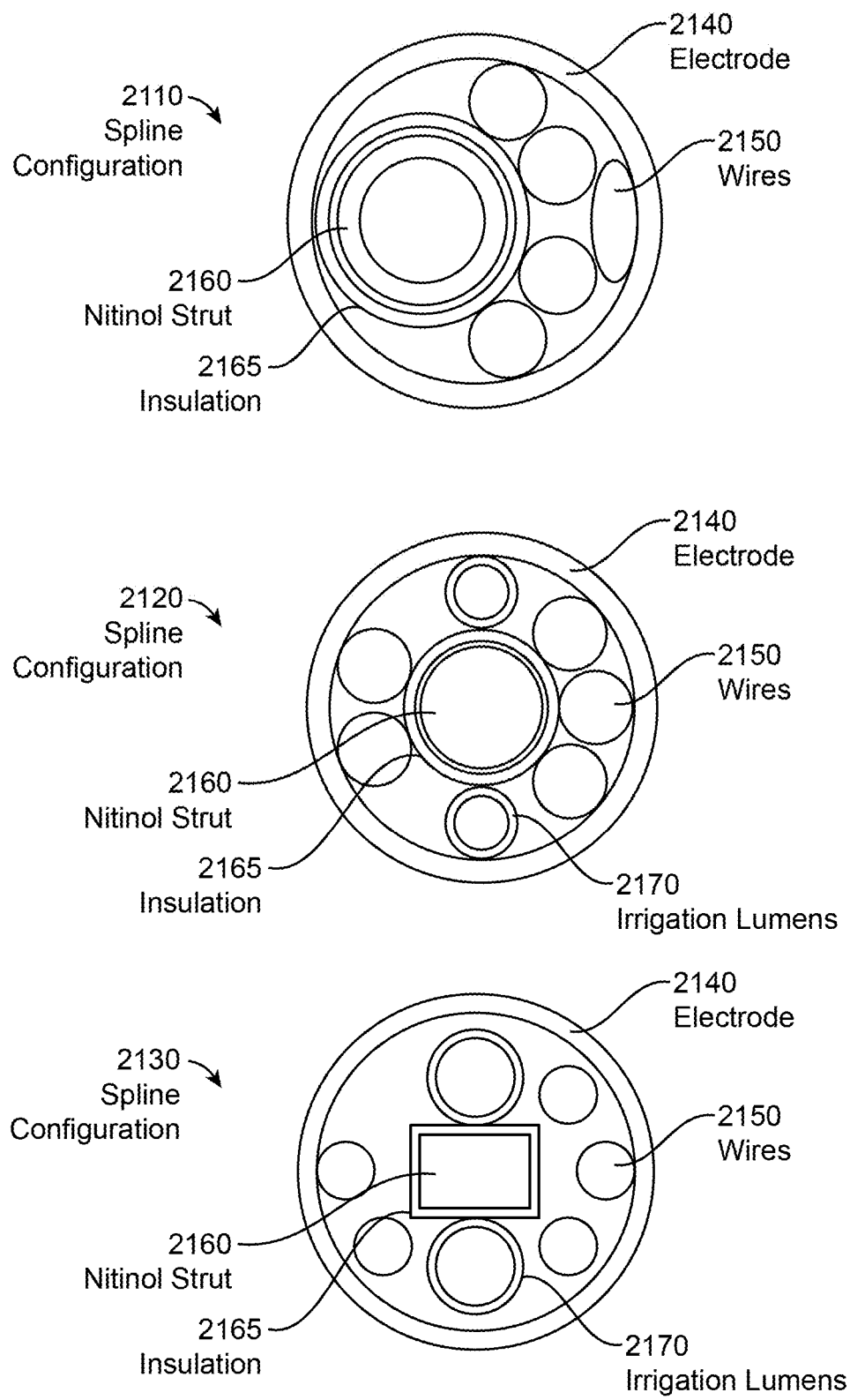
FIG. 21 illustrates cross-section views, at the proximal-most ring electrode of the catheter, of three example spline configurations that may be implemented in catheters of the heart treatment device, according to one or more embodiments.

FIG. 21 illustrates cross-sectional views, at the proximal-most ring electrode of the catheter, of three example spline configurations that may be implemented in catheters 155 of the heart treatment device 105, according to one or more embodiments.

Spline configuration 2110 includes a nitinol strut 2160 that has a center axis offset from a center axis of the electrode 2140. The electrode 2140 is circumferential around the spline to allow for ablation energy to be delivered from any point around the spline that is in contact with the electrode 2140. The nitinol strut 2160 provides structural support to the spline. The nitinol strut 2160 includes an insulation 2165 that is wrapped around the nitinol strut 2160. Wires 2150 are disposed on one half of the spline cross-sectional area.

Spline configuration 2120 includes a nitinol strut 2160 with a center axis aligned with the center axis of the electrode 2140. Two irrigation lumens 2170 are disposed on either side of the nitinol strut 2160 along a diameter of the spline's cross-sectional area. The nitinol strut 2160 provides structural support to the spline. The nitinol strut 2160 includes an insulation 1065 that is wrapped around the nitinol strut 2160. The wires 2150 are disposed around the nitinol strut 2160. In one or more embodiments, the aligned electrode and strut provides improved transitioning between a collapsed state of the catheter and an expanded state of the catheter.

Spline configuration 2130 includes a nitinol strut 2160 with a center axis aligned with the center axis of the electrode 2140. The nitinol strut 2160 has a substantially rectangular cross-sectional area. The substantially rectangular cross-sectional area may be due to the nitinol strut 2160 being laser cut from a nitinol sheet. In one or more embodiments, the splines are monolithic and laser cut from a single nitinol sheet, which ensures consistent spacing between the splines when transitioning to the expanded state. The substantially rectangular cross-sectional area may also induce preferred bending of the expanded catheter, which provides better conformability of the catheter to the anatomy of the tissue being treated. Like spline configuration 2120, spline configuration 2130 includes two irrigation lumens 2170 disposed on either side of the nitinol strut 2160 along a diameter of the spline's cross-sectional area. The nitinol strut 2160 provides structural support to the spline. The nitinol strut 2160 includes an insulation 2165 that is wrapped around the nitinol strut 2160. The wires 2150 are disposed around the nitinol strut 2160.

Figure 22:
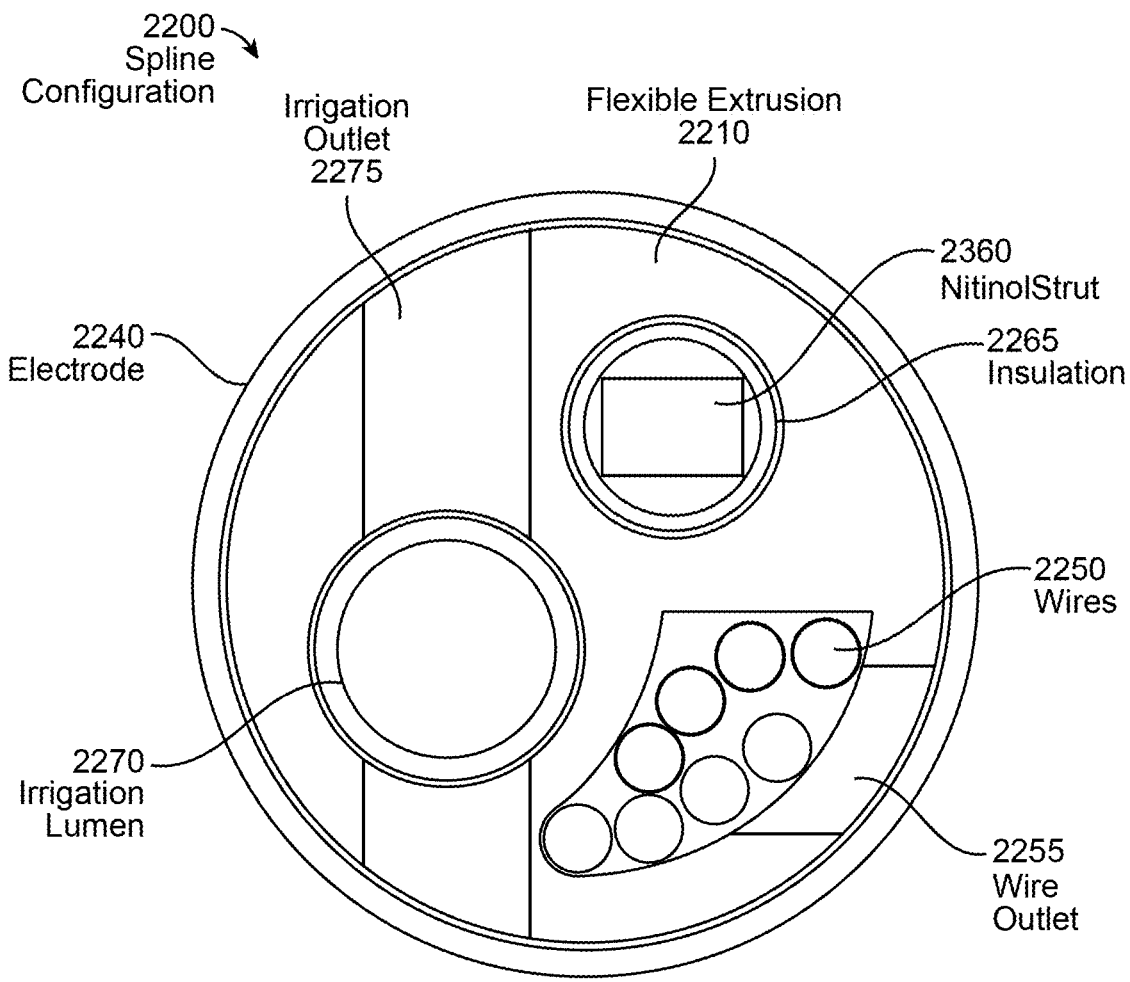
FIG. 22 illustrates a cross-section view, at the proximal-most ring electrode of the catheter, of a fourth example spline configuration that may be implemented in catheters of the heart treatment device, according to one or more embodiments.

FIG. 22 illustrates a cross-section view, at the proximal-most ring electrode of the catheter, of a fourth example spline configuration 2200 that may be implemented in a catheter 155 of the heart treatment device 105, according to one or more embodiments. The spline configuration 2200 comprises components alongside the nitinol strut 2260 that forms the various splines of the catheter 155. The spline configuration 2200 comprises a flexible extrusion 2210, an electrode 2240, wires 2250, a wire outlet 2255, the nitinol strut 2260, insulation 2265, an irrigation lumen 2270, and an irrigation outlet 2275. The flexible extrusion 2210 is flexible but provides support to the catheter when deployed. The flexible extrusion 2210 forms three cavities that run parallel to the spline. The first cavity is for fitting the flexible extrusion 2210 around the nitinol strut 2260, with insulation 2265 insulating the nitinol strut from any electrical charge. The second cavity allows for an irrigation lumen 2270 to run through the flexible extrusion 2210. One or more irrigation outlets 2275 may be disposed perpendicular to the irrigation lumen 2270. The irrigation outlets 2275 connect the irrigation lumen 2270 to one or more irrigation pores on the catheter 155. The third cavity allows for wires 2250 to run between the handle 145, through the shaft 150, to the catheter 155. The wire outlet 2255 may be disposed perpendicular to the wires 2250, to connect one of the wires 2250 to the electrode 2240.

Figure 23:
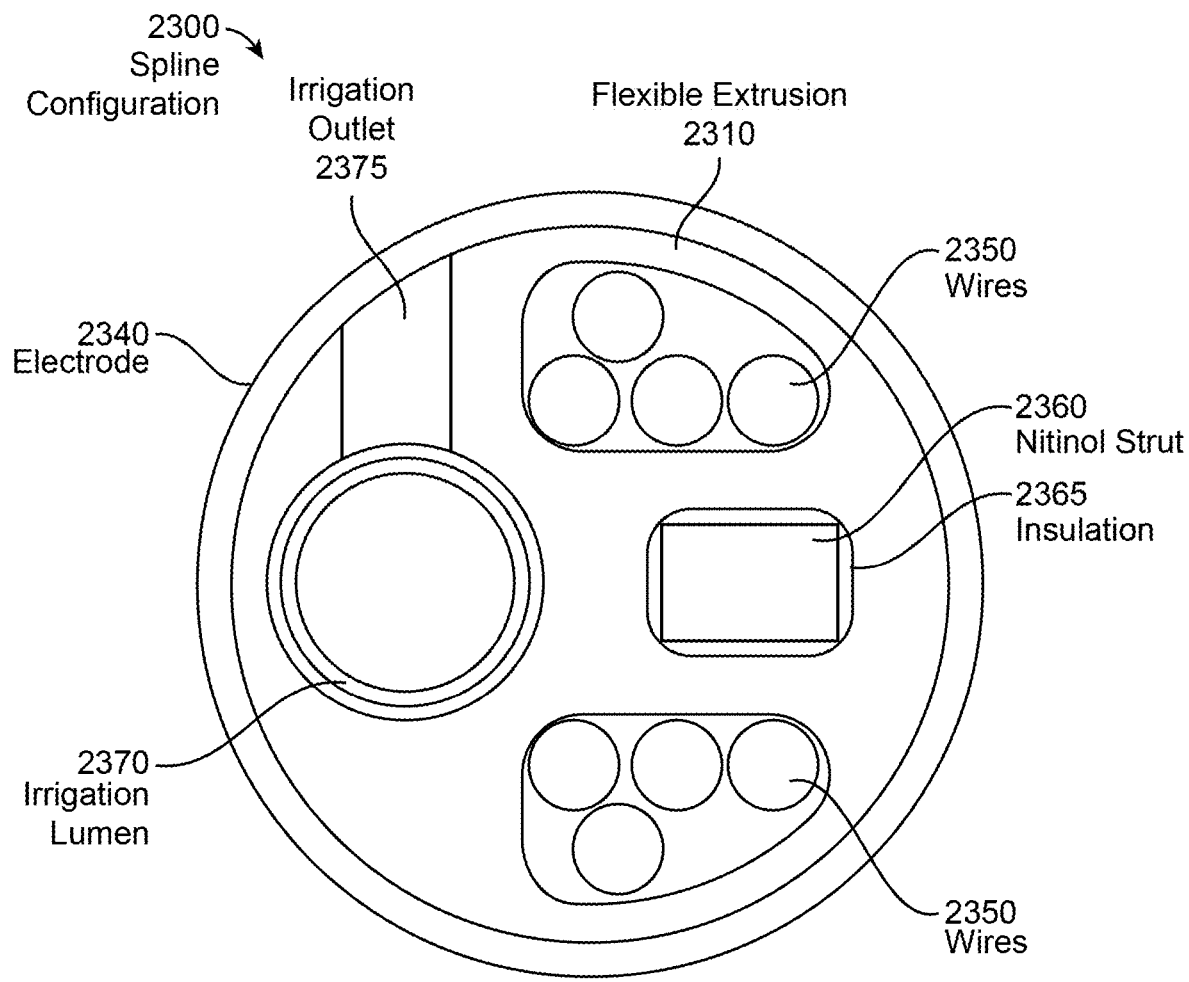
FIG. 23 illustrates a cross-section view, at the proximal-most ring electrode of the catheter, of a fifth example spline configuration that may be implemented in catheters of the heart treatment device, according to one or more embodiments.

FIG. 23 illustrates a cross-section view, at the proximal-most ring electrode of the catheter, of a fifth example spline configuration 2300 that may be implemented in a catheter 155 of the heart treatment device, according to one or more embodiments. The spline configuration 2300 comprises components wrapped around the nitinol strut 2360 that forms the various splines of the catheter 155. The spline configuration 2300 comprises a flexible extrusion 2310, an electrode 2340, wires 2350, the nitinol strut 2360, insulation 2365, an irrigation lumen 2370, and an irrigation outlet 2375. The flexible extrusion 2310 is flexible but provides support to the catheter when deployed. The flexible extrusion 2310 forms four cavities that run parallel to the spline. The first cavity is for fitting the flexible extrusion 2310 around the nitinol strut 2360, with insulation 2365 insulating the nitinol strut from any electrical charge. The second cavity allows for an irrigation lumen 2370 to run through the flexible extrusion 2310. One or more irrigation outlets 2375 may be disposed perpendicular to the irrigation lumen 2370. The irrigation outlets 2375 connect the irrigation lumen 2370 to one or more irrigation pores on the catheter 155. The third and fourth cavities allow for wires 2350 to run between the handle 145, through the shaft 150, to the catheter 155. The third and fourth cavities are disposed on opposite sides of the first cavity formed around the nitinol strut 2360.

Figure 24:
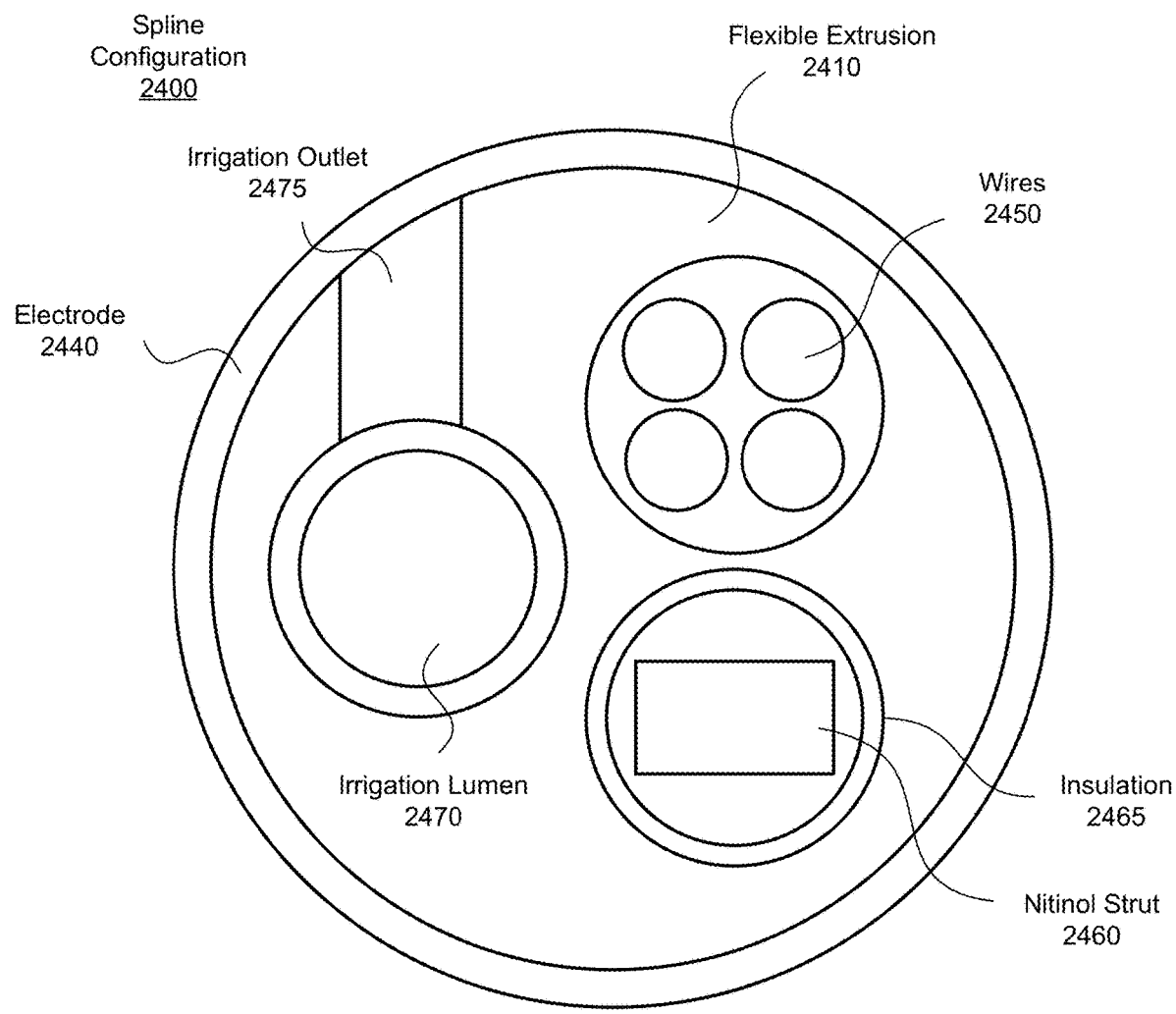
FIG. 24 illustrates a cross-section view, at the proximal-most ring electrode of the catheter, of a sixth example spline configuration that may be implemented in catheters of the heart treatment device, according to one or more embodiments.

FIG. 24 illustrates a cross-section view, at the proximal-most ring electrode of the catheter, of a sixth example spline configuration 2400 that may be implemented in a catheter 155 of the heart treatment device, according to one or more embodiments. The spline configuration 2400 comprises components wrapped around the nitinol strut 2460 that forms the various splines of the catheter 155. The spline configuration 2400 comprises a flexible extrusion 2410, an electrode 2440, wires 2450, the nitinol strut 2460, insulation 2465, an irrigation lumen 2470, and an irrigation outlet 2475. The flexible extrusion 2410 is flexible but provides support to the catheter when deployed. The flexible extrusion 2410 forms three cylindrical cavities that run parallel to the spline. The first cavity is for fitting the flexible extrusion 2410 around the nitinol strut 2460, with insulation 2465 insulating the nitinol strut 2460 from any electrical charge discharged by the electrode 2460. The second cavity allows for an irrigation lumen 2470 to run through the flexible extrusion 2410. One or more irrigation outlets 2475 may be disposed perpendicular to the irrigation lumen 2470. The irrigation outlets 2475 connect the irrigation lumen 2370 to one or more irrigation pores on an external surface of the spline configuration 2400. The third cavity allows for wires 2450 to run between the handle 145, through the shaft 150, to the catheter 155. The three cavities have substantially the same cross-section area and are approximately evenly spaced around the spline configuration 2400 cross section.

Interposer

FIGS. 25A-25D illustrate various architectures of an interposer 2540 as an electrical interface between one or more components of the treatment system. The interposer 2540 enables multifunctionality of electrodes in the heart treatment device 105, e.g., sensing of electrical signals, delivery of energy for ablation, sensing of temperature, and thus enable regulation of energy from a single electrode, or some combination thereof. Regulation of energy may be designed to maintain a target temperature (including a temperature range) or a target configuration of electrical parameters (including a range of the electrical parameters). This design enables effective ablation (see FIG. 4D) which avoids the risk of clotting of blood, charring of tissue or other issues.

Figure 25A:
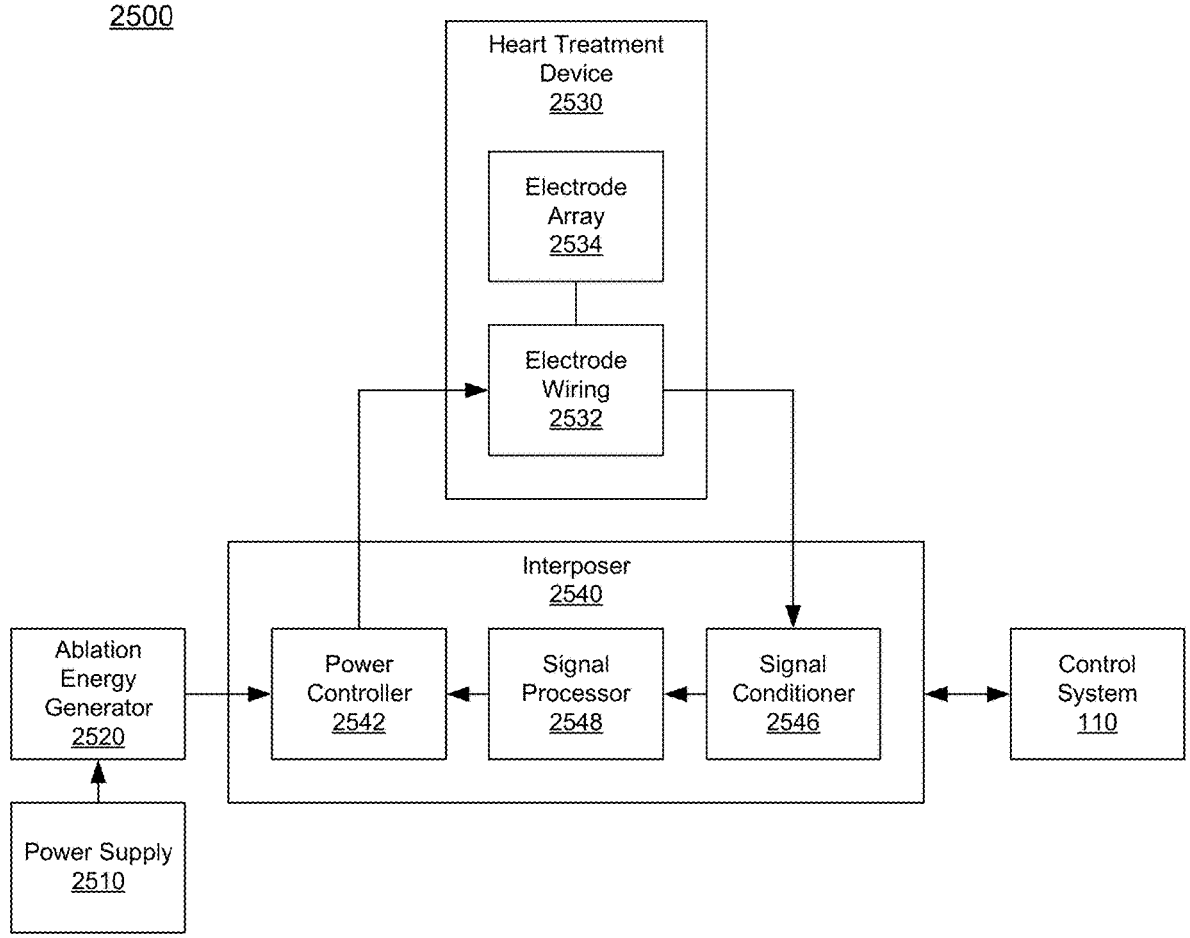
FIG. 25A illustrates a block diagram of an interposer used in conjunction with the heart treatment device, according to one or more embodiments.

FIG. 25A illustrates a block diagram of an interposer 2540 in conjunction with other components of a treatment system 2500, according to one or more embodiments. The treatment system 2500 is an embodiment of the treatment system 100 of FIG. 1. The ablation energy generator 2520 and the power supply 2510 are embodiments of the energy source 135. The heart treatment device 2530 is an embodiment of the heart treatment device 105. The interposer 2540 is an embodiment of the interposer 140. The interposer 2540 shown in FIG. 25A includes a power controller 2542, a signal conditioner 2546, and a signal processor 2548.

As an overview, the interposer 2540 coordinates electrical signals between the various components of the treatment system 100. The interposer 2540 delivers ablation energy to the electrode array 2524 of the heart treatment device 2530 via electrode wiring 2522. The interposer 2540 receives sensed electrical signals from the electrode array 2524 via the electrode wiring 2522. The interposer 2540 may modulate ablation energy delivery 2520 via a feedback loop from the sensing signals. The interposer 2540 provides one or more of the sensing signals to the control system 110, e.g., for mapping electrical activity of the patient's heart. The interposer 2540 may also modulate ablation energy delivery based on ablation instructions received from the control system 110.

Specifically, FIG. 25A depicts how signals sensed by the electrode array 2524 are routed for signal conditioning where the ablation signal from the ablation energy generator 2520 is attenuated. Attenuating the ablation signal enables temperature sensing through the same pair of wires stemming from the electrode wiring 2522. After the sensing signal is conditioned, it goes to the signal processor 2548 to convert the conditioned sensing signal into a temperature signal. In one or more embodiments, the signal processor 2548 may involve cold junction compensation and the digitization of individual electrodes. The power controller 2542 can modulate or control ablation energy delivery based on the temperature signal. Modulation of the ablation energy may involve shunting power of individual electrodes if the current temperature signal of the respective electrode exceeds the defined temperature threshold. If an individual electrode on the electrode array 2524 has temperature signals below the defined temperature threshold during therapy, no shunting occurs, and the respective electrode will receive its full ablation energy output from the ablation energy generator 2520.

The power supply 2510 provides power to the ablation energy generator 2520. The power supply 2510 may also provide power to the other components of the treatment system 2500. The power supply 2510 may comprise some regulator to adjust the electrical energy provided to the various components of the treatment system 2500.

The ablation energy generator 2520 generates ablation energy that is directed by the interposer 2540 to the heart treatment device 2530. The ablation energy may be in the form of radiofrequency waves. An example ablation energy generator 2520 generates ablation energy at 100 Volts of alternating current (VAC) at a frequency of 500 kiloHertz (kHz). In other embodiments, other types of electromagnetic waves may be used for ablation energy with different waveforms.

The heart treatment device 2530 comprises at least an electrode array 2524 and electrode wiring 2522. The electrode array 2524 comprises a plurality of electrodes that may be utilized for sensing electrical signals from tissue and ablation of regions of interest. The electrodes may be formed of conductive materials, e.g., copper, gold, platinum, other conductive metals, other conductive metal alloys, etc. The electrode wiring 2522 directs electric charge between the interposer 2540 and electrode array 2524. The electrode wiring 2522 may be formed of conductive materials, e.g., copper, gold, platinum, constantan, other conductive metals, or other conductive metal alloys. The electrode wiring 2522 may be designed such that it allows for the ability to record tissue electrical signals, temperature sense, and ablate, with temperature sensing and ablation occurring at the same time.

The power controller 2542 controls the amount of power delivered to the heart treatment device 2530. The power controller 2542 may modulate the power delivered to each electrode of the electrode array 2524 independently, thereby allowing the interposer 2540 to control how much ablation energy is delivered to the patient. Shunting may be achieved through driving current through multiple shunt resistors, which act as temporary loads. Other electrical component(s) may be utilized to serve as temporary load(s). The power controller 2542 may receive ablation instructions from the control system 110 that may indicate, e.g., a set of electrodes to deliver ablation energy, the amount of ablation energy to be delivered by each electrode of the set, a timing for delivery of the ablation energy, or other relevant control parameters.

The signal conditioner 2542 filters the electrical signals (also referred to as the "sensing signals") received from the heart treatment device 2530. In one or more embodiments, a subset of electrodes of the electrode array 2524 is configured to deliver ablation energy, e.g., conditioned from the signal conditioner 2542, while another subset of electrodes of the electrode array 2524 is configured to sense electrical signals from the tissue. The sensing signals received from the heart treatment device 2530 may be noisy due to ablation energy delivered by the first subset of electrodes operating in the ablation mode. As such, the signal conditioner 2542 filters out noise to extract the signals sensed from the tissue. In one or more embodiments, the signal conditioner 2542 comprises a passive filter and an active filter in the form of an operational amplifier. The passive filter filters out signal pertaining to ablation energy. The passive filter may be a low-pass filter that enables passage of lower frequency sensing signals while attenuating higher frequency ablation signals. The operational amplifier acts as a buffer and attenuates residual noise from the ablation energy. As an embodiment, the signal conditioner 2542 may comprise a low-pass filter which feeds into a buffer operational amplifier, (the output signal is the same as the input signal, providing further isolation from AC signal). The 500 kHz AC signal used for ablation is attenuated, forwarding to the temperature sensor 2548 the 5 μV DC signal used for temperature sensing. Alternative methods of filtering include different topologies for active and passive filtering, frequency demodulation by filtering the ablation signal, and time division multiplexing by utilizing a sample and hold circuit.

Other embodiments of the signal conditioner 2542 include demodulators, e.g., slope detectors, pulse-averaging discriminators, quadrature detectors, and phase-locked loops. Slope detectors convert frequency modulations signals to amplitude modulated signals using a passive filter e.g., inductor capacitor circuit. The signal conditioner 2542 extracts information in the form of pulses sourced from a peak detector e.g., a series connection of a diode and capacitor. Pulse-averaging discriminators utilizes a zero-crossing detector, one-shot multivibrator, and a low pass filter to recover modulated signals. Quadrature detectors employ a 90° phase shifted signal at an unmodulated frequency to allow for two distinct signals, one being the carrier wave and the second being the data signal from e.g., heart treatment device 2530. Phased-locked loops use a combination of a low pass filter and voltage-controlled oscillator to effectively compares the phase of an input signal e.g., heart treatment device 2530 to the phase of an adjustable feedback signal e.g., the output signal from the signal conditioner 2542.

Another embodiment of signal conditioner 2542 may be time division multiplexing. This approach uses a sample and hold circuit. The sample and hold circuit comprises of a frequency detector and a latching circuitry. The frequency detector samples the sensed signal to identify the various frequencies of overlapping signals. The latching circuitry holds a particular signal. The frequency detectors inform the latching circuitry to sample and hold at specific intervals relative to the input frequency of the carrier wave, thereby selectively retaining signals sensed from the tissue while ignoring noisy signals from the delivered ablation signal.

The signal processor 2548 converts this sensed voltage into a temperature signal. The electrode wiring 2522 produces a temperature-dependent voltage due to the Seebeck effect. Also, the signal processor 2548 receives the output signal from the signal conditioner 2542 and provides cold-junction compensation and digitizes the signal, e.g., for the control system 110. The power controller 2542 utilizes the temperature signal to modulate delivery of the ablation energy. The signal processor 2548 may also provide additional filtering to further attenuate any ablation energy signal. The signal processor 2548 may also provide the sensed signals, including the temperature signal to the control system 110.

Figure 25B:
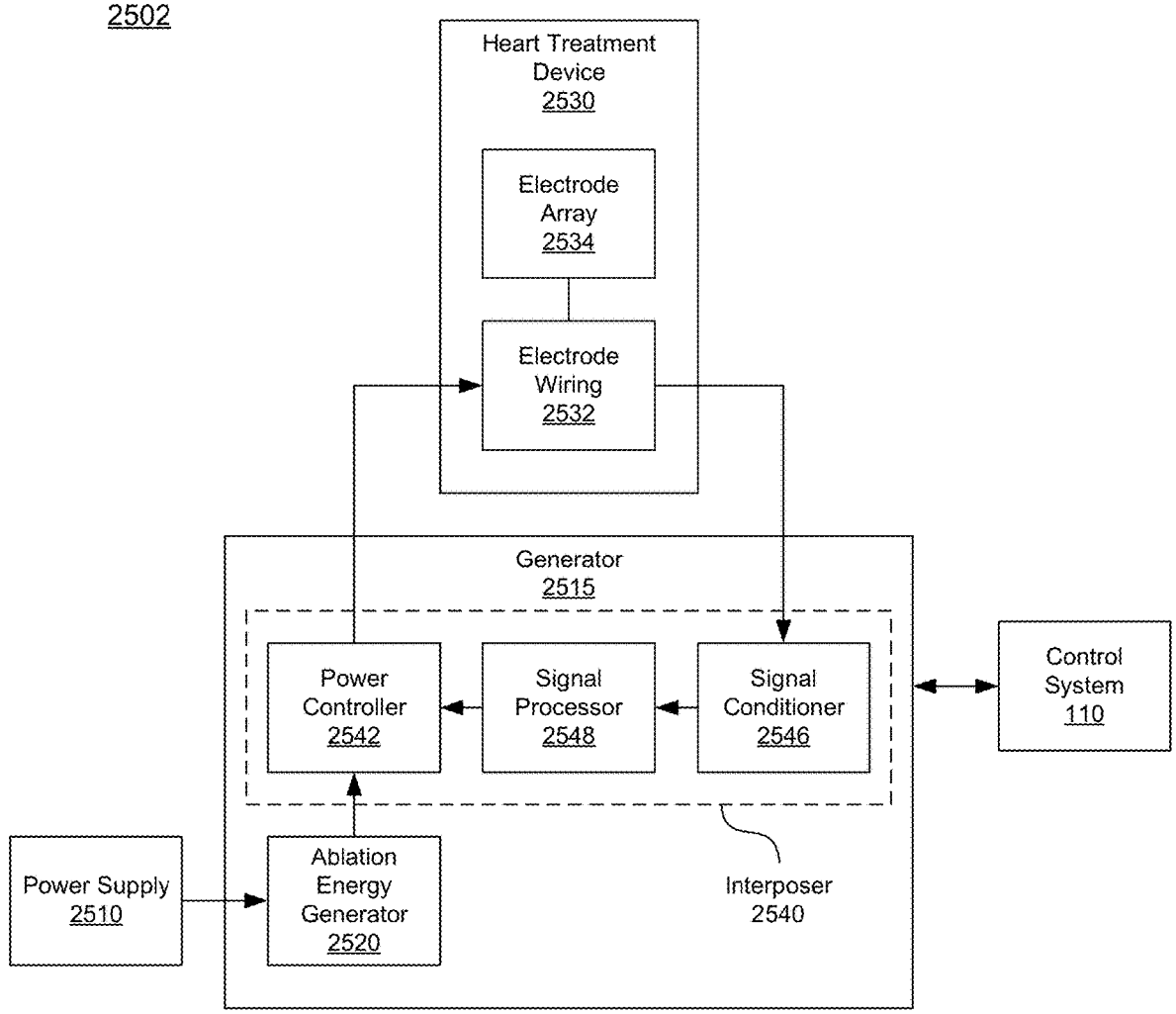
FIG. 25B illustrates a block diagram of a generator including an ablation energy generator and an interposer, according to one or more embodiments.

FIG. 25B illustrates a block diagram of a generator 2515 including an ablation energy generator 2520 and an interposer 2540, according to one or more embodiments. The diagram primarily illustrates electrical components. The generator 2515 is an embodiment of the generator 115. The interposer 2540 is an embodiment of the interposer 140. In the embodiment shown in FIG. 25B, the generator 2515 incorporates both the ablation energy generator 2520 and the interposer 2540, and may be considered an integrated closed loop system generator. In such embodiments, the generator 2515 connects to the power supply 2510. The ablation energy generator 2520 draws power from the power supply 2510 to generate the ablation energy to be provided to the heart treatment device 2530.

Figure 25C:
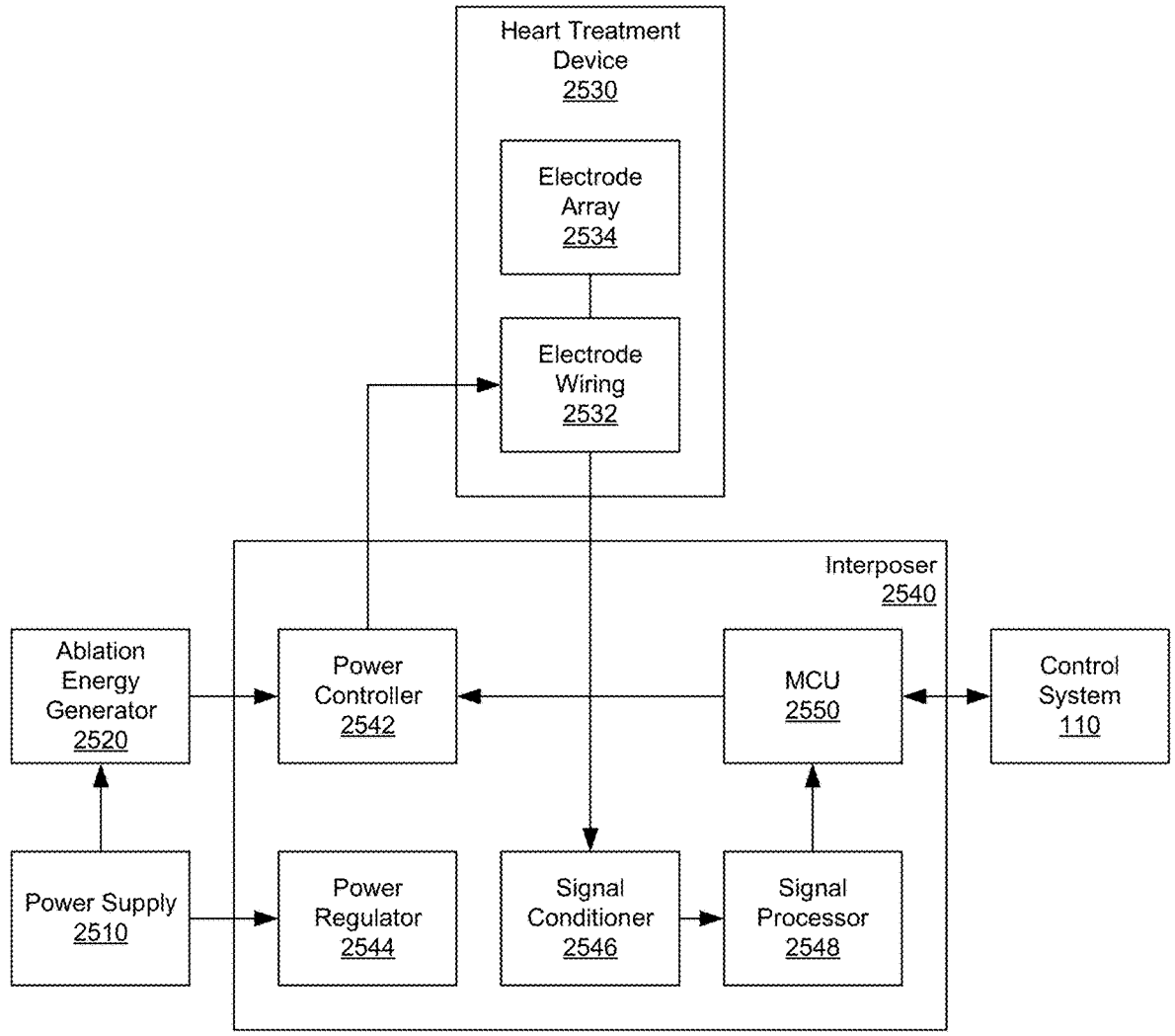
FIG. 25C illustrates a block diagram of the interposer used in conjunction with the heart treatment device, according to one or more embodiments.

FIG. 25C illustrates a block diagram of an interposer 2540 in conjunction with other components of the treatment system 2504, according to one or more embodiments. The diagram primarily illustrates electrical components. The interposer 2540 is an embodiment of the interposer 140. In the embodiment shown in FIG. 25C, the interposer 2540 includes the power controller 2542, the power regulator 2544, the signal conditioner 2546, the signal processor 2548, and a microcontroller unit (MCU) 2550.

The power supply 2510 provides power to the ablation energy generator 2520. The power supply 2510 may also provide power to the other components of the treatment system 2500. The power supply 2510 may rectify the 120V AC supplied by the wall outlet to an output of 12V of direct current (VDC).

The MCU 2550 is a centralized controller for coordinating operation of the components of the interposer 2540. The MCU 2550 receives the temperature signal from the signal processor 2548 to determine whether the tissue is within a safe temperature tolerance. If the tissue is heated beyond the safe temperature tolerance, the MCU 2550 initiates ablation energy modulation via the power controller 2542. The MCU 2550 may send pulse width modulated signal to the power controller 2542 instructing how long to shunt the ablation energy. As an example, the MCU 2550 will enable or disable two independent solid-state relays per electrode to modulate the power delivered to the electrode. The shunting algorithm may coordinate modulation of power across the electrodes configured for ablation, e.g., if there are hot zones.

The MCU 2550 also outputs sensed electrical signals to the control system 110. The MCU 2550 directs sensed electrical signals that are filtered by the signal processor 2546 to the control system 110. The control system 110, as described in FIG. 1 or further in FIG. 26, can map out the sensing signals to guide treatment by the heart treatment device 105. The control system 110 can also provide the MCU 2550 with ablation instructions that may modify the control signals provided to the power controller 2542.

Figure 25D:
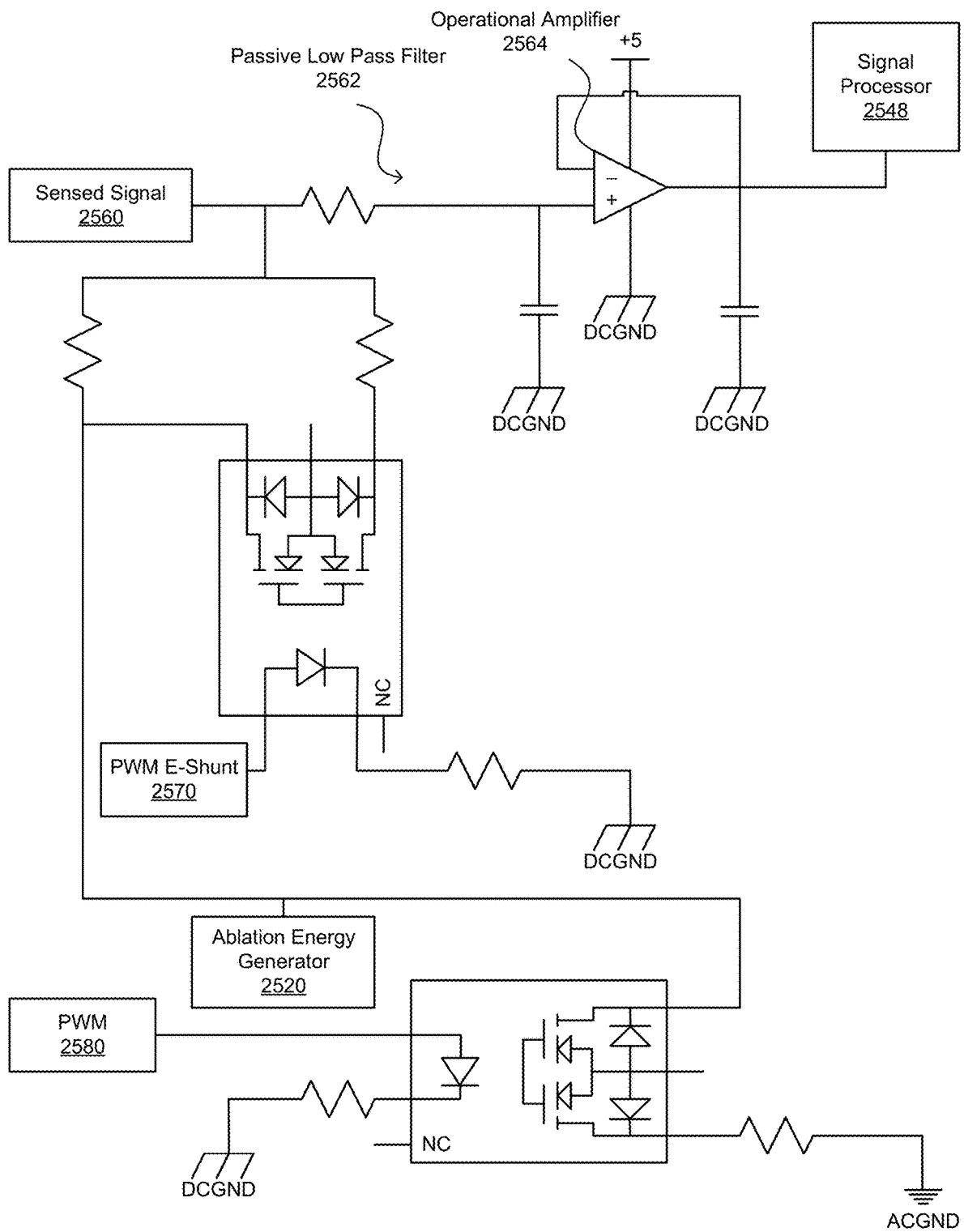
FIG. 25D illustrates a circuit diagram of the signal conditioner of the interposer of FIGS. 25A-25C, according to one or more embodiments.

FIG. 25D illustrates a circuit diagram of the signal conditioner 2546 of the interposer 2540 of FIGS. 25A-25C, according to one or more embodiments. As shown in FIG. 25D, the sensing signal 2560 received from the heart treatment device 2530 passes through a passive low pass filter 2562, e.g., with a cutoff frequency of ~15.9 Hz, to an operational amplifier 2564 that further attenuates the high-frequency ablation energy signal, such that the signal processor 2548 can read the DC voltage of the sensing signal 2560 used by the signal processor 2548 to measure a temperature signal. The signal processor 2548 provides the temperature signal to the MCU 2550 (not shown), which controls a PID loop that modulates ablation energy delivered to the heart treatment device 2530 from the ablation energy generator 2520. The PID loop includes a PWM E-Shunt 2570, a PWM 2580, and two integrated circuits. PWM E-Shunt 2570 and PWM 2580 are pulse width modulated signals with an amplitude of 5V and a frequency of 32 kHz that signal to the power control when to independently control two solid state relays. When PWM 2580 is enabled, the associated solid-state relay would toggle shunting ablation energy every 15.8 µs for the respective electrode. PWM E-shunt has the same amplitude and frequency as PWM but controls the series resistance of the electrode from either being 83.33Ω when enabled or to 500Ω when disabled. The integrated circuits (being solid-state relays) are fundamentally switches that are controlled by a digital signal i.e., PWM 2580 and PWM E-Shunt 2570. When the solid-state relay receives a digital high signal, being 5V, it closes the circuit. When the solid-state relay receives a digital low signal, being 0V, the circuit opens. These electrical parameters are illustrative of sample embodiments, and other ranges are feasible.

Control System

FIG. 26 illustrates a block diagram of the control system 110 used in conjunction with the heart treatment device 105, according to one or more embodiments. The control system 110 manages and controls the various components of the treatment system 100. The control system 110 may be a general computing system, one embodiment of which is described in FIG. 30. The control system 110 includes various modules including, but not limited to, a generator interfacing module 2610, an irrigation pump interfacing module 2620, an electrical signal processing module 2630, a patient profiler 2640, a catheter optimization module 2650, a guidance model 2660, an ablation treatment model 2670, a treatment assessment model 2680, and a data store 2690. In other embodiments, additional or fewer modules may be implemented.

The generator interfacing module 2610 interfaces with the generator 115. In interfacing the generator 115, the generator interfacing module 2610 is configured to receive electrical signals from the generator 115 as measured by the electrode array of the catheter 155 of the heart treatment device 105. The electrical signals may be separated for each electrode of the electrode array. The generator interfacing module 2610 provides the electrical signals received from the generator 115 to the electrical signal processing module 2630. In addition, the generator interfacing module 2610 is configured to provide the generator 115 with instructions on performing an ablation procedure. The instructions can include a plurality of parameters for the ablation procedure. Example parameters may include, which electrodes to actuate during the ablation procedure, and for each electrode to be actuated for the ablation procedure, a frequency of the ablation energy, a waveform of the ablation energy, and a duration of the ablation energy.

The irrigation pump interfacing module 2620 interfaces with the irrigation pump 120. The irrigation pump interfacing module 2620 is configured to provide instructions on performing an ablation procedure to the irrigation pump 120. The instructions relevant to the irrigation pump may include which irrigant to use (in embodiments with multiple irrigants stored by the irrigation pump 120), how much irrigant to pump, for a particular duration, etc.

The electrical signal processing module 2630 processes the electrical signals measured by the electrode array of the catheter 155. The electrical signal processing module 2630 may perform one or more pre-processing techniques. Some example pre-processing techniques include noise filtering, annotation of the electrical signals, determining whether to discount a particular electrical signal due to recording artifacts, etc. In embodiments with other sensing devices, e.g., a non-invasive device with a wearable electrode array, the electrical signal processing module 2630 may also process the electrical signals measured by the other sensing devices.

The patient profiler 2640 maintains a patient profile for each of a plurality of patients. Each patient profile may include identifying information and medical records. Identifying information may include name, biological sex, age, one or more current and/or prior medical conditions (e.g., asthmatic, diabetic, etc.). The medical records may include one or more prior diagnoses, one or more types of heart rhythm disorders that the patient has, one or more prior procedures, drug allergies, prior data streams, prior electrical signal data associated with a prior procedure, a current diagnosis, etc. The patient profiler 2640 may routinely update the patient profile upon the completion of a procedure. In one or more embodiments, the catheter optimization module 2650 selected a particular sized catheter with a particular sized electrode array for use in a given patient.

The ablation procedure was successful for treating the patient's heart rhythm disorder. In response, the patient profile 1040 stores the selected catheter with the annotation of the procedure being successful. In a subsequent procedure, the patient profile including the prior success with the prior selected catheter can inform which catheter to select in the subsequent procedure.

Figure 27:
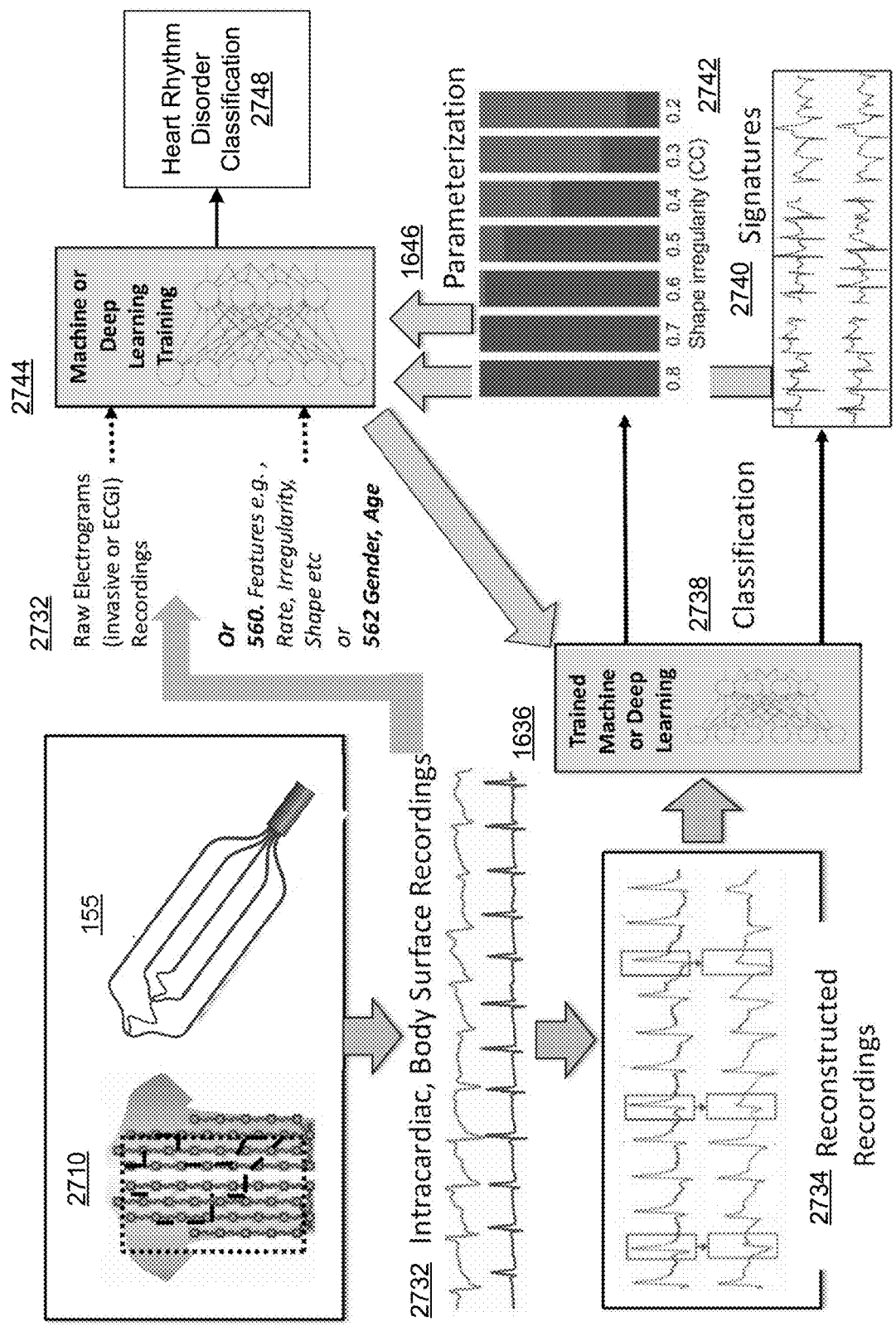
FIG. 27 illustrates machine learning and classification algorithms that may be used in conjunction with the sensing and ablation catheter in one or more embodiments. This may use data from other sensing equipment including other invasive catheters or non-invasive recordings.

In some embodiments, the electrical signal processing module 2630 extracts features from the electrical signals for use by other modules of the control system 110. Referring to FIG. 27, FIG. 27 illustrates one method 2736 of extracting specific rhythm signatures 2740 and shape irregularity 2742 from electrical signals 2732 measured by a sensing device (e.g., the electrode array of the heart treatment device 105 or an electrode array of another non-invasive sensing device). The features can be used to classify the rhythm, or identify special regions and/or special times within the rhythm disorder (e.g., by the guidance model 2660). These special times and/or regions can be treatment targets. In one or more embodiments, a non-invasive sensing device 2710 and/or electrical signals 2720 from the catheter 155 are used to generate the intracardiac and/or body surface recordings 2732. The electrical signal processing module 2630 can further reconstruct the recordings 2732 into the reconstructed recordings 2734. The algorithm 2736 for feature extraction is applied to these specific signals to extract the features, e.g., to create fingerprints or footprints or signatures 2740 of the rhythm. The extracted features may be useful in refinement of the identification of the location of rhythm to classify right or left atrial or right or left ventricular origin. This can be structured to identify pulmonary vein from non-pulmonary vein regions for different embodiments. This can be useful to separate conditions such as atrial flutter from fibrillation, which guides therapy. This can also be useful to separate different forms of atrial fibrillation, such as those which can be treated by pulmonary vein isolation compared to forms that require therapy at additional areas outside the pulmonary veins. Similar algorithmic processes may be for other types of rhythm disorders that are not related to hearts, such as for seizure disorder in the brain, activity in the gastrointestinal tract, or nerve firing in a portion of the body in neurological illness.

The signatures 2740 may also identify a signal type that is a treatment target for the heart rhythm disorder, such as a region of slow conduction, of a viable channel of tissue within scar, or fractionated signals, of high rates, of source or driver activity and so on. The signatures 2740 may or may not be clear from analyses of the time-domain characteristics of the signal, such as amplitude, rate or shape. The signatures 2740 may or may not be clear from analyses of the frequency domain characteristics of the signal, such as frequency, harmonics or phase. The signatures 2740 may extend to signals from neighboring electrodes to form a preferred spatial region or cluster.

FIG. 27 further illustrates a method 2744 of classifying a heart rhythm disorder of the patient. The method 2744 implements one or more models, such as a classification model, to determine a type of heart rhythm disorder that is present in a given patient. The classification model inputs raw electrical signals, i.e., the recordings 2732, the reconstructed recordings 2734, the rhythm signatures 2740, the shape irregularities 2742, other data described herein this disclosure, or some combination thereof. The parameters of the model used in the method 2736 to extract the signatures can further serve as parametric information 2746 to inform training of the classification model. The classification model 2744 outputs a heart rhythm disorder classification 2748 which identifies a particular type of heart rhythm disorder. The heart rhythm classification 2748 may inform which patterns to look out for in the electrical signals, as each heart rhythm disorder may have unique patterns.

In some embodiments, pre-processing may include high-pass filtering above 0.5 Hz to remove baseline oscillation or other artifacts, but others can be selected. In another embodiment, pre-processing can include low-pass filtering to remove electrical noise or other artifacts. Filtering can include also narrow-band pass filtering at spectral band determined by features of the signal under analysis or other signals. For instance, some important features of AF in the frequency domain can be identified in bands of 0-20 Hz, such as the frequency of the main or secondary spectral contributions, their width and relative amplitude as well as the relative spectral content for certain frequency bands compared to the total spectral content. These features could be considered when selecting filters for signal acquisition. An embodiment could also use ventricular activity cancellation when the aim is to identify origin regions from the atrial chamber. In some embodiments, the ventricular cancellation algorithm is based on detection of the instant of ventricular depolarization using a combination of linear and non-linear filtering and identification of local maxima. The ventricular cancellation algorithm could be based on ventricular shape average and subtraction using one or more torso signals. The ventricular cancellation algorithm could be based on partial component analysis using different ventricular beats.

The electrical signal processing module may perform spectral analysis of the torso signals, using the Fast Fourier Transform, the Welch Periodogram, convolutional-based transform or the continuous wavelet transform. The spectral analysis could be also based on the combination of spectral transformations after different linear or non-linear filtering, such as band-pass filtering or Bottteron and Smith filtering.

The spectral analysis could be used to detect the main spectral contribution using the following formula:

$$DF = \vartheta(s_{ECG})|_{\vartheta(s_{ECG})=max(\|\vartheta(s_{ECG})\|)}$$

In the above equation, DF is the main spectral contribution or Dominant Frequency, $s_{ECG}$ is the surface signal under analysis and $\vartheta(s_{ECG})$ represents the spectral transform by Fast Fourier Transform or Welch Periodogram. The electrical signal processing module may perform identification or other secondary spectral contribution using the local maxima of the spectral transform. The electrical signal processing module may perform analysis of the spatial distribution of the DF values in order to identify regions with the same or different values of DF.

The electrical signal processing module may perform analysis of the phase of the surface signal, using the following or other formula:

$$\text{phase}(t) = \arctan(\text{imag}(\text{hilbert}(s_{ECG}(t))), \text{hilbert}(s_{ECG}(t)))$$

In the above equation, phase(t) is the instantaneous phase transform of the signal under analysis $s_{ECG}$, and imag( ) and hilbert( ) represents the imaginary-part extraction and Hilbert transform functions respectively. The electrical signal processing module may perform the analysis of the phase from individual signals, by identifying the fiducial points such as local maxima or transitions from/to pi/−pi. The electrical signal processing module may perform the analysis of several instantaneous phase signals in spatial maps, using spatial interpolation of the phase signal in each instant and position to cover all the surface torso between electrodes of the electrode array. This spatial interpolation could be carried out using linear interpolation, cubic splines or other interpolation methods, and could be carried out without the use of torso anatomies and shapes extracted from medical image (MRI, CT) techniques. The electrical signal processing module may perform the analysis of the instantaneous phase maps through the identification of the phase transitions, that is, the lines in which the phase map transits from pi to −pi.

The electrical signal processing module 2630 may perform the analysis of spatial phase singularities using the following formula:

$$\text{singularity}(t) = \oint_{0,D}^{2\pi} \text{phase}(t)_{x,y}$$

In the above equation, the operator $\oint_{0,D}^{2\pi}$ represents the spatial integral over a circle with radius D and $s_{ECG}(t)_{x,y}$ is the electrocardiographic signal at interpolated coordinates X and Y. The computing server may perform identification of instants and points in which the singularity(t) provides values different to 0 and summarize and cluster them to measure the spatial and temporal complexity of heart arrhythmia. The computing server may perform the analysis of the temporal features of the electrocardiographic surface signal as the number of local maximal after band-pass filtering. The computing server may perform the analysis of the first and second derivatives of the torso surface signal in order to identify their percentiles and quartiles. The computing server may perform autocorrelation analysis of the electrocardiographic surface signals.

The catheter optimization module 2650 determines optimal specifications for the catheter 155 for performing a procedure on a given patient. The catheter optimization module 2650 analyzes data associated with a given patient to determine the optimal specifications for the catheter 155. For example, based on the electrical signals measured for a patient (e.g., by an electrode array of the heart treatment device 105 or another non-invasive sensing device), the catheter optimization module 2650 determines an optimally sized catheter having an electrode array with a particular arrangement and a particular resolution. Some or all of the other data described herein this disclosure (e.g., the rhythm signatures 2740 or other features extracted from the method 2736) can be considered in a model to determine the optimal specifications. In some embodiments, the model comprises a plurality of decision trees to determine the optimal specifications. In other embodiments, the model is a machine learned model. A catheter 155 may be specially manufactured according to the optimal specifications. In other embodiments, a catheter 155 may be selected from a set of manufactured catheters, each having unique specifications, wherein the selected catheter 155 has specifications that closely match to the optimal specifications determined. A physician implements the selected catheter 155 for use in the heart treatment device 105.

Figure 28A:
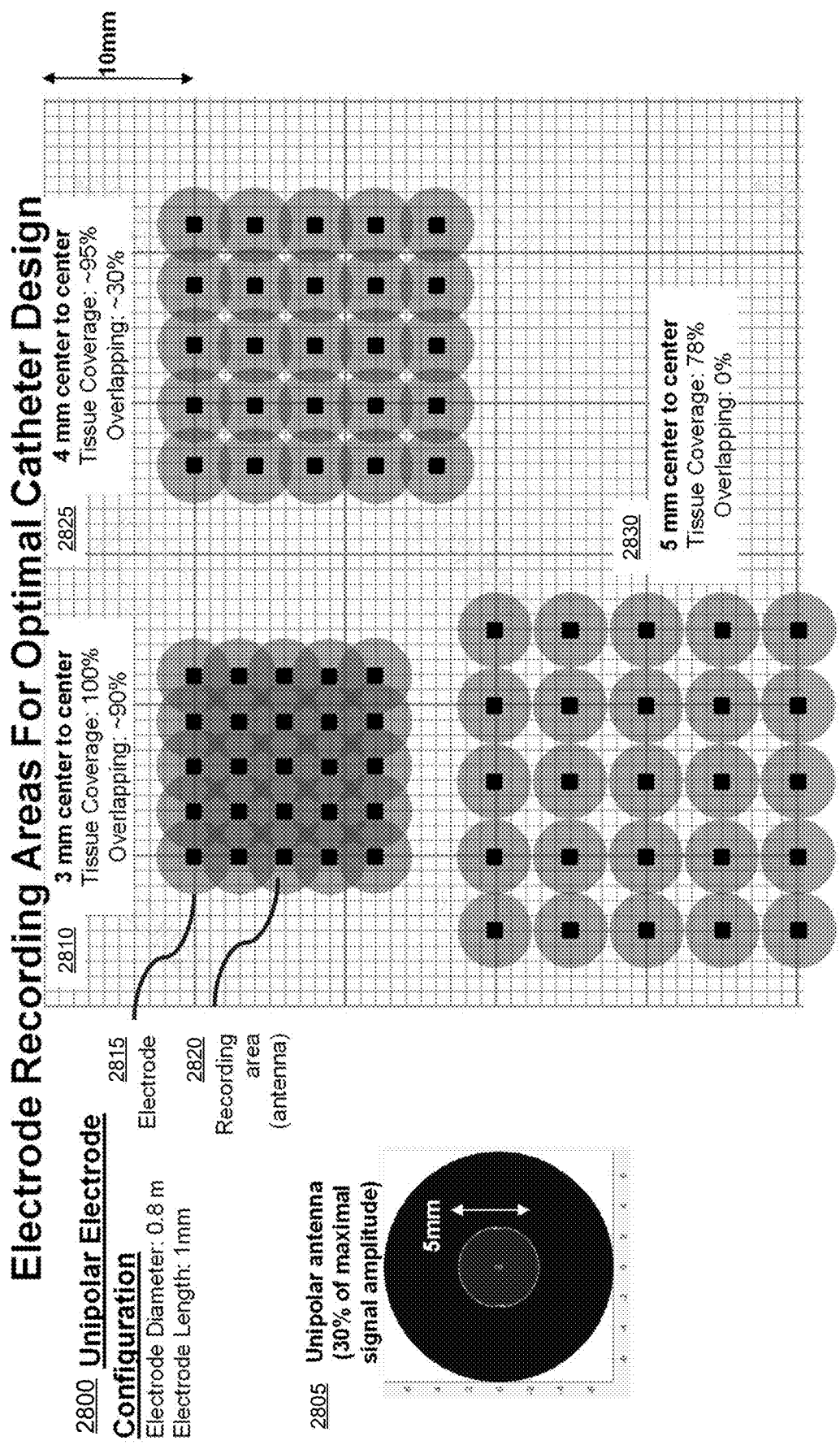
FIG. 28A illustrates the electrode array optimization for unipolar sensing configurations, according to one or more embodiments.
Figure 28B:
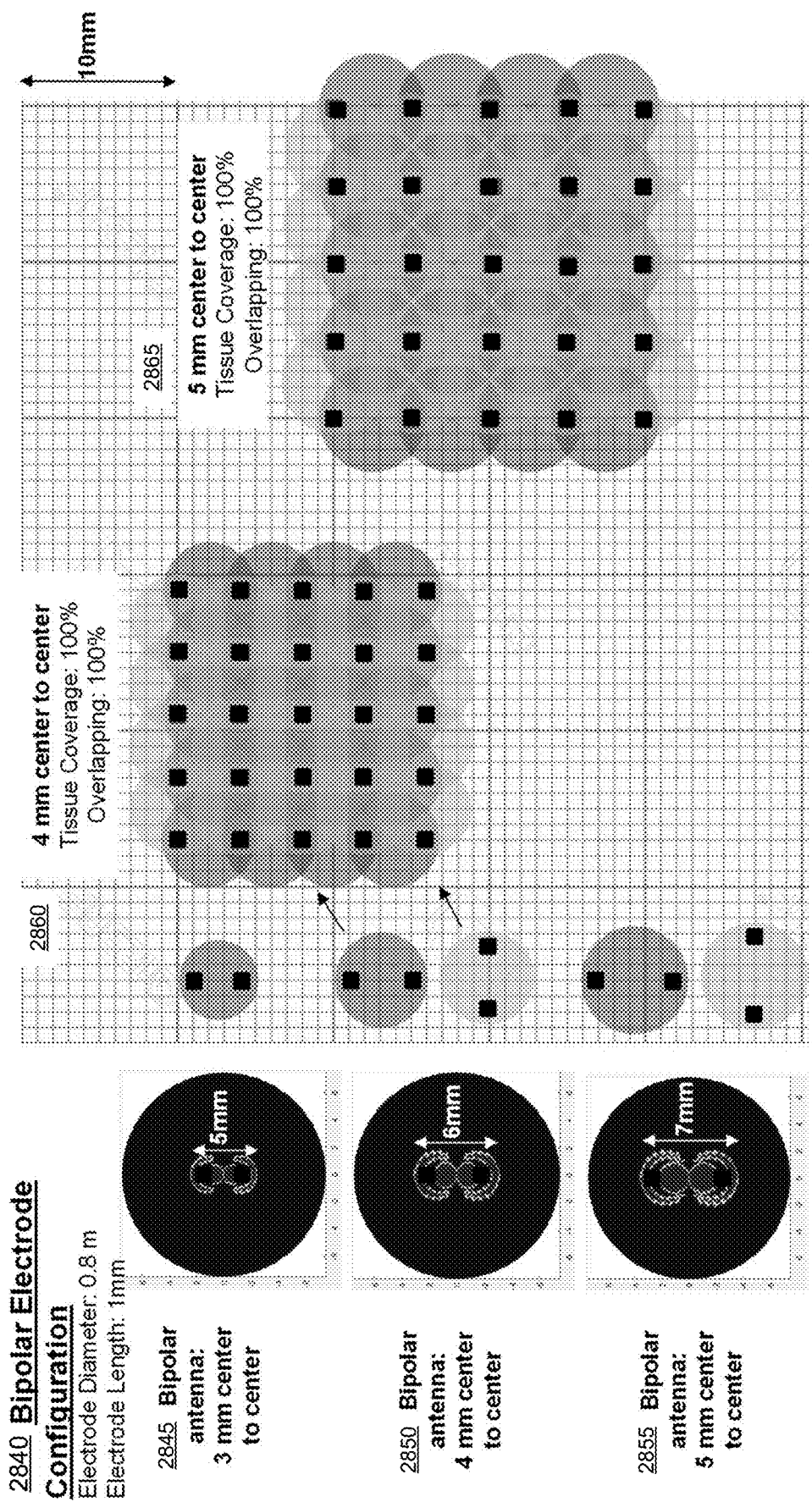
FIG. 28B illustrates the electrode array optimization for bipolar sensing configurations, according to one or more embodiments.

FIG. 28A-28C illustrate mathematical approaches used to optimize the electrode array size and configuration for optimal electrode array catheter design. FIG. 28A illustrates the electrode array optimization for unipolar sensing configurations. Each figure panel represents for heart tissue the results of numerical simulations based on known biophysical properties of electrical propagation, the extent of the recording area (or 'antenna') from each electrode, and how combining them in various configurations will alter the amount of tissue mapped and potentially the percentage of missing areas. This is compared to the known patterns of various biological rhythm disorders and other patient data, to derive an optimal electrode configuration for the preferred catheter in each patient.

Unipolar electrode configurations (panel 2800), in which each single electrode in the array is compared to an indifferent remote electrode (typically the Wilson Central Terminal). For the embodiment in FIG. 4 (electrode 0.8 mm across, 1.0 mm long), panel 2805 indicates an antenna of 5 mm for a drop of amplitude of sensing signals by the inverse square law to <30% of maximum. Panel 2810 show that for a center-to-center electrode spacing (also referred to as an "antenna distance") of 3.0 mm and 5×5 electrodes (FIG. 4), there is 100% coverage of tissue with no missed patches, for an area of 1.8×1.8 cm². This is one preferred embodiment which will be sufficiently large to map critical regions of AF and VT at very high spatial resolution, with good coverage by ablation which should ensure good therapeutic success.

Panel 2825 shows that a 4.0 mm center-to-center spacing provides 2.0×2.0 cm² area of sensing (and ablation), with ~95% tissue coverage (i.e. 5% drop-off). Panel 2830 shows that 5.0 mm center to center spacing provides only 78% tissue coverage, which may leave sufficient tissue unmapped, or unablated, so as to be suboptimal. However, if higher ablation depths are applied, then this design may also work.

FIG. 28B illustrates the electrode array optimization for bipolar sensing configurations. As shown, the antennas range from 5-7 mm shown in panels 2845, 2850, and 2855, and the impact of varying electrode spacing is shown. One drawback of bipolar electrode configurations is that they are sensitive to direction, and so for spatially varying arrhythmias such as atrial fibrillation or ventricular fibrillation there could be dropouts in sensing. However, there is good tissue coverage because the adjacent bipoles span all tissue between electrodes, albeit with less resolution as the bipoles become more widely spaced. Panel 2860 illustrates the electrode array configuration using antenna distance of 4 mm. Panel 2865 illustrates the electrode array configuration using antenna distance of 5 mm.

FIG. 28C illustrates the analogous parameters for irregularly spaced electrode configurations with a dense central cluster and a more sparse peripheral region. This could be used to provide high resolution at the central mapping region, which providing potentially better directional navigation (with less area coverage and some gaps) by peripheral electrodes. Panel 2875 describes a central cluster of electrodes having an antenna distance of 3 mm. Panel 2880 describes peripheral electrodes having an antenna distance of 6 mm. Panel 2885 illustrates a unipolar configuration using the exampled antenna distances in panels 2875 and 2880. Panel 2880 illustrates a bipolar configuration using the exampled antenna distances in panels 2875 and 2880.

In some embodiments, directional guidance is tailored by patient data beyond recorded signals. These data may include clinical, pathophysiological, laboratory, genetic or cellular elements. As an example, critical regions for AF may lie near the pulmonary veins in patients with early stage disease, yet lie away from the pulmonary veins in patients with advanced disease, heart failure or obstructive sleep apnea. Several other profiels profiles can be defined. Similarly, critical regions for ventricular tachycardia may reside in the left ventricle in patients with heart failure from coronary disease, yet in the right ventricle in patients with arrhythmogenic cardiomyopathy or advanced lung disease.

In some embodiments, techniques such as machine learning can classify an individual's data profiles based on patterns associated with response to therapy or lack of response to therapy. Machine learning may be trained by objective and clinically relevant labels such as successful response to therapy (e.g., elimination of AF by PVI ablation, elimination of VT by ablation, improvement in left ventricular ejection fraction by ablation of heart rhythm disorder), or adverse response to therapy (e.g., prolongation of the QT interval by pharmacological agents, failure from to ablation). The machine learning model can now make a prediction for an individual from their closest pattern match.

By using machine learning, the system individualizes treatment and does not cater just to the statistical majority of individuals who respond to a therapy, or to populations most represented in the literature. This is a practical implementation of FAIR software methods (Findable, Accessible, Interoperable, and Reusable) to reduce bias—for instance, to cater therapy to an individual even if they differ demographically or physiologically from the 'average' patient in prior reported populations. This enables machine learning in this invention to be broadly generalizable to under-represented minorities even if training data is from a narrow population (e.g. Caucasians).

Personalization can be encoded by computer and analytical methods based on associative algorithms, data clusters including unsupervised machine learning, semi-supervised machine learning, and supervised machine learning and networks trained by labeled events in similar and dissimilar individuals. The tailoring of personal digital records to therapy is enabled by partitioning data with labels of 'healthful vs disease', 'responsive to therapy vs non-responsive', or multiclass response to therapies labeled such as 'therapy 1', 'therapy 2', . . . , 'therapy n'. Analysis can be one or more of supervised machine learning, neural networks, unsupervised machine learning, cluster analysis, correlation analyses, logistic regression analyses, decision trees, time domain analyses, frequency domain analyses, trigonometric transformations, and logarithmic transformations.

Personalization for heart rhythm may use signals that capture the rhythm. This may include electrical potentials (electrograms) from a non-invasive device or invasive device within or adjacent to the heart. Other signals that can be analyzed include heat (infrared), mechanical motion (piezoelectric or other sensors), chemical composition, blood flow and pressure (hemodynamics), wall tension (cardiac contractility and relaxation), Cardiac Images (magnetic resonance imaging, computed tomography), or other indices that may have diagnostic value. More detailed data includes three-dimensional anatomical and structural abnormalities. Clinical data can be extracted from history and physical examination, indices of pathophysiological comorbidities, blood and tissue biomarkers, and genetic and cellular makeup of an individual. Non-invasively, sensors may record the standard electrocardiogram, surface recordings from higher resolution body surface potential mapping (e.g., multiple ECG electrodes) or ECG imaging, cutaneous measures of nerve activity. Reflectance on the skin to visible light or other electromagnetic waveforms can be used to measure signals that indicate heart beats, either regular or irregular. This can be detected using photoplethysmography (PPG) or other forms of detecting reflectance. Visible light in the near-infrared portion of the spectrum may be useful for this. Other types of sensing signals that may be used will be apparent to one of skill in the art.

In some embodiments, a system may include a processor and a memory storing instructions that, when executed by the processor, perform operations including detecting bodily signals associated with one or more bodily functions at one or more sensors associated with the human body, processing the bodily signals to create one or more sensed signatures, processing the signatures using the digital object to determine an effector response, delivering one or more effector responses to control a bodily task and monitoring said response.

In some embodiments, a process can identify individuals amenable to therapy for treating complex rhythm disorders, provides directional guidance in 3 dimensions to move a sensor device towards optimal locations for therapy, and enable therapy to tissue at this location. In some embodiments, a non-invasive wearable device may be used by the patient at home, without hospital visits, to determine if ablation is likely to be successful or if drug therapy should be continued. This greatly improves outpatient workflow, and reduces unsuccessful procedures by better patient selection. Another embodiment is a system providing a personalized diagnosis of rhythm disorders and a 'single shot' sensor/therapy tool. Some embodiments, which are not intended to be limiting, include cardiac applications in heart rhythm disorders, coronary artery disease and in heart failure.

In some embodiments, the device is artificial intelligence (AI) enabled non-invasive ECG device, simple enough to be applied to the chest or back by the patient at home. The single-use device will be worn for up to several days, will automatically detect the onset and then ongoing episodes of the heart rhythm disorder, and alert the user when sufficient data is recorded. Data is transmitted to the cloud for analysis, from which results will be available via electronic health records for review. Analysis can indicate if that patient will respond to ablation, if ablation is needed on the left or right side of the heart, and if they may respond to medications. The physician can then make a fully remote care plan, without the need for in-hospital evaluation or invasive testing. This is useful to streamline costs, provide access to patients in rural areas, and minimize hospital contact during public health emergencies such as the COVID pandemic. One target indication is whether to refer an AF patient directly to pulmonary vein isolation (PVI), advanced ablation, or drug therapy choice.

The guidance model 2660 analyzes the electrical signals measured by the electrode array of the catheter 155 to determine directionality guidance for the catheter 155. The guidance model 2660 inputs at least the electrical signals measured by the electrode array of the catheter 155. In other embodiments, the guidance model 2660 further inputs other data, e.g., other electrical signals measured by a non-invasive sensing device. The signals may be raw or processed by one or more data processing techniques discussed under the electrical signal processing module 2630. The features are extracted using methods such as spectral or instantaneous phase analysis in single or combinations of electrodes. Other features may include features based in the temporal domain of the signal and their first and second derivative, such as percentiles, number of local maxima or minima, features extracted from the autocorrelation, rhythm signatures, shape irregularities, etc. Other features could be extracted from the parametric or signature analysis. Features are integrated with clinical variables such as age, gender into a statistical classifier. The guidance model 2660 may be a multivariate regression or a supervised machine learning model using convolutional neural networks or support vector machines trained to a specific output label of AF termination or long-term outcome during algorithmic development. The guidance model 2660 may further output a personal digital record-based arrhythmia predictions, which can identify the specific phenotype of the patient disease such as a likely PV based AF, or AF from sites that arise away from the PVs, or VT that arises from sites common in patients with that phenotype.

The guidance direction is used to guide movement of the catheter 155 of the heart treatment device 105 to the critical region of interest, e.g., a source or target region of the arrhythmia. In some embodiments, the physician guides movement of the catheter 155 inside the patient. In such embodiments, the guidance direction can be displayed on the input/output device 125. In other embodiments the heart treatment device 105 may be motorized and automated, such that the guidance direction informs actuation of the motor to move the catheter 155 of the heart treatment device 105. The location algorithm is able to identify the position of the catheter 155 relative to the region of interest in the heart, and guide the catheter 155 to the region of interest.

Upon reaching a region of interest, the guidance model 2660 verifies the arrival of the catheter 155 at the region of interest based on the electrical signals measured by the catheter 155. The guidance model 2660 determines whether the electrical signals at the anticipated region of interest matches to known patterns for regions of interest. The guidance model 2660 can further analyze a ratio of the number of electrodes on the electrode array of the catheter 155 that are covered by the region of interest. One manner of calculating the ratio includes determining the area of the electrode array of the catheter 155 that covers the predicted region of interest. This is analogous to global positioning systems which use the current position to navigate to a desired location, without examining the entire map of the globe or remote sites. This approach enables higher resolution mapping than currently available in wide-area global or panoramic mapping systems within the heart. If the ratio is below some threshold, the guidance model 2660 determines additional guidance direction to optimize the position of the catheter 155 overlaying the region of interest. The guidance direction can include some translation (up to two degrees of freedom on the surface of the tissue) or some rotation (up to one degree of freedom, rotating about an axis perpendicular to the surface of the tissue).

In some embodiments, a non-invasive body surface mapping device uses a plurality of carefully placed electrodes on the body surface to map the heart rhythm disorder. In the prior art this typically needs anatomical information of the patient from detailed computed tomography (CT) or magnetic resonance imaging (MM) data. However, the resolution needed to identify important patient groups or rhythm types can fulfilled without the need for computed tomography (CT) scan or magnetic resonance imaging (MM) data. This increases the usability of the approach over existing methods based on medical image analysis (CT or Mill scans), since the body surface device is suitable for fully outpatient use without hospital visits for imaging. This is an advance over prior art methods such as Electrocardiographic Imaging (ECGI).

In some embodiments, navigational guidance to complement the electrode array catheter can be provided by body surface mapping without CT or Mill data, for instance to identify rhythms arising from the left side versus the right side of the heart, or separating beats originating from pulmonary vein regions of the left atrium (that project to the back) from other regions. This level of resolution can be achieved by body potential surface maps without CT or Mill data. This dispenses with the need for separate and cumbersome global 'basket' catheters.

One approach uses data from the body surface device. Another uses sophisticated directionality analysis from the electrode device inside the heart. A third combines these approaches. Directional guidance is enabled by a knowledge of the patterns of signals at the critical region, at neighboring regions, and at remote regions, and the use of signal processing (mathematical algorithms) including machine learning. This enables the system to indicate when the recording array is directly over the source. If the recording array is at a distance, then the guidance system can indicate directionality towards the source.

In some embodiments, the device can perform directional navigation from the body surface. For example, a body surface ECG may identify the location of critical regions for the heart rhythm disorder (FIG. 27). The system then calculates the direction or vector in which the electrode array catheter must be moved to reach each critical region for ablation. Directional navigation greatly advances over the prior art where the entire organ had to be mapped to identify a potentially small region of interest. One analogy is a satellite navigational system which computes directional guidance to enable a user to get from position A to B. The prior art required the user to examine and interpret a map of the city, county or country (or in the heart, a basket catheter of the global chamber) and then determine how to move from A and B. The current invention provides directionality information without requiring that the physician infer this themselves, which is subjective, or to use separate global mapping apparatus which may introduce inaccuracies and inefficiencies into the procedure.

The ablation treatment model 2670 determines parameters for an ablation procedure to be performed by the heart treatment device 105. The ablation treatment model 2670 inputs at least the electrical signals measured by the electrode array of the catheter 155. In other embodiments, the ablation treatment model 2670 further inputs other data, e.g., other electrical signals measured by a non-invasive sensing device. The signals may be raw or processed by one or more data processing techniques discussed under the electrical signal processing module 2630. The features are extracted using methods such as spectral or instantaneous phase analysis in single or combinations of electrodes. Other features may include features based in the temporal domain of the signal and their first and second derivative, such as percentiles, number of local maxima or minima, features extracted from the autocorrelation, rhythm signatures, shape irregularities, heart rhythm disorder classification, etc. Other features could be extracted from the parametric or signature analysis. Clinical variables such as age and gender may also be included as features. The ablation treatment model 2670 determines the parameters to ablate a source region that the catheter 155 of the treatment device 105 is in contact with. The parameters of the ablation procedure include select electrodes of the electrode array of the catheter 155 to actuate to deliver the ablation energy, the frequency of the ablation energy per electrode, the waveform of the ablation energy per electrode, the duration of the ablation energy per electrode, the irrigant to be delivered to the treatment site, the rate of irrigant flow, etc. The ablation procedure is provided to other components of the treatment system 100 for performing the ablation procedure.

The treatment assessment model 2680 verifies success of an ablation procedure at a particular region of interest. The treatment assessment model 2680 collects electrical signals measured by the heart treatment device 105 after the ablation procedure has been performed. The electrical signals may be analyzed to determine whether the source region is still contributing to or affecting the heart rhythm disorder. In one or more embodiments, the verification process includes movement of the catheter 155 to one or more adjacent positions to the ablated region to sense and analyze electrical signals.

The data store 2690 stores all the various data of the control system 110. The data store 2690 may be one or more computing devices that include memories or other storage media for data related to the patients, e.g., in patient profiles generated by the patient profiler 2640, such as data measured by the heart treatment device 105. Some of the data may take the form of personal digital records. The data may be routed by the control system 110. The data store 2690 may be a network-based storage server (e.g., a cloud server). The data store 2690 may be part of the computing server or may be a third-party storage system such as AMAZON AWS, AMAZON S3, DROPBOX, RACKSPACE CLOUD FILES, AZURE BLOB STORAGE, GOOGLE CLOUD STORAGE or ENGINE, etc.

Exemplary Method for Treatment of Heart Rhythm Disorder

Figure 29:
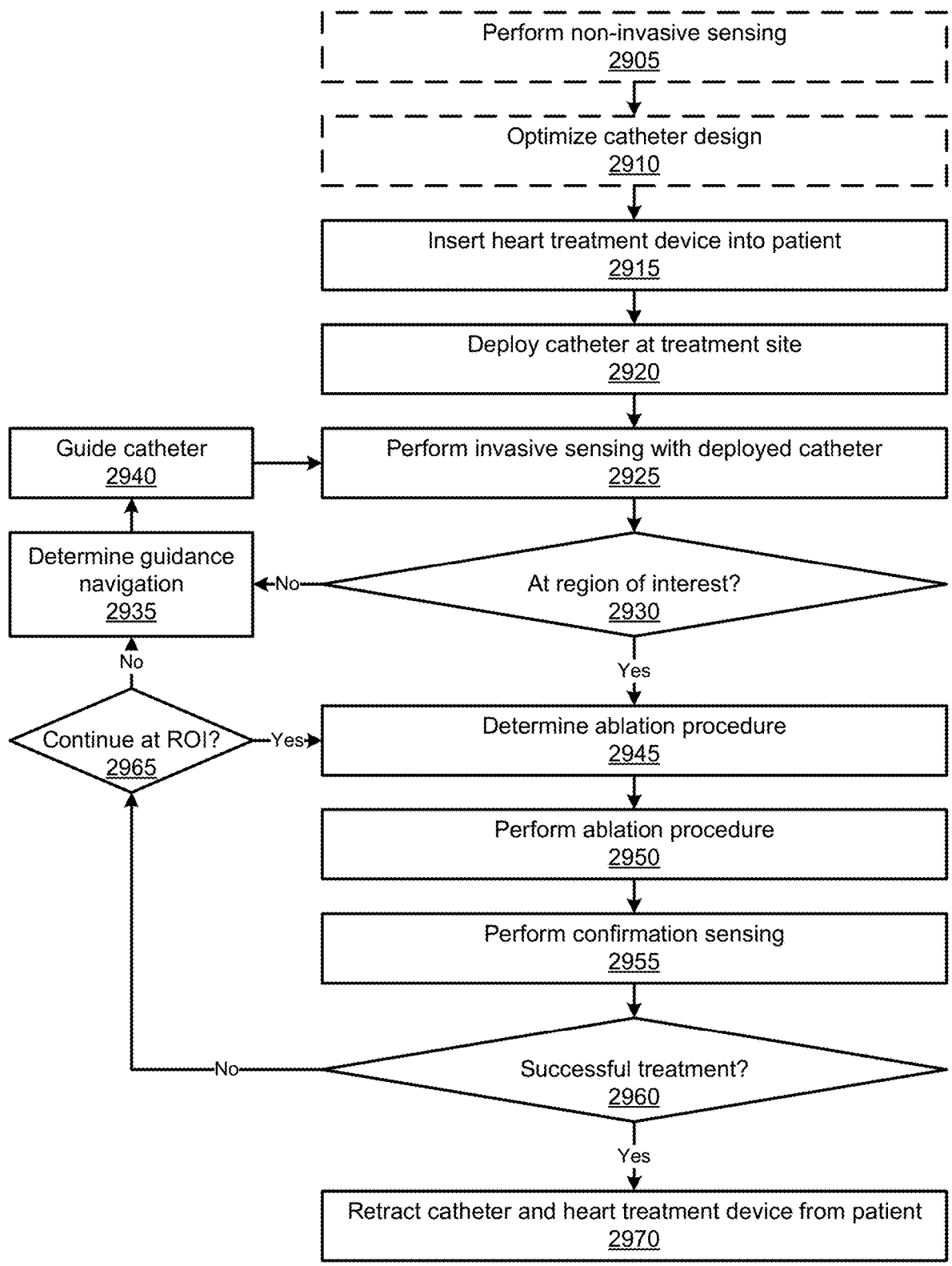
FIG. 29 illustrates a method of treating a patient with a heart rhythm disorder using the treatment system, in accordance with one or more embodiments.

FIG. 29 illustrates a method 2900 of treating a patient with a heart rhythm disorder using the treatment system 100, in accordance with one or more embodiments. For discussion purposes, each step of the method 2900 is described as being performed by the treatment system 100. However, in practice, each step of the method 2900 may be performed by a physician, another healthcare provider, or one or more components of the treatment system 100, e.g., the heart treatment device 105, the control system 110, the generator 115, the irrigation pump 120, the input/output device 125, etc. In one or more embodiments, the method 2900 can include additional, fewer, or different steps than those listed in FIG. 29.

In one or more embodiments, the treatment system 100 performs 2905 non-invasive sensing. Step 2905 is an optional step in the method 2900. The non-invasive sensing 2905 may be performed by a non-invasive sensing device, e.g., an electrode array that is worn on a patient's chest. The non-invasive sensing 2905 may provide body surface potential readings of the patient relating to a heart treatment disorder.

In one or more embodiments, the treatment system 100 optimizes 2910 a catheter design for treatment of the patient. Step 2910 is an optional step in the method 2900. The treatment system 100 (or, specifically, the catheter optimization module 2650 of the control system 110) analyzes the body surface potential readings to determine the optimal catheter design. Other factors discussed above (e.g., under the catheter optimization module 2650) may also be considered when determining the optimal catheter design (e.g., patient digital record, patient phenotypes, patient prior medical history, etc.). Catheter design may include a shape of the catheter, a size of the catheter, a configuration of the electrode array, a configuration of the irrigation pores, etc. For example, the analysis results in selecting the catheter 800 as the optimal shape for treatment of the patient, having a total dimension of the catheter in the expanded state to be 2 cm wide by 3 cm long (wherein width is measured perpendicular to the center axis and length is measured parallel to the center axis), with an electrode array that includes 5 electrodes on each of the 5 splines, with a length-wise antenna distance of 4 mm (distance between electrodes on a spline) and a width-wise antenna distance of 4 mm (distance between two splines). The optimal catheter, in some embodiments, may be selected for a set of manufactured catheters to be implemented with the heart treatment device 105. In other embodiments, the optimal catheter design is provided to a manufacturer to create.

The treatment system 100 inserts 2915 the heart treatment device 105 into the patient. In one example, the heart treatment device 105 can be inserted at a vascular access point located around the groin and steered through a femoral artery to the heart tissue. For other biological rhythm disorders persisting in other tissues, the treatment device can be inserted in various other access points. The heart treatment device 105 can be guided to the heart tissue with the aid of non-invasive imaging techniques, e.g., x-ray imaging. In some embodiments, the physician performs the insertion 2915 of the heart treatment device 105. In one or more embodiments, the insertion step 2915 includes inserting the catheter 155 and the shaft 150 of the heart treatment device 105 into an external sheath (e.g., the sheath 410) via an introducer tool. As the catheter 155 is inserted into the external sheath, the catheter 155 is transitioned into its compact state.

The treatment system 100 deploys 2920 the catheter of the heart treatment device 105 at the treatment site. Once the distal end of the heart treatment device 105 arrives at the heart tissue, the catheter 155 is deployed at the site, i.e., transitioning from a compact state to an expanded state. The expanded state of the catheter 155 permits operability of the electrode array. The deployment mechanism can be specific to each catheter design. For example, some catheters 155 rely on translation of the catheter relative to a sheath to extend the catheter 155 beyond the sheath. Unsheathing the catheter 155 may allow for one or more bends of the splines and/or the connector struts to release stored energy to separate out the splines into the expanded state. In additional examples, other catheters 155 rely on inflation of an inflatable balloon member to transition to the expanded state.

The treatment system 100 performs 2925 invasive sensing with the deployed catheter 155. The invasive sensing is accomplished by the electrode array of the catheter. Some or all of the electrodes of the electrode array can be configured to sense electrical signals of the heart tissue. The electrical signals are provided to the control system 110, e.g., via the generator 115 or over the network 130. In one or more embodiments, a non-invasive sensing device is used in conjunction with the catheter's 155 electrode array to perform the confirmation sensing 2955.

The treatment system 100 determines 2930 whether the catheter 155 is located at a region of interest. Prior to analysis, any number of signal pre-processing techniques may be applied (e.g., by the electrical signal processing module 2630). In one or more embodiments, the control system 110 (or more specifically the guidance model 2660 of the control system 110) analyzes the electrical signals sensed at step 2925 to determine whether the catheter 155 is located at the region of interest. A region of interest may be a source region, a driver, or any other region contributing to the heart rhythm disorder requiring ablation treatment. Further detail regarding the analysis at step 2930 is discussed under the guidance model 2660.

In response to determining that the catheter 155 is not at a region of interest, the treatment system 100 determines 2935 guidance navigation to direct the catheter to a region of interest. One or more machine-learned models may be applied to the electrical signals measured by the electrode array of the catheter to determine a direction of a region of interest from the current location of the catheter 155.

The treatment system 100 guides 2940 the catheter 155 according to the determined guidance direction. Guiding the catheter 155 may be accomplished autonomously by the treatment system 100. In other embodiments, the treatment system 100 displays the guidance direction (e.g., via the input/output device 125) to the physician. The physician may manually guide the catheter and/or provide control inputs (via the input/output device 125) to control movement of the catheter according to the guidance direction.

After guiding the catheter 155 to a new location, the treatment system 100 may reperform 2925 invasive sensing with the electrode array of the deployed catheter 155. The treatment system 100 may repeat in a loop steps 2925, 2930, 2935, and 2940 to successfully guide the catheter 155 to a region of interest.

In response to determining that the catheter 155 is at a region of interest, the treatment system 100 determines 2945 an ablation procedure to perform at the region of interest. The treatment system 100 (or more specifically the ablation treatment model 2670 of the control system 110) analyzes the electrical signals at the region of interest to determine the appropriate ablation procedure. Parameters of the ablation procedure may include which electrodes of the electrode array the deliver ablation energy (i.e., an ablation pattern), what frequency of the ablation energy per electrode configured for ablation, what waveform of the ablation energy per electrode configured for ablation, what duration to deliver the ablation energy per electrode configured for ablation, which irrigation pores to provide irrigant, flow rate of irrigant for irrigation pores configured to deliver irrigant, etc.

The treatment system 100 performs 2950 the ablation procedure determined at step 2940. The generator 115 may deliver the electrical energy to the electrode array of the catheter 155. The interposer 140 may selectively switch the determined electrodes to be used for ablation to an ablation configuration, and may switch the remaining electrodes into a ground configuration. The energy source 135 provides the ablation energy according to the parameters determined at step 2940 to each electrode configured for ablation. The irrigation pump 120 pumps irrigant to the irrigation pores of the catheter 155, which vents the irrigant to the tissue during delivery of the ablation energy.

The treatment system 100 performs 2955 confirmation sensing at the region of interest. Some or all electrodes of the electrode array perform the confirmation sensing 2955. The interposer 140 may switch some or all of the electrodes into the sensing configuration. The electrical signals sensed at the region of interest are provided to the control system 110 to analyze. In some embodiments, the catheter 155 and the electrode array are moved to regions surrounding the ablated region of interest to measure confirmation sensing signals. In one or more embodiments, a non-invasive sensing device is used to perform the confirmation sensing 2955.

The treatment system 100 determines 2960 whether the treatment was successful based on the electrical signals measured at step 2955. The control system 110 (or more specifically the treatment assessment model 2680) can analyze the electrical signals to determine whether the heart rhythm disorder persists or if the heart rhythm disorder has been successfully treated.

In response to determining that the treatment was not successful, the treatment system 100 determines 2965 whether to continue treatment at the current region of interest (ROI). For example, the treatment system 100 (or more specifically the treatment assessment model 2680 of the control system 110) determines whether the current region of interest is still contributing to the heart rhythm disorder.

In response to determining to continue at the current region of interest, the treatment system 100 determines 2945 another ablation procedure for the current region of interest. The additional ablation procedure may have similar parameters to the prior ablation procedure or may have different parameters. For example, a second ablation procedure may have a different ablation pattern, a different duration for delivery of the ablation energy, one or more pauses between periods of delivery ablation energy, or a different waveform for the ablation energy, when compared to a first ablation procedure. The treatment system 100 may repeat steps 2945, 2950, 2955, and 2960 in a loop, e.g., until the current region of interest no longer contributes to the heart rhythm disorder. Other stop conditions may be implemented, e.g., a hard stop of 3 ablation procedures.

In response to determining to not continue at the current region of interest, the treatment system 100 determines 2935 guidance navigation for steering the catheter to another region of interest. The treatment system 100 may repeat steps 2935, 2940, 2925, and 2930 to arrive at the next region of interest for ablation treatment.

In response to determining that the treatment was successful at step 2960, the treatment system 100 retracts 2970 the catheter 155 and the heart treatment device 105 from the patient. This can include both retracting the catheter 155 into a compact state and removing the heart treatment device 105 from the patient. Depending on the deployment mechanism of the catheter 155, retraction can include sheathing the catheter 155 and/or releasing fluid in the balloon catheter 155, etc. Once the heart treatment device 105 has been removed, the method 2900 for treatment of the heart rhythm disorder is completed.

Example Computing System

Figure 30:
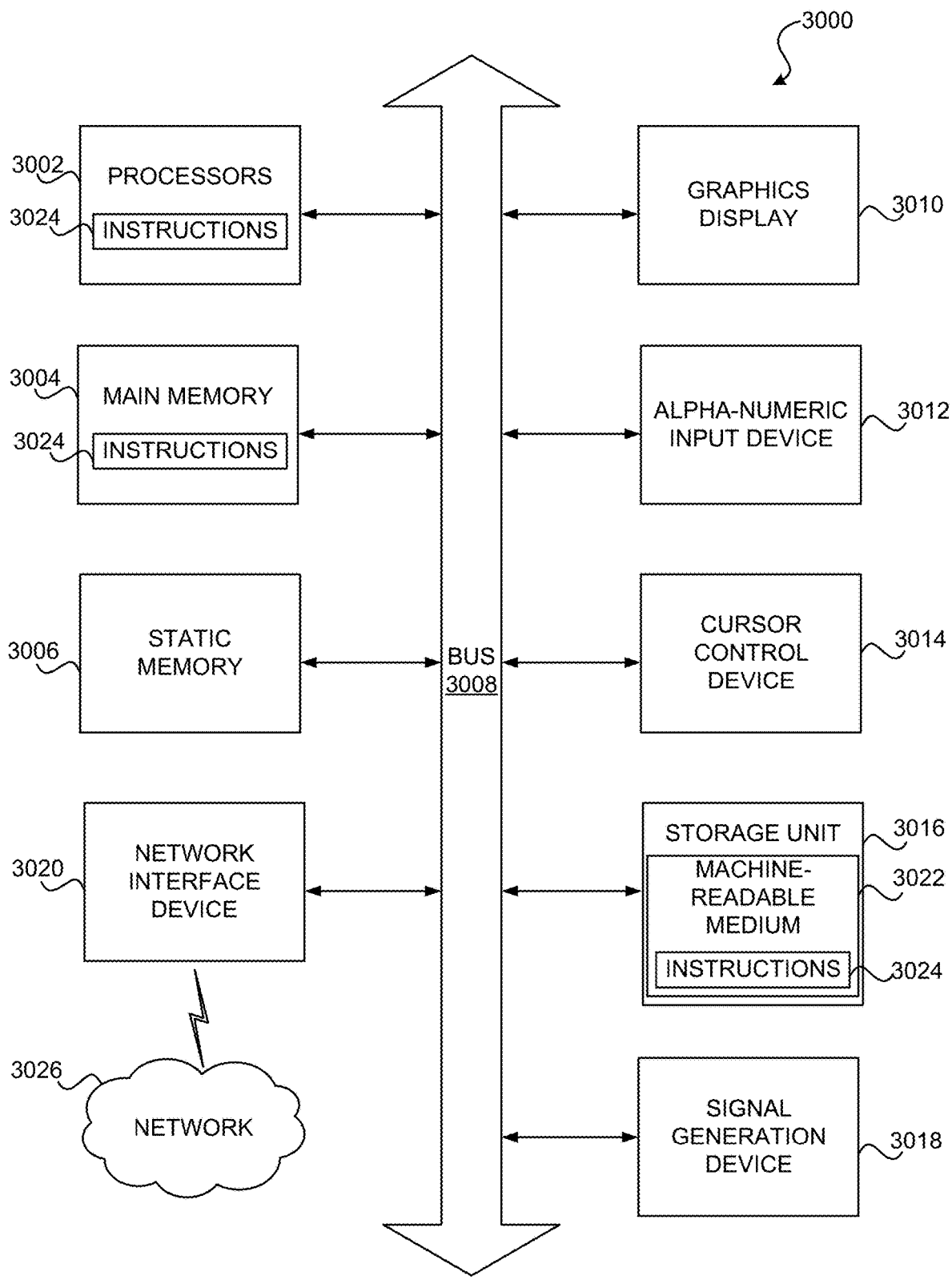
FIG. 30 illustrates a block diagram of a general computing system, according to one or more embodiments.

FIG. 30 illustrates a block diagram of a general computing system, according to one or more embodiments. A computer described herein may include a single computing machine shown in FIG. 30, a virtual machine, a distributed computing system that includes multiples nodes of computing machines shown in FIG. 30, or any other suitable arrangement of computing devices.

By way of example, FIG. 30 shows a diagrammatic representation of a computing machine in the example form of a computer system 3000 within which instructions 3024 (e.g., software, source code, program code, expanded code, object code, assembly code, or machine code), which may be stored in a computer-readable medium for causing the machine to perform any one or more of the processes discussed herein may be executed. In some embodiments, the computing machine operates as a standalone device or may be connected (e.g., networked) to other machines. In a networked deployment, the machine may operate in the capacity of a server machine or a client machine in a server-client network environment, or as a peer machine in a peer-to-peer (or distributed) network environment.

The structure of a computing machine described in FIG. 30 may correspond to any software, hardware, or combined components shown in FIG. 1A, including but not limited to, the control system 110, and various engines, interfaces, terminals, and machines in this disclosure. While FIG. 30 shows various hardware and software elements, each of the components described in FIG. 1 may include additional or fewer elements.

By way of example, a computing machine may be a personal computer (PC), a tablet PC, a set-top box (STB), a personal digital assistant (PDA), a cellular telephone, a smartphone, a web appliance, a network router, an internet of things (IoT) device, a switch or bridge, or any machine capable of executing instructions 3024 that specify actions to be taken by that machine. Further, while only a single machine is illustrated, the term "machine" and "computer" may also be taken to include any collection of machines that individually or jointly execute instructions 3024 to perform any one or more of the methodologies discussed herein.

The example computer system 3000 includes one or more processors 3002 such as a CPU (central processing unit), a GPU (graphics processing unit), a TPU (tensor processing unit), a DSP (digital signal processor), a system on a chip (SOC), a controller, a state equipment, an application-specific integrated circuit (ASIC), a field-programmable gate array (FPGA), or any combination of these. Parts of the computing system 3000 may also include a memory 3004 that store computer code including instructions 3024 that may cause the processors 3002 to perform certain actions when the instructions are executed, directly or indirectly by the processors 3002. Instructions can be any directions, commands, or orders that may be stored in different forms, such as equipment-readable instructions, programming instructions including source code, and other communication signals and orders. Instructions may be used in a general sense and are not limited to machine-readable codes. One or more steps in various processes described may be performed by passing through instructions to one or more multiply-accumulate (MAC) units of the processors.

One and more methods described herein improve the operation speed of the processors 3002 and reduces the space required for the memory 3004. For example, the signal processing techniques and machine learning methods described herein reduce the complexity of the computation of the processors 3002 by applying one or more novel techniques that simplify the steps in training, reaching convergence, and generating results of the processors 3002. The algorithms described herein also reduces the size of the models and datasets to reduce the storage space requirement for memory 3004.

The performance of certain of the operations may be distributed among the more than processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations. Even though in the specification or the claims may refer some processes to be performed by a processor, this should be construed to include a joint operation of multiple distributed processors.

The computer system 3000 may include a main memory 3004, and a static memory 3006, which are configured to communicate with each other via a bus 3008. The computer system 3000 may further include a graphics display unit 3010 (e.g., a plasma display panel (personal digital record), a liquid crystal display (LCD), a projector, or a cathode ray tube (CRT)). The graphics display unit 3010, controlled by the processors 3002, displays a graphical user interface (GUI) to display one or more results and data generated by the processes described herein. The computer system 3000 may also include alphanumeric input device 3012 (e.g., a keyboard), a cursor control device 3014 (e.g., a mouse, a trackball, a joystick, a motion sensor, or other pointing instrument), a storage unit 3016 (a hard drive, a solid state drive, a hybrid drive, a memory disk, etc.), a signal generation device 3018 (e.g., a speaker), and a network interface device 3020, which also are configured to communicate via the bus 3008.

The storage unit 3016 includes a computer-readable medium 3022 on which is stored instructions 3024 embodying any one or more of the methodologies or functions described herein. The instructions 3024 may also reside, completely or at least partially, within the main memory 3004 or within the processor 3002 (e.g., within a processor's cache memory) during execution thereof by the computer system 3000, the main memory 3004 and the processor 3002 also constituting computer-readable media. The instructions 3024 may be transmitted or received over a network 3026 via the network interface device 3020.

While computer-readable medium 3022 is shown in an example embodiment to be a single medium, the term "computer-readable medium" should be taken to include a single medium or multiple media (e.g., a centralized or distributed database, or associated caches and servers) able to store instructions (e.g., instructions 3024). The computer-readable medium may include any medium that is capable of storing instructions (e.g., instructions 3024) for execution by the processors (e.g., processors 3002) and that cause the processors to perform any one or more of the methodologies disclosed herein. The computer-readable medium may include, but not be limited to, data repositories in the form of solid-state memories, optical media, and magnetic media. The computer-readable medium does not include a transitory medium such as a propagating signal or a carrier wave.

Additional Description

Aspect 1. A treatment system for sensing and ablating tissue to treat a biological rhythm disorder, comprising: a catheter for insertion into a patient, the catheter comprising: a plurality of ablation electrodes arranged in a first array of at least 2 dimensions and configured to deliver ablation energy to modify tissue contributing to the biological rhythm disorder, and a plurality of sensing electrodes arranged in a second array of at least 2 dimensions and configured to sense electrical signals from the tissue, wherein said sensing electrodes are configured to monitor signals during delivery of ablation energy; and an interposer configured to regulate delivery of ablation energy to each ablation electrode based on the electrical signals from the tissue.

Aspect 2, the treatment system of aspect 1, wherein each ablation electrode is also a sensing electrode.

Aspect 3. The treatment system of aspect 1, wherein the interposer is further configured to convert the electrical signals sensed by the sensor to a temperature signal, wherein the interposer regulates delivery of the ablation energy based on the temperature signal.

Aspect 4. The treatment system of aspect 1, wherein the interposer is further configured to analyze the electrical signals comprising an impedance, wherein the interposer regulates delivery of the ablation energy based on the impedance.

Aspect 5. The treatment system of aspect 1, wherein the interposer is further configured to analyze the electrical signals comprising an amplitude, wherein the interposer regulates delivery of the ablation energy based on attenuation of the amplitude.

Aspect 6. The treatment system of aspect 1, wherein the desired therapy window provides energy sufficient to modify biological tissue, yet does not reach a level to cause charring of tissue, clotting of blood, perforation of the biological organ or other adverse effects.

Aspect 7. The treatment system of aspect 1, wherein the electrical signals comprise a combination of impedance, amplitude, frequency, current, and voltage.

Aspect 8. The treatment system of aspect 1, wherein the interposer receives ablation energy from an ablation energy generator.

Aspect 9. The treatment system of aspect 7, wherein the ablation energy comprises radiofrequency energy.

Aspect 10. The treatment system of aspect 1, wherein the catheter further comprises a plurality of irrigation pores configured to vent irrigant to the tissue Aspect 11. The treatment system of aspect 1, wherein the catheter vents an amount of irrigant from the irrigation pores based on the sensed electrical signals from the tissue.

Aspect 12. The treatment system of aspect 1, wherein the ablation electrodes are configured in the first array of size selected from the range of 2×2 to 12×12.

Aspect 13. The treatment system of aspect 1, wherein the sensing electrodes are configured in the second array of size selected from the range of 2×2 to 12×12.

Aspect 14. The treatment system of aspect 1, wherein the catheter is collapsible into a sheath and expandable for treatment.

Aspect 15. The treatment system of aspect 1, wherein the catheter is configured to deliver the ablation energy through a subset of the ablation electrodes.

Aspect 16. A treatment device configured to diagnose and to treat a biological rhythm disorder, the treatment device comprising: a catheter that is configured to transition between a compact state and an expanded state, wherein the compact state is configured for insertion of the catheter into a patient, and wherein the expanded state is configured for treatment of the biological rhythm disorder, the catheter comprising: a housing that is configured to expand and to collapse, and an electrode array disposed on the housing, wherein 2 or more electrodes of the electrode array are configured to switch between a sensing configuration for sensing an electrical signal and an ablation configuration for delivering an ablation energy signal, wherein the electrode array is able to deliver ablation energy in a plurality of ablation patterns based on switching different subsets of electrodes in the electrode array to the ablation configuration.

Aspect 17. The heart treatment device of aspect 16, wherein the catheter further comprises a plurality of irrigation pores disposed on the catheter and configured to vent irrigant to tissue during an ablation procedure.

Aspect 18. The heart treatment device of aspect 16, wherein dimensions of the electrode array may be optimized according to electrical signals of a patient that are measured by a non-invasive sensing device.

Aspect 19. The heart treatment device of aspect 18, wherein the dimensions of the electrode array include any combination of the following: a total number of electrodes; a number of electrodes disposed on each spline of the plurality of splines; a size of each electrode; a width-wise antenna distance between electrodes on adjacent splines; a length-wise antenna distance between electrodes on one spline; and a unipolar configuration or a bipolar configuration.

Aspect 20. The heart treatment device of aspect 16, wherein the housing further comprises: an inflatable member configured to expand based on movement of a fluid into the inflatable member and to collapse based on movement of the fluid out of the inflatable member; and a plurality of splines that is flexible and coupled radially to the inflatable member, wherein the electrode array is disposed on the plurality of splines.

Aspect 21. A method of directing a treatment device towards a critical region for a biological rhythm disorder for therapy, comprising: detecting electrical signals of biological tissue at a current location with an electrode array disposed on a catheter of the treatment device; determining whether the catheter is at a region of interest by analyzing the electrical signals captured by the electrode array; in response to determining that the catheter is not at a region of interest: determining a pattern of the biological rhythm disorder at the current location based on the electrical signals; determining a guidance direction for movement of the catheter towards a region of interest based on the pattern of the biological rhythm disorder; guiding the catheter to a subsequent location along the guidance direction; and performing ablation therapy at a region of interest.

Aspect 22. The method of aspect 21, further comprising: sensing body-surface electrical signals relating to the biological tissue using a non-invasive sensing device; and optimizing a design of the catheter based on the sensed body-surface electrical signals.

Aspect 23. The method of aspect 22, wherein the design of the catheter includes any combination of: a shape of the catheter; a number of splines on the catheter; a size of the catheter; a total number of electrodes in the electrode array; a spatial configuration of the electrodes in the electrode array; a number of electrodes on each spline; a size of each electrode; a width-wise antenna distance between electrodes on adjacent splines; and a length-wise antenna distance between electrodes on one spline.

Aspect 24. The method of aspect 21, wherein guiding the catheter to the subsequent location comprises actuating a motor to move the catheter to the subsequent location.

Aspect 25. The method of aspect 21, wherein guiding the catheter to the subsequent location comprises displaying the guidance direction on an external display device, wherein a physician steers the catheter based on the displayed guidance direction.

Aspect 26. A heart treatment device comprising: a catheter comprising: a plurality of splines coupled to a shaft at a distal end of the shaft, a plurality of connector struts connected to the plurality of splines, wherein the plurality of connector struts is composed of an elastic material, wherein each connector comprises one or more bends capable of storing potential energy, and an electrode array disposed on one or more spline of the plurality of splines, wherein 2 or more electrodes of the electrode array is configured to switch between a sensing configuration for sensing an electrical signal and an ablation configuration for delivering an ablation energy signal; a plurality of wires connected to the electrode array of the catheter disposed within the shaft, the plurality of wires configured to transfer electrical signals sensed by the electrode array to a controller and to transfer ablation energy signals from the controller to the electrode array; wherein extension of the shaft in a distal direction causes the catheter to extend beyond a sheath, wherein the extension releases stored potential energy in the plurality of connectors causing the plurality of splines to separate from a compact state to an expanded state; and wherein retraction of the shaft in a proximal direction into the sheath causes the plurality of splines to collapse from the expanded state to the compact state storing potential energy in the plurality of connectors.

Aspect 27. The heart treatment device of aspect 26, wherein the catheter further comprises a plurality of irrigation pores disposed on the plurality of splines and configured to vent irrigant to tissue during an ablation procedure.

Aspect 28. The heart treatment device of aspect 27, wherein the irrigation pores are interlaced with the electrode array.

Aspect 29. The heart treatment device of aspect 27, wherein each spline of the plurality of splines includes five electrodes interlaced with four irrigation pores.

Aspect 30 The heart treatment device of aspect 29, wherein the plurality of splines includes five splines, totaling twenty-five electrodes and twenty irrigation pores.

Aspect 31. The heart treatment device of aspect 27, wherein each irrigation pore is individually addressable to vent irrigant.

Aspect 32. The heart treatment device of aspect 27, wherein a ratio of the irrigation pores to the electrodes is within a range of 2:1 to 1:9.

Aspect 33. The heart treatment device of aspect 26, wherein the plurality of splines includes five splines including: a center spline aligned with a center axis of the shaft; two inner splines disposed on either side of the center spline at a first radial distance from the center axis; and two outer splines disposed on either side of the center spline at a second radial distance from the center axis that is greater than the first radial distance.

Aspect 34. The heart treatment device of aspect 33, wherein a first connector connects distal ends of the inner splines.

Aspect 35. The heart treatment device of aspect 34, wherein a second connector connects distal ends of the outer splines.

Aspect 36. The heart treatment device of aspect 35, wherein the first connector and the second connector have a rounded V-shape.

Aspect 37. The heart treatment device of aspect 36, wherein a third connector connects the first connector and the second connector along the center axis.

Aspect 38. The heart treatment device of aspect 37, wherein a fourth connector connects the first connector and the center spline.

Aspect 39. The heart treatment device of aspect 38, wherein the third connector and the fourth connector have a sinusoidal shape.

Aspect 40. The heart treatment device of aspect 39, wherein each of the third connector and the fourth connector has a peak and a trough as two bends.

Aspect 41. The heart treatment device of aspect 35, wherein a first set of two connectors connect the outer splines to the inner splines, and a second set of two connectors connect the inner splines to the center spline.

Aspect 42. The heart treatment device of aspect 41, wherein the first set of two connectors is longer than the second set of two connectors measured along the center axis.

Aspect 43. The heart treatment device of aspect 41, wherein the second set of two connectors is longer than the first set of two connectors measured along the center axis.

Aspect 44. The heart treatment device of aspect 26, wherein the plurality of splines includes four splines including: two inner splines disposed on either side of the center axis at a first radial distance from the center axis; and two outer splines disposed on either side of the center axis at a second radial distance from the center axis that is greater than the first radial distance.

Aspect 45. The heart treatment device of aspect 44, wherein a first connector connects distal ends of the inner splines.

Aspect 46. The heart treatment device of aspect 45, wherein a second connector connects distal ends of the outer splines.

Aspect 47. The heart treatment device of aspect 46, wherein a third connector connects the first connector and the second connector along the center axis.

Aspect 48. The heart treatment device of aspect 26, wherein at least a first spline of the plurality of splines includes a bend that is capable of storing potential energy Aspect 49. The heart treatment device of aspect 26, wherein the bends of the connectors store potential energy when deformed and in the compact state.

Aspect 50. The heart treatment device of aspect 26, wherein the plurality of splines is composed of nitinol with an insulative coating.

Aspect 51. The heart treatment device of aspect 26, wherein the catheter further comprises the shaft, and wherein the shaft is steerable using one or more steering wires connected to a steering ring disposed at a proximal end of the shaft.

Aspect 52. The heart treatment device of aspect 51, wherein the shaft is composed of a flexible material.

Aspect 53. The heart treatment device of aspect 52, wherein the shaft comprises two steering wires coupled to the distal end of the shaft on either side of the center axis, wherein tension in one of the steering wires induces a curvature in the shaft towards the steering wire under tension.

Aspect 54. The heart treatment device of aspect 26, wherein each electrode of the electrode array is composed of metal and wrapped around a spline of the plurality of splines.

Aspect 55. The heart treatment device of aspect 26, wherein each electrode of the electrode array is individually addressable to switch between the sensing configuration and the ablation configuration.

Aspect 56. The heart treatment device of aspect 26, wherein dimensions of the electrode array may be optimized according to electrical signals of a patient that are measured by a non-invasive sensing device.

Aspect 57. The heart treatment device of aspect 56, wherein the dimensions of the electrode array include any combination of the following: a total number of electrodes; a spatial configuration of the electrodes in the electrode array; a number of electrodes disposed on each spline of the plurality of splines; a size of each electrode; a width-wise antenna distance between electrodes on adjacent splines; a length-wise antenna distance between electrodes on one spline; and a unipolar configuration or a bipolar configuration.

Aspect 58. A method for treating a heart rhythm disorder with ablation therapy, the method comprising: inserting a catheter of a heart treatment device into a patient, wherein the catheter is in a compact state during insertion; deploying the catheter by extending the catheter beyond a sheath, wherein extension of the catheter beyond the sheath releases stored potential energy in a plurality of connectors of the catheter causing a plurality of splines of the catheter to separate from a compact state to an expanded state; steering the catheter to a treatment site for heart tissue contributing to the heart rhythm disorder; detecting electrical signals of the heart tissue at the treatment site with an electrode array of the catheter, wherein the electrode array is disposed on the plurality of splines of the catheter and in a sensing configuration; determining whether the catheter is at a region of interest by analyzing the electrical signals captured by the electrode array of the heart tissue; in response to determining that the catheter is at a region of interest, determining an ablation procedure based on the electrical signals; switching the electrode array to an ablation configuration; delivering ablation energy with the electrode array to the heart tissue at the region of interest according to the ablation procedure; retracting the catheter into the sheath, wherein retraction causes the plurality of splines to collapse from the expanded state to the compact state storing potential energy in the plurality of connectors; and removing the catheter from the patient.

Aspect 59. The method of aspect 58, further comprising: sensing body-surface electrical signals relating to the heart tissue using a non-invasive sensing device; and optimizing a design of the catheter based on the sensed body-surface electrical signals.

Aspect 60. The method of aspect 59, wherein the design of the catheter includes any combination of: a shape of the catheter; a number of splines on the catheter; a size of the catheter; a total number of electrodes in the electrode array; a spatial configuration of the electrodes in the electrode array; a number of electrodes on each spline; a size of each electrode; a width-wise antenna distance between electrodes on adjacent splines; and a length-wise antenna distance between electrodes on one spline.

Aspect 61. The method of aspect 58, further comprising: in response to determining that the catheter is not at a region of interest, iteratively: determining a guidance direction for movement of the catheter towards a region of interest based on the electrical signals sensed by the electrode array; moving the catheter to a second location along the guidance direction; and detecting additional electrical signals at the second location to determine whether the catheter is at a region of interest for performing ablation therapy.

Aspect 62. The method of aspect 58, wherein determining the ablation procedure based on the electrical signals comprises: identifying an electrical signature of the heart rhythm disorder based on the electrical signals; and determining an ablation pattern based on the electrical signature, wherein the ablation pattern identifies a subset of electrodes in the electrode array for delivery of the ablation energy.

Aspect 63. The method of aspect 62, wherein switching the electrode array to the ablation configuration comprises: switching the subset of electrodes to the ablation configuration.

Aspect 64. The method of aspect 63, wherein switching the electrode array to the ablation configuration further comprises: switching one or more remaining electrodes not included in the subset of electrodes to a ground configuration.

Aspect 65. The method of aspect 62, wherein the ablation procedure further details any combination of: a frequency for each electrode in the subset of electrodes identified for delivery of the ablation energy; a waveform for each electrode in the subset of electrodes identified for delivery of the ablation energy; and a duration of ablation energy for each electrode in the subset of electrodes identified for delivery of the ablation energy.

Aspect 66. The method of aspect 62, further comprising: during delivery of the ablation energy by the electrode array, venting irrigant from one or more irrigation pores disposed on the splines of the catheter.

Aspect 67. The method of aspect 62, further comprising: after delivery of the ablation energy, switching the electrode array to the sensing configuration; detecting additional electrical signals in the heart tissue with the electrode array; and confirming whether the heart rhythm disorder was successfully treated based on the additional electrical signals, wherein retraction of the catheter and removal of the shaft from the patient is in response to determining that the heart rhythm disorder was successfully treated.

Aspect 68. The method of aspect 67, further comprising: in response to determining that the heart rhythm disorder was not successfully treated, determining whether to continue at the region of interest based on the additional electrical signals; in response to determining to continue at the region of interest: determining a second ablation procedure based on the additional electrical signals, switching the electrode array to the ablation configuration, and delivering ablation energy with the electrode array to the heart tissue at the region of interest according to the second ablation procedure.

Aspect 69. The method of aspect 68, further comprising: in response to determining to not continue at the region of interest iteratively: determining a guidance direction for movement of the catheter towards a second region of interest based on the additional electrical signals sensed by the electrode array; moving the catheter to a second location along the guidance direction; and detecting subsequent electrical signals at the second location to determine whether the catheter is at the second region of interest for performing ablation therapy.

Aspect 70. A non-transitory computer-readable medium storing instructions that, when executed by a processor, cause the processor to perform the method of any of the aspects.

Aspect 71. A computer system comprising: a processor; and a non-transitory computer-readable medium storing instructions that, when executed by a processor, cause the processor to perform the method of any of the aspects.

Aspect 72. An interposer for modulating ablation energy, the interposer comprising: a power controller electrically connected to an ablation energy generator and to a heart treatment device, wherein the power controller is configured to deliver a controlled amount of the ablation energy to the heart treatment device; a signal conditioner electrically connected to the heart treatment device, wherein the signal conditioner comprises a filtering circuitry that is configured to attenuate any ablation energy and to pass through any low frequency signal sensed by the heart treatment device; a signal processor electrically connected to the signal conditioner, wherein the signal processor is configured to convert the low frequency signal passed from the signal conditioner to a temperature signal; and a microcontroller unit electrically connected to the signal processor and the signal conditioner, wherein the microcontroller unit is configured to deliver a pulse width modulation (PWM) signal to the power controller to control the amount of the ablation energy delivered to the heart treatment device based on the temperature signal.

Aspect 73. The interposer of aspect 72, wherein the power controller comprises shunting circuitry that is configured to divert an amount of the ablation energy from being delivered to the heart treatment device.

Aspect 74. The interposer of aspect 73, wherein the shunting circuitry comprises a resistor that is configured to dissipate the diverted ablation energy.

Aspect 75. The interposer of aspect 74, wherein the power controller is configured to instruct the amount of the ablation energy that is diverted to the shunting circuitry.

Aspect 76. The interposer of aspect 72, wherein the signal conditioner is configured to filter an alternating current (AC) component of the incoming signal from the heart treatment device, leaving a direct current (DC) component to be processed by the signal processor.

Aspect 77. The interposer of aspect 72, wherein the signal conditioner comprises: a low pass filter that filters out high frequency signals and passes through any low frequency signal; and an operational amplifier that buffers the low frequency signal passed through by the low pass filter.

Aspect 78. The interposer of aspect 72, wherein the signal conditioner is configured to receive a voltage input from an electrode wiring of the heart treatment device, the electrode wiring comprising two dissimilar electrical conductors forming an electrical junction that generates a temperature-dependent voltage.

Aspect 79. The interposer of aspect 72, wherein the PWM signal is configured to instruct lessening the ablation energy delivered to a subset of electrodes of an electrode array of the heart treatment device.

Aspect 80. A system and device for delivery and control of ablation energy comprising: a heart treatment device comprising an electrode array, wherein at least a first electrode of the electrode array is configured to deliver ablation energy, and at least a second electrode of the electrode array is configured to sense electrical signals from tissue; and the interposer of aspect 72.

Aspect 81. The system of aspect 80, further comprising an ablation energy generator configured to generate the ablation energy.

Aspect 82. The system of aspect 80, wherein the ablation energy comprises radiofrequency energy.

Additional Considerations

The foregoing description of the embodiments has been presented for the purpose of illustration; it is not intended to be exhaustive or to limit the patent rights to the precise forms disclosed. Persons skilled in the relevant art can appreciate that many modifications and variations are possible in light of the above disclosure.

Any feature mentioned in one claim category, e.g. method, can be claimed in another claim category, e.g. computer program product, system, storage medium, as well. The dependencies or references back in the attached claims are chosen for formal reasons only. However, any subject matter resulting from a deliberate reference back to any previous claims (in particular multiple dependencies) can be claimed as well, so that any combination of claims and the features thereof is disclosed and can be claimed regardless of the dependencies chosen in the attached claims. The subject-matter may include not only the combinations of features as set out in the disclosed embodiments but also any other combination of features from different embodiments. Various features mentioned in the different embodiments can be combined with explicit mentioning of such combination or arrangement in an example embodiment or without any explicit mentioning. Furthermore, any of the embodiments and features described or depicted herein may be claimed in a separate claim and/or in any combination with any embodiment or feature described or depicted herein or with any of the features.

Some portions of this description describe the embodiments in terms of algorithms and symbolic representations of operations on information. These operations and algorithmic descriptions, while described functionally, computationally, or logically, are understood to be implemented by computer programs or equivalent electrical circuits, microcode, or the like. Furthermore, it has also proven convenient at times, to refer to these arrangements of operations as engines, without loss of generality. The described operations and their associated engines may be embodied in software, firmware, hardware, or any combinations thereof.

Any of the steps, operations, or processes described herein may be performed or implemented with one or more hardware or software engines, alone or in combination with other devices. In some embodiments, a software engine is implemented with a computer program product comprising a computer-readable medium containing computer program code, which can be executed by a computer processor for performing any or all of the steps, operations, or processes described. The term "steps" does not mandate or imply a particular order. For example, while this disclosure may describe a process that includes multiple steps sequentially with arrows present in a flowchart, the steps in the process do not need to be performed by the specific order claimed or described in the disclosure. Some steps may be performed before others even though the other steps are claimed or described first in this disclosure. Likewise, any use of (i), (ii), (iii), etc., or (a), (b), (c), etc. in the specification or in the claims, unless specified, is used to better enumerate items or steps and also does not mandate a particular order.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein. In addition, the term "each" used in the specification and claims does not imply that every or all elements in a group need to fit the description associated with the term "each." For example, "each member is associated with element A" does not imply that all members are associated with an element A. Instead, the term "each" only implies that a member (of some of the members), in a singular form, is associated with an element A. In claims, the use of a singular form of a noun may imply at least one element even though a plural form is not used.

Finally, the language used in the specification has been principally selected for readability and instructional purposes, and it may not have been selected to delineate or circumscribe the patent rights. It is therefore intended that the scope of the patent rights be limited not by this detailed description, but rather by any claims that issue on an application based hereon. Accordingly, the disclosure of the embodiments is intended to be illustrative, but not limiting, of the scope of the patent rights.

What is claimed is:

1. A treatment system for sensing and ablating tissue to treat a biological rhythm disorder, comprising:
  a catheter for insertion into a patient, the catheter comprising:
    a set of splines connected to form a surface that has a top side and a bottom side;
    a plurality of ablation electrodes carried by the set of splines and arranged in a first array, the plurality of ablation electrodes configured to deliver ablation energy to modify tissue contributing to the biological rhythm disorder, and
    a plurality of sensing electrodes carried by the set of splines and arranged in a second array, the plurality of sensing electrodes configured to sense electrical signals from the tissue corresponding to electrical activity of the tissue, at least one of the sensing electrodes having a conductive material on both the top side and the bottom side of the surface formed by the set of splines so that the at least one of the sensing electrodes is capable of sensing electrical signals from the top side or the bottom side, wherein the plurality of sensing electrodes in the second array is arranged in a central region of electrodes and a peripheral region of electrodes enclosing the central region, wherein electrodes in the peripheral region of electrodes are spaced sparser than electrodes in the central region, wherein the plurality of sensing electrodes is configured to monitor the electrical signals during delivery of the ablation energy; and a control system configured to:
  determine a personalized shape of a critical region in the tissue that contributes to the biological rhythm disorder based on the electrical signals sensed by the plurality of sensing electrodes,
  determine an ablation pattern based on the personalized shape of the critical region, wherein the ablation pattern indicates a subset of the plurality of ablation electrodes to activate and an amount of ablation energy with which to activate each ablation electrode in the subset, and
  instruct activation of at least the subset of ablation electrodes to achieve the ablation pattern.

2. The treatment system of claim 1, wherein each ablation electrode is also a sensing electrode.

3. The treatment system of claim 1, wherein the control system is further configured to convert the electrical signals sensed by the plurality of sensing electrodes to a temperature signal, wherein the control system regulates delivery of the ablation energy based on the temperature signal.

4. The treatment system of claim 1, wherein the control system is further configured to analyze the electrical signals comprising an impedance, wherein the control system regulates delivery of the ablation energy based on the impedance.

5. The treatment system of claim 1, wherein the control system is further configured to analyze the electrical signals comprising an amplitude, wherein the control system regulates delivery of the ablation energy based on attenuation of the amplitude.

6. The treatment system of claim 1, wherein the ablation energy delivered by the plurality of ablation electrodes provides energy sufficient to modify a region of the tissue, yet does not reach a level to cause charring of the tissue, clotting of blood, or perforation of the tissue.

7. The treatment system of claim 1, wherein the electrical signals comprise a combination of one or more of impedance, amplitude, frequency, current, or voltage.

8. The treatment system of claim 1, wherein the catheter is configured to receive the ablation energy from an ablation energy generator.

9. The treatment system of claim 1, wherein the ablation energy comprises radiofrequency energy.

10. The treatment system of claim 1, wherein the catheter further comprises a plurality of irrigation pores configured to vent irrigant to the tissue.

11. The treatment system of claim 10, wherein the catheter is configured to vent an amount of irrigant from the plurality of irrigation pores based on the sensed electrical signals from the tissue.

12. The treatment system of claim 1, wherein the ablation electrodes are configured in the first array of size selected from the range of 2×2 to 12×12.

13. The treatment system of claim 1, wherein the sensing electrodes are configured in the second array of size selected from the range of 2×2 to 12×12.

14. The treatment system of claim 1, wherein the catheter is collapsible into a sheath and expandable for treatment.

15. The treatment system of claim 1, wherein the catheter is configured to deliver the ablation energy through the subset of the ablation electrodes identified in an ablation procedure.

16. The treatment system of claim 1, wherein the control system is configured to determine the ablation pattern by determining a type of energy waveform with which to activate each ablation electrode in the subset.

17. The treatment system of claim 1, wherein the control system is configured to determine the ablation pattern by determining a frequency of energy with which to activate each ablation electrode in the subset.

18. The treatment system of claim 1, wherein the control system is configured to determine the ablation pattern by determining a duration with which to activate each ablation electrode in the subset.

* * * * *